US011401323B2

(12) United States Patent
Ogembo et al.

(10) Patent No.: US 11,401,323 B2
(45) Date of Patent: Aug. 2, 2022

(54) EPSTEIN-BARR VIRUS ANTIBODIES AND USES THEREOF

(71) Applicants: CITY OF HOPE, Duarte, CA (US); CALIFORNIA INSTITUTE OF TECHNOLOGY, Pasadena, CA (US)

(72) Inventors: Javier Gordon Ogembo, San Dimas, CA (US); Lorraine Zvichapera Mutsvunguma, Duarte, CA (US); Alison Evelynn Ondrus, Pasadena, CA (US)

(73) Assignees: CITY OF HOPE, Duarte, CA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/609,078

(22) PCT Filed: Apr. 27, 2018

(86) PCT No.: PCT/US2018/030030
§ 371 (c)(1),
(2) Date: Oct. 28, 2019

(87) PCT Pub. No.: WO2018/201099
PCT Pub. Date: Nov. 1, 2018

(65) Prior Publication Data
US 2020/0055924 A1    Feb. 20, 2020

Related U.S. Application Data

(60) Provisional application No. 62/491,945, filed on Apr. 28, 2017.

(51) Int. Cl.
| | | |
|---|---|---|
| *C07K 16/08* | (2006.01) | |
| *A61K 47/68* | (2017.01) | |
| *A61K 47/65* | (2017.01) | |
| *A61K 35/763* | (2015.01) | |
| *A61K 38/16* | (2006.01) | |
| *A61K 39/245* | (2006.01) | |
| *A61K 39/42* | (2006.01) | |

(52) U.S. Cl.
CPC .......... *C07K 16/085* (2013.01); *A61K 35/763* (2013.01); *A61K 38/162* (2013.01); *A61K 39/245* (2013.01); *A61K 47/65* (2017.08); *A61K 47/6811* (2017.08); *A61K 47/6839* (2017.08); *A61K 39/42* (2013.01); *C07K 2317/24* (2013.01); *C07K 2317/34* (2013.01); *C07K 2317/76* (2013.01); *C12N 2710/16222* (2013.01)

(58) Field of Classification Search
CPC .............. C07K 16/085; C07K 2317/24; C07K 2317/34; C07K 2317/76; A61K 35/763; A61K 38/162; A61K 39/245; A61K 47/65; A61K 47/6811; A61K 47/6839; A61K 39/42; A61K 47/6803; A61K 2039/505; C12N 2710/16222

See application file for complete search history.

(56) References Cited

U.S. PATENT DOCUMENTS

2015/0064174 A1*   3/2015  Wang ................... C07K 16/085
                                                         424/133.1

FOREIGN PATENT DOCUMENTS

WO        2018/200742 A1    11/2018

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*
Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*
Kussie PH, Parhami-Seren B, Wysocki LJ, et. al. A single engineered amino acid substitution changes antibody fine specificity. J Immunol. Jan. 1, 1994;152(1):146-52. (Year: 1994).*
Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year: 2015).*
Sela-Culang I, Kunik V, Ofran Y. The structural basis of antibody-antigen recognition. Front Immunol. Oct. 8, 2013;4:302. (Year: 2013).*

(Continued)

*Primary Examiner* — Rachel B Gill
(74) *Attorney, Agent, or Firm* — Perkins Coie LLP; Lara J. Dueppen; Yang Tang

(57) ABSTRACT

Disclosed herein are antibodies or immunogenic fragments thereof that specifically bind to Epstein-Barr virus (EBV) glycoprotein 350 (gp350) or 220 or one or more epitopes of EBV gp350 and neutralize EBV infection. Also disclosed are immunogenic peptides comprising one or more gp350 epitopes, EBV antibody-small molecule conjugates and pharmaceutical compositions comprising the antibody or an immunogenic fragment thereof, one or more epitopes of EBV gp350, one or more immunogenic peptides, or the EBV antibody-small molecule conjugate. The antibodies, epitopes, immunogenic peptides, conjugates, and pharmaceutical compositions can be used to treat or prevent EBV infections and EBV-associated conditions and diseases.

19 Claims, 10 Drawing Sheets

Specification includes a Sequence Listing.

(56) References Cited

OTHER PUBLICATIONS

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2016).*
Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*
Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*
Dondelinger M, Filée P, Sauvage E, Quinting B, Muyldermans S, Galleni M, Vandevenne MS. Understanding the Significance and Implications of Antibody Numbering and Antigen-Binding Surface/Residue Definition. Front Immunol. Oct. 16, 2018;9:2278. (Year: 2018).*
Kanekiyo M, Bu W, Joyce MG, Meng G, Whittle JR, Baxa U, Yamamoto T, Narpala S, Todd JP, Rao SS, McDermott AB, Koup RA, Rossmann MG, Mascola JR, Graham BS, et. al. Rational Design of an Epstein-Barr Virus Vaccine Targeting the Receptor-Binding Site. Cell. Aug. 27, 2015;162(5):1090-100. Epub Aug. 13, 2015. (Year: 2015).*
Sashihara J, Burbelo PD, Savoldo B, et. al. Human antibody titers to Epstein-Barr Virus (EBV) gp350 correlate with neutralization of infectivity better than antibody titers to EBV gp42 using a rapid flow cytometry-based EBV neutralization assay. Virology. Sep. 1, 2009;391(2):249-56. Epub Jul. 7, 2009. (Year: 2009).*
Mutsvunguma LZ, Rodriguez E, et. al. Identification of multiple potent neutralizing and non-neutralizing antibodies against Epstein-Barr virus gp350 protein with potential for clinical application and as reagents for mapping immunodominant epitopes. Virology. Oct. 2019;536:1-15. Epub Jul. 30, 2019. (Year: 2019).*
Alfarano, C., et al., "The biomolecular interaction network database and related tools 2005 update," Nucleic Acids Res. 33:D418-D424 (2005).
Babcock, G. J., et al., "EBV persistence in memory B cells in vivo," Immunity 9:395-404 (1998).
Baghian, A., et al., "Glycoprotein B of human herpesvirus 8 is a component of the virion in a cleaved form composed of amino- and carboxyl-terminal fragments," Virol. 269:18-25 (2000).
Balfour, H. H., et al., "Progress, prospects, and problems in Epstein-barr virus vaccine development," Curr. Opin. Virol. 0:1-5 (2014).
Benkerrou, M., et al., "Anti-B-cell monoclonal antibody treatment of severe posttransplant B-lymphoproliferative disorder: Prognostic factors and long-term outcome," Blood 92(9):3137-3147 (1998).
Biggar, R. J., et al., "Primary Epstein-Barr virus infections in African infants. I. Decline of Maternal antibodies and time of infection," Int. J. Cancer 22:239-243 (1978).
Biggar, R. J., et al., "Primary Epstein-Barr virus infections in African Infants. II. Clinical and Serological Observations during seroconversion," Int. J. Cancer 22: 244-250 (1978).
Bowie, J. U., et al., "Deciphering the Message in Protein Sequences: Tolerance to Amino Acid Substitutions," Science 247:1306-1310 (1990).
Brochet, X., et al., "IMGT/V-QUEST: the highly customized and integrated system for IG and TR standardized V-J and V-D-J sequence analysis," Nucleic Acids Res. 36:W503-W508 (2008).
Broering, T. J., et al., "Identification and characterization of broadly neutralizing human monoclonal antibodies directed against the E2 envelope glycoprotein of Hepatitis C virus," J. Virol. 83(23):12473-12482 (2009).
Bu, W., et al., "Immunization with components of the viral fusion apparatus elicits antibodies that neutralize Epstein-Barr virus in B cells and epithelial cells," Immunity 50(5):1305-1316 (2019).
Chen, J., et al., "Ephrin receptor A2 is a functional entry receptor for Epstein-barr virus," Nat. Microbiol. 3(2):172-180 (2018).
Chen, Z., et al., "Human monoclonal antibodies targeting the haemagglutinin glycoprotein can neutralize H7N9 influenza virus," Nat. Commun. 6:6714 (2015).
Chesnokova, L. S., et al., "Fusion of epithelial cells by Epstein-barr virus proteins is triggered by binding of viral glycoproteins gHgL to integrins $\alpha v\beta 6$ or $\alpha v\beta 8$," Proc. Natl. Acad. Sci. USA 106(48):20464-20469 (2009).
Chiuppesi, F., et al., "Vaccine-derived neutralizing antibodies to the human cytomegalovirus gH/gL pentamer potently block primary cytotrophoblast infection," J. Virol. 89(23):11884-11898 (2015).
Cohen, J. I., "Epstein-barr virus infection," New Engl. J. Med. 343(7):481-492 (2000).
Cohen, J. I., et al., "Epstein-barr virus: An important vaccine target for cancer prevention," Sci. Transl. Med. 3(107):107fs7 (2011).
Cohen, J. I., et al., "Epstein-barr virus vaccines," Clin. Transl. Immunol. 4:e32 (2015).
Collis, A. V. J., et al., "Analysis of the antigen combining site: Correlations between length and sequence composition of the hypervariable loops and the nature of the antigen," J. Mol. Biol. 325:337-354 (2003).
Connolly, S. A., et al., "Fusing structure and function: a structural view of the herpesvirus entry machinery," Nat. Rev. Microbiol. 9(5):369-381 (2011).
Cote, T. R., et al., "Non-Hodgkin's lymphoma among people with AIDS: Incidence, presentation and public health burden," Int. J. Cancer 73:645-650 (1997).
Cruz, R. J., et al., "Surgical management of gastrointestinal post-transplant lymphoproliferative disorders in liver transplant recipients," Transplantation 94:417-423 (2012).
Cui, X., et al., "Rabbits immunized with Epstein-Barr virus gH/gL or gB recombinant proteins elicit higher serum virus neutralizing activity than gp350," Vaccine 34:4050-4055 (2016).
Donaldson, J. M., et al., "Identification and grafting of a unique peptide-binding site in the Fab framework of monoclonal antibodies," Proc. Natl. Acad. Sci. USA 110(43):17456-17461 (2013).
Dondelinger, M., et al., "Understanding the significance and implications of antibody numbering and antigen-binding surface/residue definition," Front. Immunol. 9(2278):1-15 (2018).
Dubowchik, G. M., et al., "Cathepsin B-sensitive dipeptide prodrugs. 1. A model study of structural requirements for efficient release of doxorubicin," Bioorg. Med. Chem. Ltr. 8:3341-3346 (1998).
Dzeng, R. K., et al., "Small molecule growth inhibitors of human oncogenic gammaherpesvirus infected B-cells," Mol. Oncol. 9:365-376 (2015).
Eisenberg, R. J., et al., "Herpes virus fusion and entry: A story with many characters," Viruses 4:800-832 (2012).
Faro, A., et al., "Interferon-alpha affects the immune response in post-transplant lymphoproliferative disorder," Am. J. Respir. Crit. Care Med. 153:1442-1447 (1996).
Ferrara, N., et al., "Discovery and development of Bevacizumab, an anti-VEGF antibody for treating cancer," Nat. Rev. Drug Discov. 3:391-400 (2004).
Finerty, S., et al., "Immunization of cottontop tamarins and rabbits with a candidate vaccine against the Epstein-Barr virus based on the major viral envelope glycoprotein gp340 and alum," Vaccine 12(13):1180-1184 (1994).
Fingeroth, J. D., et al., "Epstein-barr virus receptor of human B lymphocytes is the C3d receptor CR2," Proc. Natl. Acad. Sci. USA 81:4510-4514 (1984).
Glotz, D., et al., "The Seville expert workshop for progress in posttransplant lymphoproliferative disorders," Transplantation 94:784-793 (2012).
Goedert, J. J., et al., "Spectrum of AIDS-associated malignant disorders," Lancet 351:1833-1839 (1998).
Gu, S. Y., et al., "First EBV vaccine trial in humans using recombinant vaccinia virus expressing the major membrane antigen," Dev. Biol. Stand. 84:171-177 (1995).
Han, T., et al., "Structural basis of influenza virus neutralization," Ann. N.Y. Acad. Sci. 1217:178-190 (2011).
Haque, T., et al., "A mouse monoclonal antibody against Epstein-barr virus envelope glycoprotein 350 prevents infection both in vitro and in vivo," J. Infect. Dis. 194:584-587 (2006).

(56) References Cited

OTHER PUBLICATIONS

Henle, G., et al., "Relation of Burkitt's tumor-associated herpes-type virus to infectious mononucleosis," Microbiol. 59:94-101 (1968).

Henle, G., et al., "The virus as the etiologic agent of infectious mononucleosis," The Epstein-Barr Virus (1979) pp. 297-320.

Herrman, M., et al., "Epstein-barr virus gp350 can functionally replace the rhesus lymphocryptovirus major membrane glycoprotein and does not restrict infection of rhesus macaques," J. Virol. 90(3):1222-1230 (2016).

Hoffman, G. J., et al., "Monoclonal antibody against a 250,000-dalton glycoprotein of Epstein-barr virus identifies a membrane antigen and a neutralizing antigen," Proc. Natl. Acad. Sci. USA 77(5):2979-2983 (1980).

Hudis, C. A., "Trastuzumab—Mechanism of action and use in clinical practice," New Engl. J. Med. 357:39-51 (2007).

Jangalwe, S., et al., "Improved B cell development in humanized NOD-scid IL2Rγ$^{null}$ mice transgenically expressing human stem cell factor, granulocyte-macrophage colony-stimulating factor and interleukin-3," Immunity, Inflammation and Disease 4(4):427-440 (2016).

Jiang, L., et al., "EBNA1-targeted probe for the imaging and growth inhibition of tumours associated with the Epstein-Barr virus," Nat. Biomed. Engineering 1:0042 (2017).

Jones, S. T., et al., "Rapid PCR-Cloning of Full-Length Mouse Immunoglobulin Variable Regions," Biotechnology 9:579 (1991).

Jonker, D. J., et al., "Cetuximab for the Treatment of Colorectal Cancer," New Engl. J. Med. 357:2040-2048 (2007).

Kanekiyo, M., et al., "Rational design of an Epstein-Barr virus vaccine targeting the receptor-binding site," Cell 162:1090-1100 (2015).

Khanna, R., et al., "EBV structural antigens, gp350 and gp85, as targets for ex vivo virus-specific CTL during acute infectious mononucleosis: Potential use of gp350/gp85 CTL epitopes for vaccine design," J. Immunol. 162:3063-3069 (1999).

Khyatti, M., et al., "Epstein-barr virus (EBV) glycoprotein gp350 expressed on transfected cells resistant to natural killer cell activity serves as a target antigen for EBV-specific antibody-dependent cellular cytotoxicity," J. Virol. 65(2):996-1001 (1991).

Kussie, P. H., et al., "A single engineered amino acid substitution changes antibody fine specificity," J. Immunol. 152:146-152 (1994).

Luzuriaga, K., et al., "Infectious mononucleosis," New Engl. J. Med. 362:1993-2000 (2010).

Milpied, N., et al., "Humanized anti-CD20 monoclonal antibody (Rituximab) in post transplant B-lymphoproliferative disorder: A retrospective analysis on 32 patients," Annals of Oncology 11(Suppl. 1): S113-S116 (2000).

Mok, H., et al., "Evaluation of measles vaccine virus as a vector to deliver respiratory syncytial virus fusion protein or Epstein-barr virus glycoprotein gp350," Open Virol. J. 6:12-22 (2012).

Mold, C., et al., "Activation of the alternative complement pathway by EBV and the viral envelope glycoprotein, gp350," J. Immunol. 140:3867-3874 (1988).

Moutschen, M., et al., "Phase I/II studies to evaluate safety and immunogenicity of a recombinant gp350 Epstein-Barr virus vaccine in healthy adults," Vaccine 25:4697-4705 (2007).

Mulama, D. H., et al., "A multivalent Kaposi sarcoma-associated herpesvirus-like particle vaccine capable of eliciting high titers of neutralizing antibodies in immunized rabbits," Vaccine 37(30):4184-4194 (2019).

Mutsvunguma, L. Z., et al., "Identification of multiple potent neutralizing and non-neutralizing antibodies against Epstein-Barr virus gp350 protein with potential for clinical application and as reagents for mapping immunodominant epitopes," Virol. 536:1-15 (2019).

Nemerow, G. R., et al., "Identification of gp350 as the viral glycoprotein mediating attachment of Epstein-barr virus (EBV) to the EBV/C3d receptor of B cells: Sequence homology of gp350 and C3 complement fragment C3d," J. Virol. 61(5):1416-1420 (1987).

Nemerow, G. R., et al., "Identification of an epitope in the major envelope protein of Epstein-Barr virus that mediates viral binding to the B lymphocyte EBV receptor (CR2)," Cell 56:369-377 (1989).

Ogembo, J. G., et al., "Human complement receptor type 1/CD35 is an Epstein-barr virus receptor," Cell Rep. 3(2):371-385 (2013).

Ogembo, J. G., et al., "A chimeric EBV gp350/220-based VLP replicates the virion B-cell attachment mechanism and elicits long-lasting neutralizing antibodies in mice," J. Transl. Med. 13:50 (2015).

Papadopoulos, E. B., et al., "Infusions of donor leukocytes to treat Epstein-barr virus-associated lymphoproliferative disorders after allogeneic bone marrow transplantation," N. Engl. J. Med. 330(17):1185-1191 (1994).

Pei, J., et al., "PROMALS3D: a tool for multiple protein sequence and structure alignments," Nucleic Acids Res. 36(7):2295-2300 (2008).

Perez, E. M., et al., "Novel Epstein-barr virus-like particles incorporating gH/gL-EBNA1 or gB-LMP2 induce high neutralizing antibody titers and EBV-specific T-cell responses in immunized mice," Oncotarget 8(12):19255-19273 (2017).

Piedimonte, G., et al., "A humanized monoclonal antibody against respiratory syncytial virus (Palivizumab) inhibits RSV-induced neurogenic-mediated inflammation in rat airways," Pediat. Res. 47(3):351-356 (2000).

Qualtiere, L. F., et al., "Epitope mapping of the major Epstein-barr virus outer envelope glycoprotein gp350/220," J. Gen. Virol. 68:535-543 (1987).

Rees, L., et al., "A phase I trial of Epstein-barr virus Gp350 vaccine for children with chronic kidney disease awaiting transplantation," Transplant. 88:1025-1029 (2009).

Rickinson, A. B., "Epstein-Barr Virus," Fields Virology, 5th Ed., Lippincott Wiliams & Wilkins, 78 pages (2007).

Sashihara, J., et al., "Human antibody titers to Epstein-barr virus (EBV) gp350 correlate with neutralization of infectivity better than antibody titers to EBV gp42 using a rapid flow cytometry-based EBV neutralization assay," Virol. 391(2):249-256 (2009).

Sela, M., et al., "Antibodies to sequential and conformational determinants," Cold Spring Harbor Symposia on Quantitative Biology 32:537-545 (1967).

Sela-Culang, I., et al., "The structural basis of antibody-antigen recognition," Front. Immunol. 4(302):1-13 (2013).

Senter, P. D., et al., "The discovery and development of brentuximab vedotin for use in relapsed Hodgkin lymphoma and systemic anaplastic large cell lymphoma," Nat. Biotechnol. 30(7):631-637 (2012).

Sirin, S., et al., "AB-Bind: Antibody binding mutational database for computational affinity predictions," Protein Sci. 25:393-409 (2016).

Sitompul, L. S., et al., "Epitope mapping of gp350/220 conserved domain of epstein barr virus to develop nasopharyngeal carcinoma (npc) vaccine," Bioinformation 8(10):479-482 (2012).

Sokal, E. M., et al., "Recombinant gp350 vaccine for infectious mononucleosis: A phase 2, randomized, double-blind, placebo-controlled trial to evaluate the safety, immunogenicity, and efficacy of an Epstein-barr virus vaccine in healthy young adults," J. Infect. Dis. 196:1749-1753 (2007).

Speck, P., et al., "Epstein-Barr virus (EBV) infection visualized by EGFP expression demonstrates dependence on known mediators of EBV entry," Arch. Virol. 144:1123-1137 (1999).

Stamatatos, L., et al., "Neutralizing antibodies generated during natural HIV-1 infection: Good news for an HIV-1 vaccine?" Nat. Med. 15(8):866-870 (2009).

Sui, J., et al., "Structural and functional bases for broad-spectrum neutralization of avian and human influenza A viruses," Nat. Struct. Mol. Biol. 16(3):265-273 (2009).

Szakonyi, G., et al., "Structure of the Epstein-Barr virus major envelope glycoprotein," Nat. Struct. Mol. Biol. 13(11):996-1001 (2006).

Tanner, J., et al., "Epstein-Barr virus gp350/220 binding to the B lymphocyte C3d receptor mediates adsorption, capping, and endocytosis," Cell 50:203-213 (1987).

(56) References Cited

OTHER PUBLICATIONS

Tanner, J., et al., "Soluble gp350/220 and deletion mutant glycoproteins block Epstein-barr virus adsorption to lymphocytes," J. Virol. 62(12):4452-4464 (1988).

Tanner, J. E., et al., "Peptides designed to spatially depict the Epstein-barr virus major virion glycoprotein gp350 neutralization epitope elicit antibodies that block virus-neutralizing antibody 72A1 interaction with the native gp350 molecule," J. Virol. 89:4932-4941 (2015).

Tanner, J. E., et al., "Construction and characterization of a humanized anti-Epstein-barr virus gp350 antibody with neutralizing activity in cell culture," Cancers 10:112 (2018).

Thorley-Lawson, D. A., et al., "Monoclonal antibodies against the major glycoprotein (gp350/220) of Epstein-barr virus neutralize infectivity," Proc. Natl. Acad. Sci. USA 77(9):5307-5311 (1980).

Thorley-Lawson, D. A., et al., "Identification and isolation of the main component (gp350-gp220) of Epstein-barr virus responsible for generating neutralizing antibodies in vivo," J. Virol. 43(2)730-736 (1982).

Tsuchiya, Y., et al., "The diversity of H3 loops determines the antigen-binding tendencies of antibody CDR loops," Protein Sci. 25:815-825 (2016).

Tugizov, S. M., et al., "Epstein-Barr virus infection of polarized tongue and nasopharyngeal epithelial cells," Nat. Med. 9(3):307-314 (2003).

United States Patent and Trademark Office, International Search Report and Written Opinion dated Aug. 7, 2018 for PCT/US18/30030.

Urquiza, M., et al., "Identification of three gp350/220 regions involved in Epstein-barr virus invasion of host cells," J. Biol. Chem. 280(42):35598-35605 (2005).

Walker, L. M., et al., "Broad and potent neutralizing antibodies from an African donor reveal a new HIV-1 vaccine target," Science 326(5950):285-289 (2009).

Weiss, E. R., et al., "High Epstein-barr virus load and genomic diversity are associated with generation of gp350-specific neutralizing antibodies following acute infectious mononucleosis," J. Virol. 91(1):e01562-16 (2016).

Winkler, K., et al., "Changing the antigen binding specificity by single point mutations of an anti-p24 (HIV-1) antibody," J. Immunol. 165:4505-4514 (2000).

Wrammert, J., et al., "Rapid cloning of high affinity human monoclonal antibodies against influenza virus," Nature 453(7195):667-671 (2008).

Zhang, P.F., et al., "Mapping of the epitopes of Epstein-barr virus gp350 using monoclonal antibodies and recombinant proteins expressed in *Escherichia coli* defines three antigenic determinants," J. Gen. Virol. 72:2747-2755 (1991).

Zhang, H., et al., "Ephrin receptor A2 is an epithelial cell receptor for Epstein-Barr virus entry," Nat. Microbiol. 3:164-171 (2018).

\* cited by examiner

SEQUENCE LISTING

<160> NUMBER OF SEQ ID NOS: 131

<210> SEQ ID NO 1

```
<211> LENGTH: 23
<212> TYPE: PRT
<213> ORGANISM: Artificial Sequence
<220> FEATURE:
<223> OTHER INFORMATION: immunodominant epitope

<400> SEQUENCE: 1

Thr Pro Ile Pro Gly Thr Gly Tyr Ala Tyr Ser Leu Arg Leu Thr Pro
1               5                   10                  15

Arg Pro Val Ser Arg Phe Leu
            20

<210> SEQ ID NO 2
<211> LENGTH: 26
<212> TYPE: PRT
<213> ORGANISM: Artificial Sequence
<220> FEATURE:
<223> OTHER INFORMATION: immunodominant epitope

<400> SEQUENCE: 2

Leu Leu Leu Leu Val Met Ala Asp Cys Ala Phe Arg Arg Asn Leu Ser
1               5                   10                  15

Thr Ser His Thr Tyr Thr Thr Pro Pro Tyr
            20                  25

<210> SEQ ID NO 3
<211> LENGTH: 12
<212> TYPE: PRT
<213> ORGANISM: Artificial Sequence
<220> FEATURE:
<223> OTHER INFORMATION: novel nAb epitope

<400> SEQUENCE: 3

Gly Ala Phe Ala Ser Asn Arg Thr Phe Asp Ile Thr
1               5                   10

<210> SEQ ID NO 4
<211> LENGTH: 7
<212> TYPE: PRT
<213> ORGANISM: Artificial Sequence
<220> FEATURE:
<223> OTHER INFORMATION: VH CDR-1 72A1

<400> SEQUENCE: 4

Gly Ser Ser Phe Thr Asp Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: VH CDR-1 HB-1

<400> SEQUENCE: 5

Gly Phe Leu Leu Thr Thr Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: VH CDR-1 HB-2

<400> SEQUENCE: 6
```

```
Gly Tyr Thr Phe Thr Ala Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: VH CDR-1 HB-3

<400> SEQUENCE: 7

Gly Tyr Thr Phe Ala Ser Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: VH CDR-1 HB-5

<400> SEQUENCE: 8

Gly Tyr Thr Phe Thr Asn His
1               5

<210> SEQ ID NO 9
<211> LENGTH: 7
<212> TYPE: PRT
<213> ORGANISM: Artificial Sequence
<220> FEATURE:
<223> OTHER INFORMATION: VH CDR-1 HB-6

<400> SEQUENCE: 9

Gly Tyr Thr Phe Thr Asp Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: VH CDR-1 HB-7

<400> SEQUENCE: 10

Gly Tyr Thr Phe Thr Asp Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: VH CDR-1 HB-8

<400> SEQUENCE: 11

Gly Tyr Ser Phe Thr Asn Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: VH CDR-1 HB-9

<400> SEQUENCE: 12

Gly Phe Thr Phe Ser Ser Tyr
```

```
1               5

<210> SEQ ID NO 13
<211> LENGTH: 7
<212> TYPE: PRT
<213> ORGANISM: Artificial Sequence
<220> FEATURE:
<223> OTHER INFORMATION: VH CDR-1 HB-10

<400> SEQUENCE: 13

Gly Tyr Thr Phe Thr Ser Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: VH CDR-1 HB-11

<400> SEQUENCE: 14

Gly Asp Ser Ile Thr Ser Gly
1               5

<210> SEQ ID NO 15
<211> LENGTH: 7
<212> TYPE: PRT
<213> ORGANISM: Artificial Sequence
<220> FEATURE:
<223> OTHER INFORMATION: VH CDR-1 HB-12

<400> SEQUENCE: 15

Gly Tyr Thr Phe Thr Asn Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: VH CDR-1 HB-14

<400> SEQUENCE: 16

Gly Tyr Thr Phe Thr Asp Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: VH CDR-1 HB-17

<400> SEQUENCE: 17

Gly Tyr Thr Phe Thr Ser Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: VH CDR-1 HB-20

<400> SEQUENCE: 18

Gly Tyr Thr Phe Thr Ser Tyr
1               5
```

```
<210> SEQ ID NO 19
<211> LENGTH: 7
<212> TYPE: PRT
<213> ORGANISM: Artificial Sequence
<220> FEATURE:
<223> OTHER INFORMATION: VH CDR-1 HB-22

<400> SEQUENCE: 19

Gly Phe Ser Leu Thr Asn Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: VH CDR-2 72A1

<400> SEQUENCE: 20

Ile Asn Pro Tyr Asn Gly Gly
1               5

<210> SEQ ID NO 21
<211> LENGTH: 6
<212> TYPE: PRT
<213> ORGANISM: Artificial Sequence
<220> FEATURE:
<223> OTHER INFORMATION: VH CDR-2 HB-1

<400> SEQUENCE: 21

Ile Trp Ala Gly Gly Ser
1               5

<210> SEQ ID NO 22
<211> LENGTH: 7
<212> TYPE: PRT
<213> ORGANISM: Artificial Sequence
<220> FEATURE:
<223> OTHER INFORMATION: VH CDR-2 HB-2

<400> SEQUENCE: 22

Ile Asn Tyr Lys Thr Gly Glu
1               5

<210> SEQ ID NO 23
<211> LENGTH: 7
<212> TYPE: PRT
<213> ORGANISM: Artificial Sequence
<220> FEATURE:
<223> OTHER INFORMATION: VH CDR-2 HB-3

<400> SEQUENCE: 23

Ile Asn Pro Asn Asn Gly His
1               5

<210> SEQ ID NO 24
<211> LENGTH: 7
<212> TYPE: PRT
<213> ORGANISM: Artificial Sequence
<220> FEATURE:
<223> OTHER INFORMATION: VH CDR-2 HB-5

<400> SEQUENCE: 24

Ile Asn Pro Tyr Asn Asp Tyr
1               5
```

```
<210> SEQ ID NO 25
<211> LENGTH: 7
<212> TYPE: PRT
<213> ORGANISM: Artificial Sequence
<220> FEATURE:
<223> OTHER INFORMATION: VH CDR-2 HB-6

<400> SEQUENCE: 25

Ile Asn Thr Arg Thr Gly Glu
1               5

<210> SEQ ID NO 26
<211> LENGTH: 7
<212> TYPE: PRT
<213> ORGANISM: Artificial Sequence
<220> FEATURE:
<223> OTHER INFORMATION: VH CDR-2 HB-7

<400> SEQUENCE: 26

Ile Ser Pro Gly Arg Ser Gly
1               5

<210> SEQ ID NO 27
<211> LENGTH: 7
<212> TYPE: PRT
<213> ORGANISM: Artificial Sequence
<220> FEATURE:
<223> OTHER INFORMATION: VH CDR-2 HB-8

<400> SEQUENCE: 27

Ile Asn Thr Tyr Thr Gly Glu
1               5

<210> SEQ ID NO 28
<211> LENGTH: 7
<212> TYPE: PRT
<213> ORGANISM: Artificial Sequence
<220> FEATURE:
<223> OTHER INFORMATION: VH CDR-2 HB-9

<400> SEQUENCE: 28

Ile Ser Ser Gly Gly Ser Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: VH CDR-2 HB-10

<400> SEQUENCE: 29

Ile Asn Pro Ser Asn Gly His
1               5

<210> SEQ ID NO 30
<211> LENGTH: 6
<212> TYPE: PRT
<213> ORGANISM: Artificial Sequence
<220> FEATURE:
<223> OTHER INFORMATION: VH CDR-2 HB-11

<400> SEQUENCE: 30

Ile Ser Tyr Ser Gly Ser
1               5
```

<210> SEQ ID NO 31
<211> LENGTH: 7
<212> TYPE: PRT
<213> ORGANISM: Artificial Sequence
<220> FEATURE:
<223> OTHER INFORMATION: VH CDR-2 HB-12

<400> SEQUENCE: 31

Ile Asn Pro Asn Asn Gly His
1               5

<210> SEQ ID NO 32
<211> LENGTH: 7
<212> TYPE: PRT
<213> ORGANISM: Artificial Sequence
<220> FEATURE:
<223> OTHER INFORMATION: VH CDR-2 HB-14

<400> SEQUENCE: 32

Ile His Pro Arg Arg Gly Gly
1               5

<210> SEQ ID NO 33
<211> LENGTH: 7
<212> TYPE: PRT
<213> ORGANISM: Artificial Sequence
<220> FEATURE:
<223> OTHER INFORMATION: VH CDR-2 HB-17

<400> SEQUENCE: 33

Ile Asn Pro Asn Asn Gly His
1               5

<210> SEQ ID NO 34
<211> LENGTH: 7
<212> TYPE: PRT
<213> ORGANISM: Artificial Sequence
<220> FEATURE:
<223> OTHER INFORMATION: VH CDR-2 HB-20

<400> SEQUENCE: 34

Ile Asn Pro Thr Asn Gly His
1               5

<210> SEQ ID NO 35
<211> LENGTH: 6
<212> TYPE: PRT
<213> ORGANISM: Artificial Sequence
<220> FEATURE:
<223> OTHER INFORMATION: VH CDR-2 HB-22

<400> SEQUENCE: 35

Ile Trp Ser Asp Gly Ser
1               5

<210> SEQ ID NO 36
<211> LENGTH: 12
<212> TYPE: PRT
<213> ORGANISM: Artificial Sequence
<220> FEATURE:
<223> OTHER INFORMATION: VH CDR-3 72A1

<400> SEQUENCE: 36

Gly Gly Leu Arg Arg Val Asn Trp Phe Ala Tyr Trp
1               5                   10

<210> SEQ ID NO 37

-continued

```
<211> LENGTH: 14
<212> TYPE: PRT
<213> ORGANISM: Artificial Sequence
<220> FEATURE:
<223> OTHER INFORMATION: VH CDR-3 HB-1

<400> SEQUENCE: 37

Arg Asp Arg Gly Tyr Gly Tyr Leu Tyr Ala Met Asp Tyr Trp
1               5                   10

<210> SEQ ID NO 38
<211> LENGTH: 9
<212> TYPE: PRT
<213> ORGANISM: Artificial Sequence
<220> FEATURE:
<223> OTHER INFORMATION: VH CDR-3 HB-2

<400> SEQUENCE: 38

Pro Tyr Gly Tyr Ala Leu Asp Tyr Trp
1               5

<210> SEQ ID NO 39
<211> LENGTH: 12
<212> TYPE: PRT
<213> ORGANISM: Artificial Sequence
<220> FEATURE:
<223> OTHER INFORMATION: VH CDR-3 HB-3

<400> SEQUENCE: 39

Arg Asn Leu Tyr Tyr Tyr Gly Arg Pro Asp Tyr Trp
1               5                   10

<210> SEQ ID NO 40
<211> LENGTH: 14
<212> TYPE: PRT
<213> ORGANISM: Artificial Sequence
<220> FEATURE:
<223> OTHER INFORMATION: VH CDR-3 HB-5

<400> SEQUENCE: 40

Arg Ser Glu Gly Trp Leu Arg Arg Gly Ala Trp Phe Ala Tyr
1               5                   10

<210> SEQ ID NO 41
<211> LENGTH: 9
<212> TYPE: PRT
<213> ORGANISM: Artificial Sequence
<220> FEATURE:
<223> OTHER INFORMATION: VH CDR-3 HB-6

<400> SEQUENCE: 41

Pro Tyr Gly Tyr Ala Leu Asp Tyr Trp
1               5

<210> SEQ ID NO 42
<211> LENGTH: 11
<212> TYPE: PRT
<213> ORGANISM: Artificial Sequence
<220> FEATURE:
<223> OTHER INFORMATION: VH CDR-3 HB-7

<400> SEQUENCE: 42

Arg Tyr Gly His Pro Ser Tyr Leu Asp Val Trp
1               5                   10

<210> SEQ ID NO 43
<211> LENGTH: 15
```

```
<212> TYPE: PRT
<213> ORGANISM: Artificial Sequence
<220> FEATURE:
<223> OTHER INFORMATION: VH CDR-3 HB-8

<400> SEQUENCE: 43

Arg Tyr Tyr Tyr Gly Ser Val Tyr Ser Ala Trp Phe Ala Tyr Trp
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: VH CDR-3 HB-9

<400> SEQUENCE: 44

Arg Glu Asp Phe Tyr Tyr Gly Ser Ser Tyr Gly Phe Phe Asp Val Trp
1               5                   10                  15

<210> SEQ ID NO 45
<211> LENGTH: 12
<212> TYPE: PRT
<213> ORGANISM: Artificial Sequence
<220> FEATURE:
<223> OTHER INFORMATION: VH CDR-3 HB-10

<400> SEQUENCE: 45

Arg Asn Leu Tyr Tyr Tyr Gly Arg Pro Asp Tyr Trp
1               5                   10

<210> SEQ ID NO 46
<211> LENGTH: 14
<212> TYPE: PRT
<213> ORGANISM: Artificial Sequence
<220> FEATURE:
<223> OTHER INFORMATION: VH CDR-3 HB-11

<400> SEQUENCE: 46

Arg Gly Asn Gly Gly Asn Tyr Asp Trp Tyr Phe Asp Val Trp
1               5                   10

<210> SEQ ID NO 47
<211> LENGTH: 12
<212> TYPE: PRT
<213> ORGANISM: Artificial Sequence
<220> FEATURE:
<223> OTHER INFORMATION: VH CDR-3 HB-12

<400> SEQUENCE: 47

Arg Asn Leu Tyr Tyr Tyr Gly Arg Pro Asp Tyr Trp
1               5                   10

<210> SEQ ID NO 48
<211> LENGTH: 11
<212> TYPE: PRT
<213> ORGANISM: Artificial Sequence
<220> FEATURE:
<223> OTHER INFORMATION: VH CDR-3 HB-14

<400> SEQUENCE: 48

Arg Tyr Gly Tyr Pro Trp Tyr Phe Asp Val Trp
1               5                   10

<210> SEQ ID NO 49
<211> LENGTH: 12
<212> TYPE: PRT
```

<213> ORGANISM: Artificial Sequence
<220> FEATURE:
<223> OTHER INFORMATION: VH CDR-3 HB-17

<400> SEQUENCE: 49

Arg Asn Leu Phe Tyr Tyr Ser Arg Pro Asp Tyr Trp
1               5                   10

<210> SEQ ID NO 50
<211> LENGTH: 12
<212> TYPE: PRT
<213> ORGANISM: Artificial Sequence
<220> FEATURE:
<223> OTHER INFORMATION: VH CDR-3 HB-20

<400> SEQUENCE: 50

Arg Asn Leu Tyr Tyr Tyr Gly Arg Pro Asp Tyr Trp
1               5                   10

<210> SEQ ID NO 51
<211> LENGTH: 15
<212> TYPE: PRT
<213> ORGANISM: Artificial Sequence
<220> FEATURE:
<223> OTHER INFORMATION: VH CDR-3 HB-22

<400> SEQUENCE: 51

Arg Asn Tyr Tyr Gly Asn Ser Tyr Pro Ala Trp Phe Ala Tyr Trp
1               5                   10                  15

<210> SEQ ID NO 52
<211> LENGTH: 9
<212> TYPE: PRT
<213> ORGANISM: Artificial Sequence
<220> FEATURE:
<223> OTHER INFORMATION: VL CDR-1 72A1

<400> SEQUENCE: 52

Thr Gly Ala Val Thr Thr Ser Asn Tyr
1               5

<210> SEQ ID NO 53
<211> LENGTH: 6
<212> TYPE: PRT
<213> ORGANISM: Artificial Sequence
<220> FEATURE:
<223> OTHER INFORMATION: VL CDR-1 HB-1

<400> SEQUENCE: 53

Gln Asn Val Gly Thr Asn
1               5

<210> SEQ ID NO 54
<211> LENGTH: 5
<212> TYPE: PRT
<213> ORGANISM: Artificial Sequence
<220> FEATURE:
<223> OTHER INFORMATION: VL CDR-1 HB-2

<400> SEQUENCE: 54

Ser Ser Val Asn Tyr
1               5

<210> SEQ ID NO 55
<211> LENGTH: 6
<212> TYPE: PRT
<213> ORGANISM: Artificial Sequence

```
<220> FEATURE:
<223> OTHER INFORMATION: VL CDR-1 HB-3

<400> SEQUENCE: 55

Gln Asp Ile Gly Asn Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: VL CDR-1 HB-5

<400> SEQUENCE: 56

Gln Ser Ile Gly Thr Ser
1               5

<210> SEQ ID NO 57
<211> LENGTH: 5
<212> TYPE: PRT
<213> ORGANISM: Artificial Sequence
<220> FEATURE:
<223> OTHER INFORMATION: VL CDR-1 HB-6

<400> SEQUENCE: 57

Ser Ser Val Asn Tyr
1               5

<210> SEQ ID NO 58
<211> LENGTH: 6
<212> TYPE: PRT
<213> ORGANISM: Artificial Sequence
<220> FEATURE:
<223> OTHER INFORMATION: VL CDR-1 HB-7

<400> SEQUENCE: 58

Gln Ser Val Gly Asn Ala
1               5

<210> SEQ ID NO 59
<211> LENGTH: 11
<212> TYPE: PRT
<213> ORGANISM: Artificial Sequence
<220> FEATURE:
<223> OTHER INFORMATION: VL CDR-1 HB-8

<400> SEQUENCE: 59

Gln Ser Ile Val His Ser Asn Gly Asn Thr Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: VL CDR-1 HB-9

<400> SEQUENCE: 60

Gln Ser Ile Val His Ser Asn Gly Asn Thr Tyr
1               5                   10

<210> SEQ ID NO 61
<211> LENGTH: 6
<212> TYPE: PRT
<213> ORGANISM: Artificial Sequence
<220> FEATURE:
```

<223> OTHER INFORMATION: VL CDR-1 HB-10

<400> SEQUENCE: 61

Gln Asp Ile Gly Asn Tyr
1               5

<210> SEQ ID NO 62
<211> LENGTH: 5
<212> TYPE: PRT
<213> ORGANISM: Artificial Sequence
<220> FEATURE:
<223> OTHER INFORMATION: VL CDR-1 HB-11

<400> SEQUENCE: 62

Ser Ser Val Asn Phe
1               5

<210> SEQ ID NO 63
<211> LENGTH: 11
<212> TYPE: PRT
<213> ORGANISM: Artificial Sequence
<220> FEATURE:
<223> OTHER INFORMATION: VL CDR-1 HB-12

<400> SEQUENCE: 63

Gln Ser Leu Val His Ser Asn Gly Asn Thr Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: VL CDR-1 HB-14

<400> SEQUENCE: 64

Gln Ser Ile Val His Asp Asn Gly Asn Thr Tyr
1               5                   10

<210> SEQ ID NO 65
<211> LENGTH: 6
<212> TYPE: PRT
<213> ORGANISM: Artificial Sequence
<220> FEATURE:
<223> OTHER INFORMATION: VL CDR-1 HB-17

<400> SEQUENCE: 65

Gln Asp Ile Gly Asn Tyr
1               5

<210> SEQ ID NO 66
<211> LENGTH: 6
<212> TYPE: PRT
<213> ORGANISM: Artificial Sequence
<220> FEATURE:
<223> OTHER INFORMATION: VL CDR-1 HB-20

<400> SEQUENCE: 66

Gln Asp Ile Gly Asn Tyr
1               5

<210> SEQ ID NO 67
<211> LENGTH: 11
<212> TYPE: PRT
<213> ORGANISM: Artificial Sequence
<220> FEATURE:
<223> OTHER INFORMATION: VL CDR-1 HB-22

```
<400> SEQUENCE: 67

Gln Ser Ile Val His Ser Asn Gly Asn Thr Tyr
1               5                   10

<210> SEQ ID NO 68
<211> LENGTH: 3
<212> TYPE: PRT
<213> ORGANISM: Artificial Sequence
<220> FEATURE:
<223> OTHER INFORMATION: VL CDR-2 72A1

<400> SEQUENCE: 68

Gly Thr Asn
1

<210> SEQ ID NO 69
<211> LENGTH: 3
<212> TYPE: PRT
<213> ORGANISM: Artificial Sequence
<220> FEATURE:
<223> OTHER INFORMATION: VL CDR-2 HB-1

<400> SEQUENCE: 69

Ser Thr Asp
1

<210> SEQ ID NO 70
<211> LENGTH: 3
<212> TYPE: PRT
<213> ORGANISM: Artificial Sequence
<220> FEATURE:
<223> OTHER INFORMATION: VL CDR-2 HB-2

<400> SEQUENCE: 70

Ala Thr Ser
1

<210> SEQ ID NO 71
<211> LENGTH: 3
<212> TYPE: PRT
<213> ORGANISM: Artificial Sequence
<220> FEATURE:
<223> OTHER INFORMATION: VL CDR-2 HB-3

<400> SEQUENCE: 71

Tyr Thr Ser
1

<210> SEQ ID NO 72
<211> LENGTH: 3
<212> TYPE: PRT
<213> ORGANISM: Artificial Sequence
<220> FEATURE:
<223> OTHER INFORMATION: VL CDR-2 HB-5

<400> SEQUENCE: 72

Tyr Ala Ser
1

<210> SEQ ID NO 73
<211> LENGTH: 3
<212> TYPE: PRT
<213> ORGANISM: Artificial Sequence
<220> FEATURE:
<223> OTHER INFORMATION: VL CDR-2 HB-6
```

```
<400> SEQUENCE: 73

Ala Thr Ser
1

<210> SEQ ID NO 74
<211> LENGTH: 3
<212> TYPE: PRT
<213> ORGANISM: Artificial Sequence
<220> FEATURE:
<223> OTHER INFORMATION: VL CDR-2 HB-7

<400> SEQUENCE: 74

Ser Ala Ser
1

<210> SEQ ID NO 75
<211> LENGTH: 3
<212> TYPE: PRT
<213> ORGANISM: Artificial Sequence
<220> FEATURE:
<223> OTHER INFORMATION: VL CDR-2 HB-8

<400> SEQUENCE: 75

Lys Val Ser
1

<210> SEQ ID NO 76
<211> LENGTH: 3
<212> TYPE: PRT
<213> ORGANISM: Artificial Sequence
<220> FEATURE:
<223> OTHER INFORMATION: VL CDR-2 HB-9

<400> SEQUENCE: 76

Lys Val Ser
1

<210> SEQ ID NO 77
<211> LENGTH: 3
<212> TYPE: PRT
<213> ORGANISM: Artificial Sequence
<220> FEATURE:
<223> OTHER INFORMATION: VL CDR-2 HB-10

<400> SEQUENCE: 77

Tyr Thr Ser
1

<210> SEQ ID NO 78
<211> LENGTH: 3
<212> TYPE: PRT
<213> ORGANISM: Artificial Sequence
<220> FEATURE:
<223> OTHER INFORMATION: VL CDR-2 HB-11

<400> SEQUENCE: 78

Tyr Ile Ser
1

<210> SEQ ID NO 79
<211> LENGTH: 3
<212> TYPE: PRT
<213> ORGANISM: Artificial Sequence
<220> FEATURE:
<223> OTHER INFORMATION: VL CDR-2 HB-12

<400> SEQUENCE: 79
```

<210> SEQ ID NO 80
<211> LENGTH: 3
<212> TYPE: PRT
<213> ORGANISM: Artificial Sequence
<220> FEATURE:
<223> OTHER INFORMATION: VL CDR-2 HB-14

<400> SEQUENCE: 80

Lys Val Ser
1

<210> SEQ ID NO 81
<211> LENGTH: 3
<212> TYPE: PRT
<213> ORGANISM: Artificial Sequence
<220> FEATURE:
<223> OTHER INFORMATION: VL CDR-2 HB-17

<400> SEQUENCE: 81

Tyr Thr Ser
1

<210> SEQ ID NO 82
<211> LENGTH: 3
<212> TYPE: PRT
<213> ORGANISM: Artificial Sequence
<220> FEATURE:
<223> OTHER INFORMATION: VL CDR-2 HB-20

<400> SEQUENCE: 82

Tyr Thr Ser
1

<210> SEQ ID NO 83
<211> LENGTH: 3
<212> TYPE: PRT
<213> ORGANISM: Artificial Sequence
<220> FEATURE:
<223> OTHER INFORMATION: VL CDR-2 HB-22

<400> SEQUENCE: 83

Lys Val Ser
1

<210> SEQ ID NO 84
<211> LENGTH: 9
<212> TYPE: PRT
<213> ORGANISM: Artificial Sequence
<220> FEATURE:
<223> OTHER INFORMATION: VL CDR-3 72A1

<400> SEQUENCE: 84

Val Leu Trp His Ser Asn His Trp Val
1               5

<210> SEQ ID NO 85
<211> LENGTH: 9
<212> TYPE: PRT
<213> ORGANISM: Artificial Sequence
<220> FEATURE:
<223> OTHER INFORMATION: VL CDR-3 HB-1

<400> SEQUENCE: 85

```
Gln Gln Tyr Asn Thr Tyr Pro Tyr Thr
1               5

<210> SEQ ID NO 86
<211> LENGTH: 9
<212> TYPE: PRT
<213> ORGANISM: Artificial Sequence
<220> FEATURE:
<223> OTHER INFORMATION: VL CDR-3 HB-2

<400> SEQUENCE: 86

Gln Gln Trp Ser Ser Asn Pro Pro Thr
1               5

<210> SEQ ID NO 87
<211> LENGTH: 9
<212> TYPE: PRT
<213> ORGANISM: Artificial Sequence
<220> FEATURE:
<223> OTHER INFORMATION: VL CDR-3 HB-3

<400> SEQUENCE: 87

Gln Gln Gly Asn Thr Leu Pro Pro Thr
1               5

<210> SEQ ID NO 88
<211> LENGTH: 10
<212> TYPE: PRT
<213> ORGANISM: Artificial Sequence
<220> FEATURE:
<223> OTHER INFORMATION: VL CDR-3 HB-5

<400> SEQUENCE: 88

Gln Gln Ser Asn Ser Trp Pro Met Leu Thr
1               5                   10

<210> SEQ ID NO 89
<211> LENGTH: 9
<212> TYPE: PRT
<213> ORGANISM: Artificial Sequence
<220> FEATURE:
<223> OTHER INFORMATION: VL CDR-3 HB-6

<400> SEQUENCE: 89

Gln Gln Trp Ser Ser Asn Pro Pro Thr
1               5

<210> SEQ ID NO 90
<211> LENGTH: 9
<212> TYPE: PRT
<213> ORGANISM: Artificial Sequence
<220> FEATURE:
<223> OTHER INFORMATION: VL CDR-3 HB-7

<400> SEQUENCE: 90

Gln Gln Tyr Ser Ser Tyr Pro Leu Thr
1               5

<210> SEQ ID NO 91
<211> LENGTH: 9
<212> TYPE: PRT
<213> ORGANISM: Artificial Sequence
<220> FEATURE:
<223> OTHER INFORMATION: VL CDR-3 HB-8

<400> SEQUENCE: 91

Phe Gln Gly Ser His Val Pro Tyr Thr
```

```
<210> SEQ ID NO 92
<211> LENGTH: 9
<212> TYPE: PRT
<213> ORGANISM: Artificial Sequence
<220> FEATURE:
<223> OTHER INFORMATION: VL CDR-3 HB-9

<400> SEQUENCE: 92

Phe Gln Gly Ser His Val Pro Tyr Thr
1               5

<210> SEQ ID NO 93
<211> LENGTH: 8
<212> TYPE: PRT
<213> ORGANISM: Artificial Sequence
<220> FEATURE:
<223> OTHER INFORMATION: VL CDR-3 HB-10

<400> SEQUENCE: 93

Gln Gln Asn Thr Leu Pro Pro Thr
1               5

<210> SEQ ID NO 94
<211> LENGTH: 10
<212> TYPE: PRT
<213> ORGANISM: Artificial Sequence
<220> FEATURE:
<223> OTHER INFORMATION: VL CDR-3 HB-11

<400> SEQUENCE: 94

Gln Gln Phe Thr Ser Ser Pro Ser Trp Thr
1               5                   10

<210> SEQ ID NO 95
<211> LENGTH: 9
<212> TYPE: PRT
<213> ORGANISM: Artificial Sequence
<220> FEATURE:
<223> OTHER INFORMATION: VL CDR-3 HB-12

<400> SEQUENCE: 95

Ser Gln Ser Thr His Val Pro Leu Thr
1               5

<210> SEQ ID NO 96
<211> LENGTH: 9
<212> TYPE: PRT
<213> ORGANISM: Artificial Sequence
<220> FEATURE:
<223> OTHER INFORMATION: VL CDR-3 HB-14

<400> SEQUENCE: 96

Phe Gln Gly Ser His Val Pro Pro Thr
1               5

<210> SEQ ID NO 97
<211> LENGTH: 9
<212> TYPE: PRT
<213> ORGANISM: Artificial Sequence
<220> FEATURE:
<223> OTHER INFORMATION: VL CDR-3 HB-17

<400> SEQUENCE: 97

Gln Gln Gly Asn Thr Leu Pro Pro Thr
1               5
```

<210> SEQ ID NO 98
<211> LENGTH: 9
<212> TYPE: PRT
<213> ORGANISM: Artificial Sequence
<220> FEATURE:
<223> OTHER INFORMATION: VL CDR-3 HB-20

<400> SEQUENCE: 98

Gln Gln Gly Asn Ala Leu Pro Pro Thr
1               5

<210> SEQ ID NO 99
<211> LENGTH: 9
<212> TYPE: PRT
<213> ORGANISM: Artificial Sequence
<220> FEATURE:
<223> OTHER INFORMATION: VL CDR-3 HB-22

<400> SEQUENCE: 99

Phe Gln Gly Ser His Val Pro Trp Thr
1               5

<210> SEQ ID NO 100
<211> LENGTH: 137
<212> TYPE: PRT
<213> ORGANISM: Artificial Sequence
<220> FEATURE:
<223> OTHER INFORMATION: heavy chain mAb 72A1

<400> SEQUENCE: 100

Pro Glu Leu Val Lys Pro Gly Thr Ser Met Lys Ile Ser Cys Lys Ala
1               5                   10                  15

Ser Gly Ser Ser Phe Thr Asp Tyr Thr Met Asn Trp Met Lys Gln Ser
                20                  25                  30

His Gly Lys Asn Leu Glu Trp Ile Gly Leu Ile Asn Pro Tyr Asn Gly
            35                  40                  45

Gly Thr Arg Tyr Asn Gln Lys Phe Lys Gly Lys Ala Thr Leu Thr Leu
        50                  55                  60

Asp Lys Ser Ser Ser Thr Ala Tyr Met Glu Val Leu Ser Leu Thr Ser
65                  70                  75                  80

Glu Asp Ser Ala Val Tyr Tyr Cys Ala Gly Gly Leu Arg Arg Val Asn
                85                  90                  95

Trp Phe Ala Tyr Trp Gly Gln Gly Thr Leu Val Ser Val Ser Ala Ala
            100                 105                 110

Lys Thr Thr Pro Pro Ser Val Tyr Pro Leu Ala Pro Gly Ser Ala Ala
        115                 120                 125

Gln Thr Asn Ser Met Val Thr Leu Gly
    130                 135

<210> SEQ ID NO 101
<211> LENGTH: 109
<212> TYPE: PRT
<213> ORGANISM: Artificial Sequence
<220> FEATURE:
<223> OTHER INFORMATION: light chain mAb 72A1

<400> SEQUENCE: 101

Gln Ala Val Leu Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

```
Asn Tyr Ala Asn Trp Val Gln Glu Lys Pro Asp His Leu Phe Thr Gly
            35                  40                  45

Leu Ile Gly Gly Thr Asn Asn Arg Val Pro Gly Val Pro Ala Arg Phe
         50                  55                  60

Ser Gly Ser Leu Ile Gly Asp Lys Ala Ala Leu Thr Ile Thr Gly Ala
 65              70                  75                  80

Gln Thr Glu Asp Glu Ala Ile Tyr Phe Cys Val Leu Trp His Ser Asn
                 85                  90                  95

His Trp Val Phe Gly Gly Gly Thr Lys Leu Thr Val Leu
                100                 105
```

<210> SEQ ID NO 102
<211> LENGTH: 138
<212> TYPE: PRT
<213> ORGANISM: Artificial Sequence
<220> FEATURE:
<223> OTHER INFORMATION: heavy chain mAb HB1

<400> SEQUENCE: 102

```
Pro Gly Leu Val Ala Pro Ser Gln Ser Leu Ser Ile Thr Cys Thr Val
 1               5                  10                  15

Ser Gly Phe Leu Leu Thr Thr Tyr Gly Val His Trp Val Arg Gln Pro
             20                  25                  30

Pro Gly Lys Gly Leu Glu Trp Leu Gly Val Ile Trp Ala Gly Gly Ser
         35                  40                  45

Thr Asn Tyr Asn Ser Ala Leu Met Ser Arg Leu Ser Ile Asn Lys Asp
 50                  55                  60

Ile Ser Lys Ser Gln Val Phe Leu Lys Met Asn Ser Leu Gln Thr Asp
65                  70                  75                  80

Asp Thr Ala Met Tyr Tyr Cys Thr Arg Asp Arg Gly Tyr Gly Tyr Leu
                 85                  90                  95

Tyr Ala Met Asp Tyr Trp Gly Gln Gly Thr Ser Val Thr Val Ser Ser
                100                 105                 110

Ala Lys Thr Thr Pro Pro Ser Val Tyr Pro Leu Ala Pro Gly Ser Ala
            115                 120                 125

Ala Gln Thr Asn Ser Met Val Thr Leu Gly
        130                 135
```

<210> SEQ ID NO 103
<211> LENGTH: 107
<212> TYPE: PRT
<213> ORGANISM: Artificial Sequence
<220> FEATURE:
<223> OTHER INFORMATION: light chain mAb HB1

<400> SEQUENCE: 103

```
Lys Phe Met Ser Thr Ser Val Gly Asp Arg Val Ser Val Thr Cys Lys
 1               5                  10                  15

Ala Ser Gln Asn Val Gly Thr Asn Val Ala Trp Tyr Gln Gln Lys Pro
             20                  25                  30

Gly Gln Ser Pro Lys Ala Leu Ile Tyr Ser Thr Ser Ser Arg Tyr Thr
         35                  40                  45

Gly Val Pro Asp Arg Phe Ala Gly Ser Gly Ser Gly Thr Asp Tyr Thr
     50                  55                  60

Leu Thr Ile Ser Asn Val Gln Ser Glu Asp Leu Ala Glu Tyr Phe Cys
65                  70                  75                  80

Gln Gln Tyr Asn Thr Tyr Pro Tyr Thr Phe Gly Gly Gly Thr Arg Leu
```

Asp Ile Lys Arg Ala Asp Ala Ala Pro Thr Val
                100                 105

<210> SEQ ID NO 104
<211> LENGTH: 134
<212> TYPE: PRT
<213> ORGANISM: Artificial Sequence
<220> FEATURE:
<223> OTHER INFORMATION: heavy chain mAb HB2

<400> SEQUENCE: 104

Pro Glu Leu Lys Lys Pro Gly Glu Thr Val Lys Ile Ser Cys Lys Ala
1               5                   10                  15

Ser Gly Tyr Thr Phe Thr Ala Tyr Ser Met His Trp Val Lys Leu Thr
            20                  25                  30

Pro Gly Lys Gly Leu Lys Trp Met Gly Trp Ile Asn Thr Lys Thr Gly
        35                  40                  45

Glu Pro Thr Tyr Ala Asp Asp Phe Lys Gly Arg Phe Ala Phe Ser Leu
    50                  55                  60

Glu Thr Ser Ala Ser Thr Ala Tyr Leu Gln Ile Asn Asn Leu Lys Asn
65                  70                  75                  80

Glu Asp Thr Ala Thr Tyr Phe Cys Ala Pro Tyr Gly Tyr Ala Leu Asp
                85                  90                  95

Tyr Trp Gly Gln Gly Thr Ser Val Thr Val Ser Ser Ala Lys Thr Thr
            100                 105                 110

Pro Pro Ser Val Tyr Pro Leu Ala Pro Gly Ser Ala Ala Gln Thr Asn
        115                 120                 125

Ser Met Val Thr Leu Gly
        130

<210> SEQ ID NO 105
<211> LENGTH: 106
<212> TYPE: PRT
<213> ORGANISM: Artificial Sequence
<220> FEATURE:
<223> OTHER INFORMATION: light chain mAb HB2

<400> SEQUENCE: 105

Ala Ile Leu Ser Ala Ser Pro Gly Glu Lys Val Thr Met Thr Cys Arg
1               5                   10                  15

Ala Thr Ser Ser Val Asn Tyr Met His Trp Tyr Gln Gln Lys Pro Gly
            20                  25                  30

Ser Ser Pro Lys Pro Trp Ile Tyr Ala Thr Ser Asn Leu Ala Ser Gly
        35                  40                  45

Val Pro Ala Arg Phe Ser Gly Ser Gly Ser Gly Thr Ser Tyr Ser Leu
    50                  55                  60

Thr Ile Ser Arg Val Glu Ala Glu Asp Ala Ala Thr Tyr Tyr Cys Gln
65                  70                  75                  80

Gln Trp Ser Ser Asn Pro Pro Thr Phe Gly Ala Gly Thr Lys Leu Glu
                85                  90                  95

Leu Lys Arg Ala Asp Ala Ala Pro Thr Val
            100                 105

<210> SEQ ID NO 106
<211> LENGTH: 137
<212> TYPE: PRT
<213> ORGANISM: Artificial Sequence
<220> FEATURE:

<223> OTHER INFORMATION: heavy chain mAb HB3

<400> SEQUENCE: 106

Ala Glu Leu Val Arg Pro Gly Ala Ser Val Lys Leu Ser Cys Lys Ala
1               5                   10                  15

Ser Gly Tyr Thr Phe Ala Ser Tyr Trp Met Gln Trp Val Lys Gln Trp
            20                  25                  30

Pro Gly Gln Gly Leu Glu Trp Ile Gly Glu Ile Asn Pro Asn Asn Gly
        35                  40                  45

His Thr Asn Tyr Asn Glu Arg Phe Lys Asn Lys Ala Ser Leu Thr Val
    50                  55                  60

Asp Lys Ser Ser Ser Thr Ala Tyr Met Gln Leu Ser Ser Leu Thr Ser
65                  70                  75                  80

Glu Asp Ser Ala Val Tyr Tyr Cys Ala Arg Asn Leu Tyr Tyr Tyr Gly
                85                  90                  95

Arg Pro Asp Tyr Trp Gly Gln Gly Thr Ser Val Thr Val Ser Ser Ala
            100                 105                 110

Lys Thr Thr Ala Pro Ser Val Tyr Pro Leu Ala Pro Val Cys Gly Asp
        115                 120                 125

Thr Thr Gly Ser Ser Val Thr Leu Gly
    130                 135

<210> SEQ ID NO 107
<211> LENGTH: 107
<212> TYPE: PRT
<213> ORGANISM: Artificial Sequence
<220> FEATURE:
<223> OTHER INFORMATION: light chain mAb HB3

<400> SEQUENCE: 107

Ser Ser Leu Ser Ala Ser Leu Gly Asp Arg Val Thr Ile Ser Cys Arg
1               5                   10                  15

Ala Ser Gln Asp Ile Gly Asn Tyr Leu Asn Trp Tyr Gln Gln Lys Pro
            20                  25                  30

Asp Gly Thr Ile Lys Leu Leu Ile Tyr Tyr Thr Ser Arg Leu His Ser
        35                  40                  45

Gly Val Pro Ser Arg Phe Ser Gly Ser Gly Ser Gly Thr Asp Tyr Ser
    50                  55                  60

Leu Thr Ile Ser Asn Leu Glu Glu Glu Asp Ile Ala Thr Tyr Phe Cys
65                  70                  75                  80

Gln Gln Gly Asn Thr Leu Pro Pro Thr Phe Gly Gly Gly Thr Lys Leu
                85                  90                  95

Glu Ile Lys Arg Ala Asp Ala Ala Pro Thr Val
            100                 105

<210> SEQ ID NO 108
<211> LENGTH: 140
<212> TYPE: PRT
<213> ORGANISM: Artificial Sequence
<220> FEATURE:
<223> OTHER INFORMATION: heavy chain mAb HB5

<400> SEQUENCE: 108

Ala Glu Leu Val Arg Pro Gly Ala Ser Val Lys Ile Ser Cys Lys Ala
1               5                   10                  15

Phe Gly Tyr Thr Phe Thr Asn His Asn Ile Asn Trp Val Lys Gln Arg
            20                  25                  30

Pro Gly Gln Gly Leu Asp Trp Ile Gly Tyr Ile Asn Pro Tyr Asn Asp

```
                    35                  40                  45
Tyr Thr Ser Tyr Asn Gln Lys Phe Lys Gly Lys Ala Thr Leu Thr Val
            50                  55                  60

Asp Lys Ser Ser Asn Thr Ala Tyr Met Glu Leu Ser Ser Leu Thr Ser
 65                 70                  75                  80

Glu Asp Ser Ala Val Tyr Tyr Cys Ala Arg Ser Glu Gly Trp Leu Arg
                85                  90                  95

Arg Gly Ala Trp Phe Ala Tyr Trp Gly Gln Gly Thr Leu Val Thr Val
            100                 105                 110

Ser Ala Ala Lys Thr Thr Ala Pro Ser Val Tyr Pro Leu Ala Pro Val
            115                 120                 125

Cys Gly Asp Thr Thr Gly Ser Ser Val Thr Leu Gly
            130                 135                 140

<210> SEQ ID NO 109
<211> LENGTH: 108
<212> TYPE: PRT
<213> ORGANISM: Artificial Sequence
<220> FEATURE:
<223> OTHER INFORMATION: light chain mAb HB5

<400> SEQUENCE: 109

Ala Ile Leu Ser Val Ser Pro Gly Glu Arg Val Ser Phe Ser Cys Arg
 1               5                  10                  15

Ala Ser Gln Ser Ile Gly Thr Ser Ile His Trp Tyr Gln Gln Arg Thr
                20                  25                  30

Asn Asp Ser Pro Arg Leu Leu Ile Lys Tyr Ala Ser Glu Ser Ile Ser
            35                  40                  45

Gly Ile Pro Pro Arg Phe Ser Gly Ser Gly Ser Gly Thr Asp Phe Thr
        50                  55                  60

Leu Ser Ile Asn Ser Val Glu Ser Glu Asp Ile Ala Asp Tyr His Cys
 65                 70                  75                  80

Gln Gln Ser Asn Ser Trp Pro Met Leu Thr Phe Gly Ala Gly Thr Lys
                85                  90                  95

Leu Glu Leu Lys Arg Ala Asp Ala Ala Pro Thr Val
            100                 105

<210> SEQ ID NO 110
<211> LENGTH: 134
<212> TYPE: PRT
<213> ORGANISM: Artificial Sequence
<220> FEATURE:
<223> OTHER INFORMATION: heavy chain mAb HB6

<400> SEQUENCE: 110

Pro Glu Leu Arg Lys Pro Gly Glu Thr Val Lys Ile Ser Cys Lys Ala
 1               5                  10                  15

Ser Gly Tyr Thr Phe Thr Asp Tyr Ser Met His Trp Val Lys Gln Thr
                20                  25                  30

Pro Gly Lys Gly Leu Lys Trp Met Gly Trp Ile Asn Thr Arg Thr Gly
            35                  40                  45

Glu Pro Arg Tyr Ala Asp Asp Phe Lys Gly Arg Phe Ala Phe Ser Leu
        50                  55                  60

Glu Thr Ser Ala Ser Thr Ala Tyr Leu Gln Ile Asn Asn Leu Lys Asn
 65                 70                  75                  80

Glu Asp Thr Ala Thr Tyr Phe Cys Ala Pro Tyr Gly Tyr Ala Leu Asp
                85                  90                  95
```

```
Tyr Trp Gly Gln Gly Thr Ser Val Thr Val Ser Ser Ala Lys Thr Thr
                100                 105                 110

Pro Pro Ser Val Tyr Pro Leu Ala Pro Gly Ser Ala Ala Gln Thr Asn
            115                 120                 125

Ser Met Val Thr Leu Gly
        130

<210> SEQ ID NO 111
<211> LENGTH: 106
<212> TYPE: PRT
<213> ORGANISM: Artificial Sequence
<220> FEATURE:
<223> OTHER INFORMATION: light chain mAb HB6

<400> SEQUENCE: 111

Ala Ile Leu Ser Ala Ser Pro Gly Glu Lys Val Thr Met Thr Cys Arg
1               5                   10                  15

Ala Thr Ser Ser Val Asn Tyr Met His Trp Tyr Gln Gln Lys Pro Gly
            20                  25                  30

Ser Ser Pro Lys Pro Trp Ile Tyr Ala Thr Ser Asn Leu Ala Ser Gly
        35                  40                  45

Val Pro Ala Arg Phe Ser Gly Ser Gly Ser Gly Thr Ser Tyr Ser Leu
    50                  55                  60

Thr Ile Ser Arg Val Glu Ala Glu Asp Ala Ala Thr Tyr Tyr Cys Gln
65                  70                  75                  80

Gln Trp Ser Ser Asn Pro Pro Thr Phe Gly Ala Gly Thr Lys Leu Glu
                85                  90                  95

Leu Lys Arg Ala Asp Ala Ala Pro Thr Val
            100                 105

<210> SEQ ID NO 112
<211> LENGTH: 136
<212> TYPE: PRT
<213> ORGANISM: Artificial Sequence
<220> FEATURE:
<223> OTHER INFORMATION: heavy chain mAb HB7

<400> SEQUENCE: 112

Ala Glu Leu Val Arg Pro Gly Ala Ser Val Lys Leu Ser Cys Lys Ala
1               5                   10                  15

Leu Gly Tyr Thr Phe Thr Asp Tyr Glu Met His Trp Val Lys Gln Thr
            20                  25                  30

Pro Val His Gly Leu Glu Trp Ile Gly Thr Ile Ser Pro Gly Arg Ser
        35                  40                  45

Gly Thr Ala Tyr Asn Gln Lys Phe Lys Gly Lys Ala Thr Leu Thr Ala
    50                  55                  60

Asp Lys Ser Ser Arg Thr Ala Tyr Met Glu Leu Asn Ser Leu Thr Ser
65                  70                  75                  80

Glu Asp Ser Ala Val Tyr Tyr Cys Ser Arg Tyr Gly His Pro Ser Tyr
                85                  90                  95

Leu Asp Val Trp Gly Ala Gly Thr Thr Val Thr Val Ser Ser Ala Lys
            100                 105                 110

Thr Thr Pro Pro Ser Val Tyr Pro Leu Ala Pro Gly Ser Ala Ala Gln
            115                 120                 125

Thr Asn Ser Met Val Thr Leu Gly
        130                 135

<210> SEQ ID NO 113
```

```
<211> LENGTH: 107
<212> TYPE: PRT
<213> ORGANISM: Artificial Sequence
<220> FEATURE:
<223> OTHER INFORMATION: light chain mAb HB7

<400> SEQUENCE: 113

Lys Phe Met Ser Thr Ser Val Gly Asp Arg Val Asn Ile Thr Cys Lys
1               5                   10                  15

Ala Ser Gln Ser Val Gly Asn Ala Val Ala Trp Phe Gln Gln Lys Pro
            20                  25                  30

Gly Gln Ser Pro Lys Leu Leu Ile Tyr Ser Ala Ser Asn Arg Tyr Thr
        35                  40                  45

Gly Ile Pro Asp Arg Phe Thr Gly Ser Gly Ser Gly Thr Asp Phe Thr
    50                  55                  60

Leu Thr Cys Asn Asn Met Gln Ser Glu Asp Leu Ala Asp Tyr Phe Cys
65                  70                  75                  80

Gln Gln Tyr Ser Ser Tyr Pro Leu Thr Phe Gly Ala Gly Thr Lys Leu
                85                  90                  95

Glu Leu Lys Arg Ala Asp Ala Ala Pro Thr Val
            100                 105

<210> SEQ ID NO 114
<211> LENGTH: 140
<212> TYPE: PRT
<213> ORGANISM: Artificial Sequence
<220> FEATURE:
<223> OTHER INFORMATION: heavy chain mAb HB8

<400> SEQUENCE: 114

Pro Glu Leu Lys Lys Pro Gly Glu Thr Val Lys Ile Ser Cys Lys Ala
1               5                   10                  15

Ser Gly Tyr Ser Phe Thr Asn Tyr Gly Met Asn Trp Val Lys Gln Ala
            20                  25                  30

Pro Gly Lys Gly Leu Lys Trp Met Gly Trp Ile Asn Thr Tyr Thr Gly
        35                  40                  45

Glu Pro Thr Tyr Ala Asp Asp Phe Lys Gly Arg Phe Ala Phe Ser Leu
    50                  55                  60

Glu Thr Ser Ala Ser Thr Ala Phe Leu Gln Ile Asn Asn Leu Lys Asn
65                  70                  75                  80

Glu Asp Thr Ala Thr Tyr Leu Cys Ala Arg Tyr Tyr Gly Ser Val
                85                  90                  95

Tyr Ser Ala Trp Phe Ala Tyr Trp Gly Gln Gly Thr Leu Val Thr Val
            100                 105                 110

Ser Ala Ala Lys Thr Thr Pro Pro Ser Val Tyr Pro Leu Ala Pro Gly
        115                 120                 125

Ser Ala Ala Gln Thr Asn Ser Met Val Thr Leu Gly
    130                 135                 140

<210> SEQ ID NO 115
<211> LENGTH: 112
<212> TYPE: PRT
<213> ORGANISM: Artificial Sequence
<220> FEATURE:
<223> OTHER INFORMATION: light chain mAb HB8

<400> SEQUENCE: 115

Leu Ser Leu Pro Val Ser Leu Gly Asp Gln Ala Ser Ile Ser Cys Arg
1               5                   10                  15
```

```
Ser Ser Gln Ser Ile Val His Ser Asn Gly Asn Thr Tyr Leu Glu Trp
            20                  25                  30

Tyr Leu Gln Lys Ala Gly Gln Ser Pro Lys Leu Leu Ile Tyr Lys Val
                35                  40                  45

Ser Asn Arg Phe Ser Gly Val Pro Asp Arg Phe Gly Gly Ser Gly Ser
         50                  55                  60

Gly Thr Asp Phe Thr Leu Lys Ile Ser Arg Val Glu Ala Glu Asp Leu
 65                  70                  75                  80

Gly Val Tyr Tyr Cys Phe Gln Gly Ser His Val Pro Tyr Thr Phe Gly
                 85                  90                  95

Gly Gly Thr Lys Leu Glu Ile Lys Arg Ala Asp Ala Ala Pro Thr Val
            100                 105                 110

<210> SEQ ID NO 116
<211> LENGTH: 141
<212> TYPE: PRT
<213> ORGANISM: Artificial Sequence
<220> FEATURE:
<223> OTHER INFORMATION: heavy chain mAb HB9

<400> SEQUENCE: 116

Gly Gly Leu Val Lys Pro Gly Gly Ser Leu Lys Leu Ser Cys Ala Ala
 1               5                  10                  15

Ser Gly Phe Thr Phe Ser Ser Tyr Thr Met Ser Trp Val Arg Gln Thr
            20                  25                  30

Pro Glu Lys Arg Leu Glu Trp Val Ala Thr Ile Ser Ser Gly Gly Ser
                35                  40                  45

Tyr Ile Tyr Tyr Pro Asp Ser Val Lys Gly Arg Phe Thr Ile Ser Arg
         50                  55                  60

Asp Asn Ala Lys Asn Thr Leu Tyr Leu Gln Met Ser Ser Leu Lys Ser
 65                  70                  75                  80

Glu Asp Thr Ala Ile Tyr Tyr Cys Thr Arg Glu Asp Phe Tyr Tyr Gly
                 85                  90                  95

Ser Ser Tyr Gly Phe Phe Asp Val Trp Gly Ala Gly Thr Thr Val Thr
            100                 105                 110

Val Ser Ser Ala Lys Thr Thr Ala Pro Ser Val Tyr Pro Leu Ala Pro
                115                 120                 125

Val Cys Gly Asp Thr Thr Gly Ser Ser Val Thr Leu Gly
            130                 135                 140

<210> SEQ ID NO 117
<211> LENGTH: 112
<212> TYPE: PRT
<213> ORGANISM: Artificial Sequence
<220> FEATURE:
<223> OTHER INFORMATION: light chain mAb HB9

<400> SEQUENCE: 117

Leu Ser Leu Pro Val Ser Leu Gly Asp Gln Ala Ser Ile Ser Cys Arg
 1               5                  10                  15

Ser Ser Gln Ser Ile Val His Ser Asn Gly Asn Thr Tyr Leu Glu Trp
            20                  25                  30

Tyr Leu Gln Lys Ala Gly Gln Ser Pro Lys Leu Leu Ile Tyr Lys Val
                35                  40                  45

Ser Asn Arg Phe Ser Gly Val Pro Asp Arg Phe Gly Gly Ser Gly Ser
         50                  55                  60

Gly Thr Asp Phe Thr Leu Lys Ile Ser Arg Val Glu Ala Glu Asp Leu
 65                  70                  75                  80
```

Gly Val Tyr Tyr Cys Phe Gln Gly Ser His Val Pro Tyr Thr Phe Gly
                85                  90                  95

Gly Gly Thr Lys Leu Glu Ile Lys Arg Ala Asp Ala Ala Pro Thr Val
            100                 105                 110

<210> SEQ ID NO 118
<211> LENGTH: 112
<212> TYPE: PRT
<213> ORGANISM: Artificial Sequence
<220> FEATURE:
<223> OTHER INFORMATION: heavy chain mAb HB10

<400> SEQUENCE: 118

Leu Ser Leu Pro Val Ser Leu Gly Asp Gln Ala Ser Ile Ser Cys Arg
1               5                   10                  15

Ser Ser Gln Ser Ile Val His Ser Asn Gly Asn Thr Tyr Leu Glu Trp
            20                  25                  30

Tyr Leu Gln Lys Ala Gly Gln Ser Pro Lys Leu Leu Ile Tyr Lys Val
        35                  40                  45

Ser Asn Arg Phe Ser Gly Val Pro Asp Arg Phe Gly Gly Ser Gly Ser
    50                  55                  60

Gly Thr Asp Phe Thr Leu Lys Ile Ser Arg Val Glu Ala Glu Asp Leu
65                  70                  75                  80

Gly Val Tyr Tyr Cys Phe Gln Gly Ser His Val Pro Tyr Thr Phe Gly
                85                  90                  95

Gly Gly Thr Lys Leu Glu Ile Lys Arg Ala Asp Ala Ala Pro Thr Val
            100                 105                 110

<210> SEQ ID NO 119
<211> LENGTH: 107
<212> TYPE: PRT
<213> ORGANISM: Artificial Sequence
<220> FEATURE:
<223> OTHER INFORMATION: light chain mAb HB10

<400> SEQUENCE: 119

Ser Ser Leu Ser Ala Ser Leu Gly Asp Arg Val Thr Ile Ser Cys Arg
1               5                   10                  15

Ala Ser Gln Asp Ile Gly Asn Tyr Leu Asn Trp Tyr Gln Gln Lys Pro
            20                  25                  30

Asp Gly Thr Val Lys Leu Leu Ile Tyr Tyr Thr Ser Arg Leu His Ser
        35                  40                  45

Gly Val Pro Ser Arg Phe Ser Gly Ser Gly Ser Gly Thr Asp Tyr Ser
    50                  55                  60

Leu Thr Ile Ser Asn Leu Glu Glu Asp Ile Ala Thr Tyr Phe Cys
65                  70                  75                  80

Gln Gln Gly Asn Thr Leu Pro Pro Thr Phe Gly Gly Gly Thr Lys Leu
                85                  90                  95

Glu Ile Lys Arg Ala Asp Ala Ala Pro Thr Val
            100                 105

<210> SEQ ID NO 120
<211> LENGTH: 138
<212> TYPE: PRT
<213> ORGANISM: Artificial Sequence
<220> FEATURE:
<223> OTHER INFORMATION: heavy chain mAb HB11

<400> SEQUENCE: 120

Pro Ser Leu Val Lys Pro Ser Gln Thr Leu Ser Leu Thr Cys Ser Val
1               5                   10                  15

Thr Gly Asp Ser Ile Thr Ser Gly Phe Trp Asn Trp Ile Arg Lys Phe
            20                  25                  30

Pro Gly Asn Lys Leu Glu Tyr Met Gly Tyr Ile Ser Tyr Ser Gly Ser
        35                  40                  45

Thr Tyr Tyr Asn Pro Ser Leu Lys Ser Arg Ile Ser Ile Thr Arg Asp
    50                  55                  60

Thr Ser Lys Asn Gln Tyr Tyr Leu Gln Leu Asn Ser Val Thr Thr Glu
65                  70                  75                  80

Asp Thr Ala Thr Tyr Tyr Cys Ala Arg Gly Asn Gly Gly Asn Tyr Asp
                85                  90                  95

Trp Tyr Phe Asp Val Trp Gly Ala Gly Thr Thr Val Thr Val Ser Ser
            100                 105                 110

Ala Lys Thr Thr Pro Pro Ser Val Tyr Pro Leu Ala Pro Gly Ser Ala
            115                 120                 125

Ala Gln Thr Asn Ser Met Val Thr Leu Gly
        130                 135

<210> SEQ ID NO 121
<211> LENGTH: 107
<212> TYPE: PRT
<213> ORGANISM: Artificial Sequence
<220> FEATURE:
<223> OTHER INFORMATION: light chain mAb HB11

<400> SEQUENCE: 121

Ala Ile Met Ser Ala Ser Leu Gly Glu Lys Val Thr Met Ser Cys Arg
1               5                   10                  15

Ala Ser Ser Ser Val Asn Phe Met Asn Trp Tyr Gln Gln Lys Ser Asp
            20                  25                  30

Asp Ser Pro Lys Leu Leu Ile Tyr Tyr Ile Ser Asn Leu Ala Pro Gly
        35                  40                  45

Val Pro Ala Arg Phe Ser Gly Ser Gly Ser Gly Asn Ser Tyr Ser Leu
    50                  55                  60

Thr Ile Ser Gly Met Glu Gly Glu Asp Ala Ala Thr Tyr Tyr Cys Gln
65                  70                  75                  80

Gln Phe Thr Ser Ser Pro Ser Trp Thr Phe Gly Gly Gly Thr Lys Leu
                85                  90                  95

Glu Ile Lys Arg Ala Asp Ala Ala Pro Thr Val
            100                 105

<210> SEQ ID NO 122
<211> LENGTH: 111
<212> TYPE: PRT
<213> ORGANISM: Artificial Sequence
<220> FEATURE:
<223> OTHER INFORMATION: heavy chain mAb HB12

<400> SEQUENCE: 122

Ala Glu Leu Val Arg Pro Gly Ala Ser Val Lys Leu Ser Cys Lys Ala
1               5                   10                  15

Ser Gly Tyr Thr Phe Thr Asn Tyr Trp Ile His Trp Val Lys Gln Trp
            20                  25                  30

Pro Gly Gln Gly Leu Glu Trp Ile Gly Glu Ile Asn Pro Asn Asn Gly
        35                  40                  45

His Thr Asn Tyr Asn Glu Arg Phe Lys Asn Lys Ala Ser Leu Thr Val
    50                  55                  60

```
Asp Lys Ser Ser Ser Thr Ala Tyr Met Gln Leu Ser Ser Leu Thr Ser
 65                  70                  75                  80

Glu Asp Ser Ala Val Tyr Tyr Cys Ala Arg Asn Leu Tyr Tyr Tyr Gly
             85                  90                  95

Arg Pro Asp Tyr Trp Gly Gln Gly Thr Ser Val Thr Val Ser Ser
        100                 105                 110

<210> SEQ ID NO 123
<211> LENGTH: 104
<212> TYPE: PRT
<213> ORGANISM: Artificial Sequence
<220> FEATURE:
<223> OTHER INFORMATION: light chain mAb HB12

<400> SEQUENCE: 123

Leu Ser Leu Pro Val Ser Leu Gly Asp Gln Ala Ser Ile Ser Cys Arg
 1               5                  10                  15

Ser Ser Gln Ser Leu Val His Ser Asn Gly Asn Thr Tyr Leu His Trp
             20                  25                  30

Tyr Leu Gln Lys Pro Gly Gln Ser Pro Lys Leu Leu Ile Tyr Lys Val
         35                  40                  45

Ser Asn Arg Phe Ser Gly Val Pro Asp Arg Phe Ser Gly Ser Gly Ser
 50                  55                  60

Gly Thr Asp Phe Thr Leu Lys Ile Ser Arg Val Glu Ala Glu Asp Leu
 65                  70                  75                  80

Gly Val Tyr Phe Cys Ser Gln Ser Thr His Val Pro Leu Thr Phe Gly
             85                  90                  95

Ser Gly Thr Lys Leu Glu Ile Lys
        100

<210> SEQ ID NO 124
<211> LENGTH: 112
<212> TYPE: PRT
<213> ORGANISM: Artificial Sequence
<220> FEATURE:
<223> OTHER INFORMATION: heavy chain mAb HB14

<400> SEQUENCE: 124

Ser Gly Ala Glu Leu Val Arg Pro Gly Ala Ser Val Asn Leu Ser Cys
 1               5                  10                  15

Lys Ala Leu Gly Tyr Thr Phe Thr Asp Tyr Glu Met His Trp Val Lys
             20                  25                  30

Gln Thr Pro Val Tyr Gly Leu Glu Trp Ile Gly Thr Ile His Pro Arg
         35                  40                  45

Arg Gly Gly Thr Ala Tyr Asn Gln Arg Phe Lys Gly Lys Ala Ala Leu
 50                  55                  60

Thr Ala Asp Lys Ser Ser Ser Thr Ala Tyr Met Glu Leu Ser Ser Leu
 65                  70                  75                  80

Thr Ser Glu Asp Ser Ala Val Tyr Cys Ala Arg Tyr Gly Tyr Pro
             85                  90                  95

Trp Tyr Phe Asp Val Trp Gly Ala Gly Thr Thr Val Thr Val Ser Ser
        100                 105                 110

<210> SEQ ID NO 125
<211> LENGTH: 104
<212> TYPE: PRT
<213> ORGANISM: Artificial Sequence
<220> FEATURE:
<223> OTHER INFORMATION: light chain mAb HB14
```

<400> SEQUENCE: 125

Leu Ser Leu Pro Val Ser Leu Gly Asp Gln Ala Ser Ile Ser Cys Arg
1               5                   10                  15

Ser Ser Gln Ser Ile Val His Asp Asn Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Leu Asp Lys Phe Ser Gly Ser Gly Ser
50                  55                  60

Gly Thr Asp Phe Thr Leu Lys Ile Ser Arg Val Glu Ala Glu Asp Leu
65                  70                  75                  80

Gly Ile Tyr Tyr Cys Phe Gln Gly Ser His Val Pro Pro Thr Phe Gly
                85                  90                  95

Gly Gly Thr Lys Leu Glu Ile Lys
            100

<210> SEQ ID NO 126
<211> LENGTH: 137
<212> TYPE: PRT
<213> ORGANISM: Artificial Sequence
<220> FEATURE:
<223> OTHER INFORMATION: heavy chain mAb HB17

<400> SEQUENCE: 126

Ala Glu Leu Val Ile Pro Gly Ala Ser Val Lys Val Ser Cys Lys Ala
1               5                   10                  15

Ser Gly Tyr Thr Phe Thr Ser Tyr Trp Ile His Trp Val Lys Gln Trp
            20                  25                  30

Pro Gly Gln Gly Leu Glu Trp Ile Gly Glu Ile Asn Pro Asn Asn Gly
        35                  40                  45

His Thr Asn Tyr Asn Glu Lys Phe Lys Ser Lys Ala Thr Leu Thr Val
50                  55                  60

Asp Lys Ser Ser Ser Thr Ala Tyr Met Gln Leu Ser Ser Leu Thr Ser
65                  70                  75                  80

Glu Asp Ser Ala Val Tyr Tyr Cys Ala Arg Asn Leu Phe Tyr Tyr Ser
                85                  90                  95

Arg Pro Asp Tyr Trp Gly Gln Gly Thr Ser Val Thr Val Ser Ser Ala
            100                 105                 110

Lys Thr Thr Pro Pro Ser Val Tyr Pro Leu Ala Pro Gly Cys Gly Asp
        115                 120                 125

Thr Thr Gly Ser Ser Val Thr Leu Gly
            130                 135

<210> SEQ ID NO 127
<211> LENGTH: 107
<212> TYPE: PRT
<213> ORGANISM: Artificial Sequence
<220> FEATURE:
<223> OTHER INFORMATION: light chain mAb HB17

<400> SEQUENCE: 127

Ser Ser Leu Ser Ala Ser Leu Gly Asp Arg Val Thr Ile Ser Cys Arg
1               5                   10                  15

Ala Ser Gln Asp Ile Gly Asn Tyr Leu Asn Trp Tyr Gln Gln Lys Pro
            20                  25                  30

Asp Gly Thr Ile Lys Leu Leu Ile Tyr Tyr Thr Ser Arg Leu His Ser
        35                  40                  45

Gly Val Pro Ser Arg Phe Ser Gly Ser Gly Thr Asp Tyr Ser
            50                  55                  60

Leu Thr Ile Ser Asn Leu Glu Glu Glu Asp Ile Ala Thr Tyr Phe Cys
 65                  70                  75                  80

Gln Gln Gly Asn Thr Leu Pro Pro Thr Phe Gly Gly Gly Thr Lys Leu
                85                  90                  95

Glu Ile Lys Arg Ala Asp Ala Ala Pro Thr Val
            100                 105

<210> SEQ ID NO 128
<211> LENGTH: 136
<212> TYPE: PRT
<213> ORGANISM: Artificial Sequence
<220> FEATURE:
<223> OTHER INFORMATION: heavy chain mAb HB20

<400> SEQUENCE: 128

Glu Leu Val Lys Pro Gly Ala Ser Val Lys Leu Ser Cys Lys Ala Ser
 1               5                  10                  15

Gly Tyr Thr Phe Thr Ser Tyr Trp Ile Gln Trp Val Lys Gln Arg Pro
                20                  25                  30

Gly Gln Gly Leu Glu Trp Ile Gly Glu Ile Asn Pro Thr Asn Gly His
            35                  40                  45

Thr Asn Tyr Asn Glu Lys Phe Lys Thr Lys Ala Thr Leu Thr Val Asp
 50                  55                  60

Lys Ser Ser Ser Thr Ala Tyr Met Arg Leu Ser Ser Leu Thr Ser Glu
 65                  70                  75                  80

Asp Ser Ala Val Tyr Tyr Cys Ala Arg Asn Leu Tyr Tyr Gly Arg
                85                  90                  95

Pro Asp Tyr Trp Gly Gln Gly Thr Ser Val Thr Val Ser Ser Ala Lys
                100                 105                 110

Thr Thr Ala Pro Ser Val Tyr Pro Leu Ala Pro Val Cys Gly Asp Thr
            115                 120                 125

Thr Gly Ser Ser Val Thr Leu Gly
            130                 135

<210> SEQ ID NO 129
<211> LENGTH: 107
<212> TYPE: PRT
<213> ORGANISM: Artificial Sequence
<220> FEATURE:
<223> OTHER INFORMATION: light chain mAb HB20

<400> SEQUENCE: 129

Ser Ser Leu Ser Ala Ser Leu Gly Asp Arg Val Thr Ile Ser Cys Arg
 1               5                  10                  15

Ala Ser Gln Asp Ile Gly Asn Tyr Leu Asn Trp Tyr Gln Gln Lys Pro
                20                  25                  30

Asp Gly Thr Val Lys Leu Leu Ile Tyr Tyr Thr Ser Arg Leu His Ser
            35                  40                  45

Gly Val Pro Ser Arg Phe Ser Gly Ser Gly Ser Gly Thr Asp Tyr Ser
            50                  55                  60

Leu Thr Ile Ser Asn Leu Glu Gln Glu Asp Ile Ala Thr Tyr Phe Cys
 65                  70                  75                  80

Gln Gln Gly Asn Ala Leu Pro Pro Thr Phe Gly Gly Gly Thr Lys Leu
                85                  90                  95

Glu Ile Lys Arg Ala Asp Ala Ala Pro Thr Val
            100                 105

<210> SEQ ID NO 130
<211> LENGTH: 139
<212> TYPE: PRT
<213> ORGANISM: Artificial Sequence
<220> FEATURE:
<223> OTHER INFORMATION: heavy chain mAb HB22

<400> SEQUENCE: 130

```
Pro Gly Leu Val Ala Pro Ser Gln Ser Leu Ser Ile Thr Cys Thr Val
1               5                   10                  15

Ser Gly Phe Ser Leu Thr Asn Tyr Gly Ile His Trp Val Arg Gln Pro
            20                  25                  30

Pro Gly Lys Gly Leu Glu Trp Leu Val Val Ile Trp Ser Asp Gly Ser
        35                  40                  45

Thr Ile Tyr Asn Ser Ala Leu Lys Ser Arg Leu Ser Ile Ser Lys Asp
    50                  55                  60

Asn Ser Lys Ser Gln Val Phe Leu Lys Met Asn Ser Leu Gln Thr Asp
65                  70                  75                  80

Asp Thr Ala Met Tyr Tyr Cys Ala Arg Asn Tyr Tyr Gly Asn Ser Tyr
                85                  90                  95

Pro Ala Trp Phe Ala Tyr Trp Gly Gln Gly Thr Leu Val Thr Val Ser
            100                 105                 110

Ala Ala Lys Thr Thr Pro Pro Ser Val Tyr Pro Leu Ala Pro Gly Ser
        115                 120                 125

Ala Ala Gln Thr Asn Ser Met Val Thr Leu Gly
    130                 135
```

<210> SEQ ID NO 131
<211> LENGTH: 112
<212> TYPE: PRT
<213> ORGANISM: Artificial Sequence
<220> FEATURE:
<223> OTHER INFORMATION: light chain mAb HB22

<400> SEQUENCE: 131

```
Leu Ser Leu Pro Val Ser Leu Gly Asp Gln Ala Ser Ile Ser Cys Arg
1               5                   10                  15

Ser Ser Gln Ser Ile Val His Ser Asn Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Arg Ile Ser Arg Val Glu Ala Glu Asp Leu
65                  70                  75                  80

Gly Val Tyr Tyr Cys Phe Gln Gly Ser His Val Pro Trp Thr Phe Gly
                85                  90                  95

Gly Gly Thr Lys Leu Glu Ile Lys Arg Ala Asp Ala Ala Pro Thr Val
            100                 105                 110
```

EPSTEIN-BARR VIRUS ANTIBODIES AND USES THEREOF

PRIORITY CLAIM

The present invention claims the benefit of U.S. Provisional Patent Application No. 62/491,945, entitled "EPSTEIN-BARR VIRUS ANTIBODIES AND USES THEREOF," filed Apr. 28, 2017, the content of which is incorporated herein by reference in its entirety.

STATEMENT OF GOVERNMENT INTEREST

The present invention was made with government support under Grant No. R21CA205106, awarded by U.S. Public Health Service. The Government has certain rights in the invention.

BACKGROUND

Epstein-Barr virus (EBV) infection is the causal agent of acute infectious mononucleosis (62, 63). Persistent EBV infection in immunodeficient individuals is associated with numerous epithelial and lymphoid malignancies, such as nasopharyngeal carcinoma, gastric carcinoma, Burkitt lymphoma, Hodgkin lymphoma, and post-transplant lymphoproliferative diseases (PTLD) (1). Transplantation is the treatment of choice for a variety of patients with end-stage organ failure or hematologic malignancies, or in need of reconstructive transplantation (1). Transplantation success depends entirely on potent immunosuppressive drugs to prevent stem cell/organ rejection. However, these drugs impose several serious side effects, including an increased risk of infection with or reactivation of Epstein-Barr virus (EBV), and the resultant development of PTLDs, which are aggressive, life-threatening complications (2, 3). Through the early 2000s, PTLD patients who had been EBV-naïve prior to transplantation showed mortality rates of 50-90% for stem cell and solid organ transplants; while recent data suggest outcomes have improved, challenges remain. PTLDs usually develop in EBV-naïve patients, particularly pediatric patients, who receive organs from EBV+ donors. A variety of non-standardized, non-specific treatments are used to treat EBV+ PTLD cases (4-9). Initial clinical management typically involves reduction of immunosuppression; however, this can lead to graft-versus-host disease. Other treatments including radiation/chemotherapy and excision of PTLD lesions all have undesirable side effects. Second-line treatment often includes antibodies (Abs) against the B cell antigen, CD20; however, this also targets healthy B cells, further weakening the immune system and exposing patients to other opportunistic infections.

In over 50 years of EBV vaccine research, few candidates have demonstrated partial clinical efficacy, and none have been efficacious enough to elicit sterilizing immunity and be licensed (24). Antibodies, whether elicited in the host naturally or via passive immunization, provide an effective first-line of defense against viral infection.

Thus, there is an urgent need for a novel EBV-specific therapy that targets EBV+ cells to neutralize EBV infection and prevent subsequent PTLD development in EBV-naïve patients.

SUMMARY

In one aspect, this disclosure relates to an Epstein-Barr virus (EBV) antibody or an immunogenic fragment thereof. In some embodiments, the EBV antibody or an immunogenic fragment thereof specifically binds to EBV glycoprotein 350/220. In some embodiments, the EBV antibody or an immunogenic fragment thereof specifically binds to EBV glycoprotein 350 or one or more epitopes represented by SEQ ID NOs: 1-3. In some embodiments, the EBV antibody comprises a VH region comprising CDR-1, CDR-2, and CDR-3 represented by SEQ ID NOs: 4-19, 20-35, and 36-51, respectively. In some embodiments, the EBV antibody comprises a VL region comprising CDR-1, CDR-2, and CDR-3 represented by SEQ ID NOs: 52-67, 68-83, and 84-99, respectively. In some embodiments, the antibody is not antibody clone 72A1 or an antibody comprising the CDRs of antibody clone 72A1. In some embodiments, the EBV antibody is a monoclonal antibody. In some embodiments, the EBV antibody is a chimeric antibody, a human antibody, or a humanized antibody.

In another aspect, this disclosure relates to an immunogenic peptide comprising one or more gp350 epitopes having an amino acid sequence identical to or sharing at least 60% similarity to SEQ ID NO: 1, SEQ ID NO: 2, or SEQ ID NO: 3. In some embodiments, the immunogenic peptide comprises a first domain comprising an amino acid sequence having at least 60% similarity to SEQ ID NO:1, a second domain comprising an amino acid sequence having at least 60% similarity to SEQ ID NO: 2, and a third domain comprising an amino acid sequence having at least 60% similarity to SEQ ID NO: 3. In some embodiments, the immunogenic peptide comprises a first domain comprising an amino acid sequence having at least 60% similarity to SEQ ID NO: 1, SEQ ID NO: 2, or SEQ ID NO: 3, and a second domain comprising a known immunogenic peptide such as keyhole limpet hemocyanin (KLH) peptide.

In another aspect, this disclosure relates to an EBV antibody-small molecule conjugate. The EBV antibodies disclosed herein can be conjugated to small molecules having activities against EBV-transformed cells. For example, the small molecules have anti-proliferative activities against EBV-transformed B lymphoma cells. In some embodiments, the small molecules are growth inhibitors of EBV infected B cells. In some embodiments, the small molecule is $L_2P_4$, 2-butynediamide, or a derivative thereof. In some embodiments, the small molecule is conjugated to the antibody via a linker or an adaptor. In some embodiments, the small molecule is conjugated to the constant region of the heavy chain or the light chain of the antibody.

In a related aspect, this disclosure relates to a pharmaceutical composition comprising the EBV antibody disclosed herein or an immunogenic fragment thereof, one or more epitopes represented by SEQ ID NOs: 1-3, one or more immunogenic peptides disclosed herein, or the EBV antibody-small molecule conjugate disclosed herein. The pharmaceutical composition can further comprise one or more pharmaceutically acceptable excipients. The pharmaceutical composition can be formulated into any suitable formulation depending on the administration route.

In another aspect, this disclosure relates to a method of neutralizing EBV infection. The method includes administering to a subject infected with EBV a therapeutically effective amount of the EBV antibody disclosed herein or an immunogenic fragment thereof, one or more epitopes represented by SEQ ID NOs: 1-3, one or more immunogenic peptides disclosed herein, the EBV antibody-small molecule conjugate, or the pharmaceutical composition described above. In some embodiments, the subject is human.

In another aspect, this disclosure relates to a method of preventing EBV infection. The method includes administering to a subject at an elevated risk of EBV infection a therapeutically effective amount of the EBV antibody disclosed herein or an immunogenic fragment thereof, one or more epitopes represented by SEQ ID NOs: 1-3, one or more immunogenic peptides disclosed herein, the EBV antibody-small molecule conjugate, or the pharmaceutical composition described above. In some embodiments, the subject is human.

In another aspect, this disclosure relates to a method of preventing a post-transplant lymphoproliferative disease (PTLD). PTLD is associated with EBV infection of B cells, either as a consequence of reactivation of the virus post transplantation or from primary EBV infection. The method includes administering to a subject who is a transplant recipient a therapeutically effective amount of the EBV antibody disclosed herein or an immunogenic fragment thereof, one or more epitopes represented by SEQ ID NOs: 1-3, one or more immunogenic peptides disclosed herein, the EBV antibody-small molecule conjugate, or the pharmaceutical composition described above. The administration can be before, during, and/or after the transplant. In some embodiments, the subject is a pediatric transplant recipient who is EBV naïve. In some embodiments, the subject is an adult transplant recipient. In some embodiments, the subject is human.

In another aspect, this disclosure relates to a method of treating an EBV-associated cancer. The method includes administering to a subject suffering from an EBV-associated cancer a therapeutically effective amount of the EBV antibody disclosed herein or an immunogenic fragment thereof, one or more epitopes represented by SEQ ID NOs: 1-3, one or more immunogenic peptides disclosed herein, the EBV antibody-small molecule conjugate, or the pharmaceutical composition described above. In some embodiments, the examples of EBV-associated cancer include but are not limited to Hodgkin lymphoma, Burkitt lymphoma, gastric cancer, and nasopharyngeal carcinoma. In some embodiments, the subject is human.

In another aspect, this disclosure relates to a method of immunizing or vaccinating a subject against an EBV infection. The method includes administering to a subject suffering from an EBV infection a therapeutically effective amount of the EBV antibody disclosed herein or an immunogenic fragment thereof, one or more epitopes represented by SEQ ID NOs: 1-3, one or more immunogenic peptides disclosed herein, or the pharmaceutical composition thereof as described above. In some embodiments, the subject is human.

In another aspect, this disclosure relates to a method of inducing the production of neutralizing antibodies against a EBV in a subject. The method includes administering to a subject an effective amount of a gp350 epitope represented by SEQ ID NO: 3 or an immunogenic peptide comprising the gp350 epitope represented by SEQ ID NO: 3. In some embodiments, the subject is human.

BRIEF DESCRIPTION OF THE DRAWINGS

FIG. 1A: ELISA screening of hybridoma (HB) supernatants for anti-gp350-specific antibodies. Soluble EBV gp350 protein was used as the target antigen at 0.5 µg/ml. nAb-72A1 at 10 µg/ml and 1× phosphate buffered saline (PBS) were used as positive and negative (not shown) controls, respectively. Bound antibodies were detected using HRP-conjugated anti-mouse IgG (1:2,000). Twenty-three HB clones with ELISA signals two times greater than those of PBS control were considered as positive hybridomas. FIG. 1B: Determining specificity of anti-gp350 producing hybridoma supernatant by immunoblotting with gp350-transfected stable CHO lysate. Western blot analysis was conducted on untransfected and pCAGGS-gp350 transfected CHO lysate. Anti-gp350 mAb 72A1 was used as a positive control (1:100) and anti-gp350 hybridoma clone supernatants were used at 1:50. Anti-mouse secondary antibody was used at 1:2000. FIG. 1C: Flow cytometric analysis of surface expression of gp350 protein on gp350 expressing CHO cells for all 23 HB clones. $10^6$ CHO cells were transfected with 1 µg of pCAGGS-gp350. gp350 expressing cells were resuspended in PBS, stained with anti-gp350 mAb (1:250), which detects the gp350 ED, followed by secondary goat anti-mouse conjugated to AF488. FIG. 1D: Flow cytometric analysis of HB5, HB17 and HB19.

FIGS. 2A and 2B show PROMALS3D multiple sequence alignment of VH (FIG. 2A) and VL (FIG. 2B) regions of 15 mAbs and nAb-72A1 (SEQ ID NOS:100-131). The highly variable complementarity determining regions (CDR) 1-3, indicated by black boxes, define the antigen binding specificity. The conserved framework regions (FR) 1-4 flank the CDRs. Consensus amino acid (aa) are in bold and upper case. Consensus predicted secondary structure (ss) symbols: alpha-helix: h and beta-strand: e.

FIG. 4A: Construction of chimeric Ab. FIG. 4B: Cloning strategy of heavy chain and light chain variable regions into expression vectors. FIG. 4C: PCR amplification of heavy chain and light chain variable regions. 72A1 and clone 19 were used as examples of PCR amplification.

DETAILED DESCRIPTION

Figure 1A:
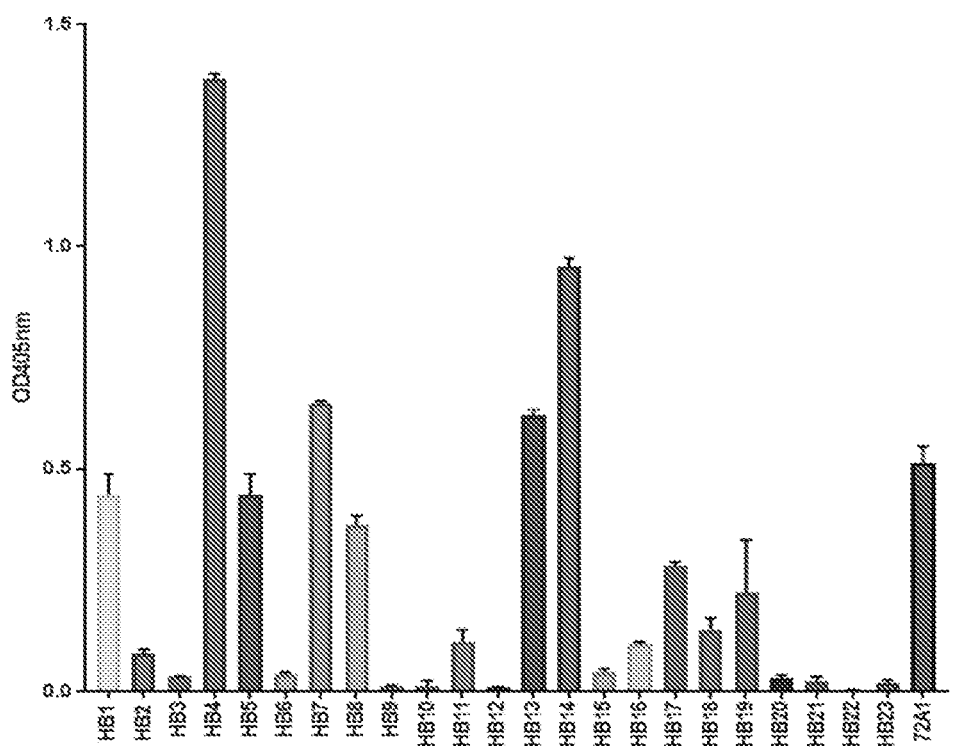
FIGS. 1A-1D show characterization of novel anti-gp350 mAbs.

Disclosed herein are EBV antibodies or immunogenic fragments thereof that specifically bind to gp350/gp220 or an epitope of gp350, immunogenic peptides comprising one or more gp350 epitopes, or one or more amino acid sequences having at least 60% similarity to one or more gp350 epitopes, EBV antibody-small molecule conjugates for treating or preventing EBV infection, in particular, in subjects receiving a transplant. In some embodiments, chimeric (human/mouse) anti-gp350 nAbs are conjugated to $L_2P_4$ to obtain an EBV-specific ADC that improves the therapeutic efficacy of treating EBV-associated PTLDs. $L_2P_4$ described by Jiang et al., *Nature Biomedical Engineering* 1: 0042 (2017), is an example of the small molecules encompassed by this disclosure.

The term "antibody" as used herein refers to an immunoglobulin molecule or an immunologically active portion thereof that specifically binds to, or is immunologically reactive with a particular antigen, for example, EBV gp350/gp220, or a particular domain or fragment of gp350/gp220. In some embodiments, the antibody disclosed herein specifically binds to one or more epitopes on EBV gp350. The epitopes can be neutralizing epitopes or immunodominant epitopes. In some embodiments, the epitope has an amino acid sequence selected from $_{253}$TPIPGTGYAYSLRLT-PRPVSRFL$_{275}$ (SEQ ID NO: 1), $_{875}$LLLLVMAD-CAFRRNLSTSHTYTTPPY$_{899}$ (SEQ ID NO: 2), and $_{381}$GAFASNRTFDIT$_{392}$ (SEQ ID NO: 3).

In a related aspect, this disclosure relates to a method of producing an EBV antibody using the epitopes disclosed herein according to any known technology. The method entails immunizing an animal such as a mouse or a rabbit with an immunogenic peptide disclosed herein or the epitope represented by SEQ ID NO: 1, SEQ ID NO: 2, or SEQ ID NO:3 alone, and screening for and isolating a hybridoma producing an EBV antibody. The EBV antibody produced from such hybridomas can be used for treating or preventing EBV infections.

In certain embodiments an antibody for use in the present methods or compositions is a full-length immunoglobulin molecule, which comprises two heavy chains and two light chains, with each heavy and light chain containing three complementary determining regions (CDRs). The CDRs of various antibodies are identified and listed in Table 1 below.

TABLE 1

CDR Sequences

| Antibodies | VH | | | VL | | |
|---|---|---|---|---|---|---|
| | CDR-1 | CDR-2 | CDR-3 | CDR-1 | CDR-2 | CDR-3 |
| 72A1 | GSSFTDY (SEQ ID NO: 4) | INPYNGG (SEQ ID NO: 20) | GGLRRVNWFAYW (SEQ ID NO: 36) | TGAVTTSNY (SEQ ID NO: 52) | GTN (SEQ ID NO: 68) | VLWHSNHWV (SEQ ID NO: 84) |
| HB-1 | GFLLTTY (SEQ ID NO: 5) | IWAGGS (SEQ ID NO: 21) | RDRGYGYLYAMDYW (SEQ ID NO: 37) | QNVGTN (SEQ ID NO: 53) | STD (SEQ ID NO: 69) | QQYNTYPYT (SEQ ID NO: 85) |
| HB-2 | GYTFTAY (SEQ ID NO: 6) | INYKTGE (SEQ ID NO: 22) | PYGYALDYW (SEQ ID NO: 38) | SSVNY* (SEQ ID NO: 54) | ATS* (SEQ ID NO: 70) | QQWSSNPPT* (SEQ ID NO: 86) |
| HB-3 | GYTFASY (SEQ ID NO: 7) | INPNNGH* (SEQ ID NO: 23) | RNLYYYGRPDYW* (SEQ ID NO: 39) | QDIGNY* (SEQ ID NO: 55) | YTS* (SEQ ID NO: 71) | QQGNTLPPT* (SEQ ID NO: 87) |
| HB-5 | GYTFTNH (SEQ ID NO: 8) | INPYNDY (SEQ ID NO: 24) | RSEGWLRRGAWFAY (SEQ ID NO: 40) | QSIGTS (SEQ ID NO: 56) | YAS (SEQ ID NO: 72) | QQSNSWPMLT (SEQ ID NO: 88) |
| HB-6 | GYTFTDY* (SEQ ID NO: 9) | INTRTGE (SEQ ID NO: 25) | PYGYALDYW (SEQ ID NO: 41) | SSVNY* (SEQ ID NO: 57) | ATS* (SEQ ID NO: 73) | QQWSSNPPT* (SEQ ID NO: 89) |
| HB-7 | GYTFTDY* (SEQ ID NO: 10) | ISPGRSG (SEQ ID NO: 26) | RYGHPSYLDVW (SEQ ID NO: 42) | QSVGNA (SEQ ID NO: 58) | SAS (SEQ ID NO: 74) | QQYSSYPLT (SEQ ID NO: 90) |
| HB-8 | GYSFTNY* (SEQ ID NO: 11) | INTYTGE (SEQ ID NO: 27) | RYYYGSVYSAWFAYW (SEQ ID NO: 43) | QSIVHSNGNTY* (SEQ ID NO: 59) | KVS* (SEQ ID NO: 75) | FQGSHVPYT* (SEQ ID NO: 91) |
| HB-9 | GFTFSSY (SEQ ID NO: 12) | ISSGGSY (SEQ ID NO: 28) | REDFYYGSSYGFFDVW (SEQ ID NO: 44) | QSIVHSNGNTY* (SEQ ID NO: 60) | KVS* (SEQ ID NO: 76) | FQGSHVPYT* (SEQ ID NO: 92) |
| HB-10 | GYTFTSY* (SEQ ID NO: 13) | INPSNGH (SEQ ID NO: 29) | RNLYYYGRPDYW (SEQ ID NO: 45) | QDIGNY* (SEQ ID NO: 61) | YTS* (SEQ ID NO: 77) | QQNTLPPT (SEQ ID NO: 93) |
| HB-11 | GDSITSG (SEQ ID NO: 14) | ISYSGS (SEQ ID NO: 30) | RGNGGNYDWYFDVW (SEQ ID NO: 46) | SSVNF (SEQ ID NO: 62) | YIS (SEQ ID NO: 78) | QQFTSSPSWT (SEQ ID NO: 94) |
| HB-12 | GYTFTNY* (SEQ ID NO: 15) | INPNNGH* (SEQ ID NO: 31) | RNLYYYGRPDYW* (SEQ ID NO: 47) | QSLVHSNGNTY (SEQ ID NO: 63) | KVS* (SEQ ID NO: 79) | SQSTHVPLT (SEQ ID NO: 95) |
| HB-14 | GYTFTDY* (SEQ ID NO: 16) | IHPRRGG (SEQ ID NO: 32) | RYGYPWYFDVW (SEQ ID NO: 48) | QSIVHDNGNTY (SEQ ID NO: 64) | KVS* (SEQ ID NO: 80) | FQGSHVPPT (SEQ ID NO: 96) |
| HB-17 | GYTFTSY* (SEQ ID NO: 17) | INPNNGH* (SEQ ID NO: 33) | RNLFYYSRPDYW (SEQ ID NO: 49) | QDIGNY* (SEQ ID NO: 65) | YTS* (SEQ ID NO: 81) | QQGNTLPPT* (SEQ ID NO: 97) |
| HB-20 | GYTFTSY* (SEQ ID NO: 18) | INPTNGH (SEQ ID NO: 34) | RNLYYYGRPDYW* (SEQ ID NO: 50) | QDIGNY* (SEQ ID NO: 66) | YTS* (SEQ ID NO: 82) | QQGNALPPT (SEQ ID NO: 98) |

TABLE 1-continued

CDR Sequences

| Anti-bodies | VH | | | VL | | |
|---|---|---|---|---|---|---|
| | CDR-1 | CDR-2 | CDR-3 | CDR-1 | CDR-2 | CDR-3 |
| HB-22 | GFSLTNY (SEQ ID NO: 19) | IWSDGS (SEQ ID NO: 35) | RNYYGNSYPAWFAYW (SEQ ID NO: 51) | QSIVHSNGNTY (SEQ ID NO: 67) | KVS* (SEQ ID NO: 83) | FQGSHVPVVT (SEQ ID NO: 99) |

The term "antibody," in addition to natural antibodies, also includes genetically engineered or otherwise modified forms of immunoglobulins, such as synthetic antibodies, intrabodies, chimeric antibodies, fully human antibodies, humanized antibodies, peptibodies and heteroconjugate antibodies (e.g., bispecific antibodies, multispecific antibodies, dual-specific antibodies, anti-idiotypic antibodies, diabodies, triabodies, and tetrabodies). The antibodies disclosed herein can be monoclonal antibodies or polyclonal antibodies. In those embodiments wherein an antibody is an immunologically active portion of an immunoglobulin molecule, the antibody may be, for example, a Fab, Fab', Fv, Fab' F(ab')$_2$, disulfide-linked Fv, single chain Fv antibody (scFv), single domain antibody (dAb), or diabody. The antibodies disclosed herein, including those that are immunologically active portion of an immunoglobulin molecule, retain the ability to bind a specific antigen, for example, EBV gp350 or one or more epitopes thereof, EBV gp220 or one or more epitopes thereof, or to bind a specific fragment of gp350/gp220.

In some embodiments, the EBV antibodies disclosed herein have undergone post-translational modifications such as phosphorylation, methylation, acetylation, ubiquitination, nitrosylation, glycosylation, or lipidation associated with expression in a mammalian cell line, including a human or a non-human host cell. Techniques for producing recombinant antibodies and for in vitro and in vivo modifications of recombinant antibodies are known in the art.

Provided in certain embodiments herein are chimeric, and/or humanized EBV antibodies. Various techniques are known in the art for humanizing antibodies from non-human species such that the antibodies are modified to increase their similarity to antibodies naturally occurring in humans. Six CDRs are present in each antigen binding domain of a natural antibody. These CDRs are short, non-contiguous sequences of amino acids that are specifically positioned to form the antigen binding domain as the antibody assumes its three dimensional configuration. CDR sequences of certain antibodies identified herein are shown in Table 1. The remainder of the amino acids in the antigen binding domains, referred to as "framework" regions, show less inter-molecular variability and form a scaffold to allow correct positioning of the CDRs. This disclosure also relates to antibodies comprising VH and VL regions comprising the CDRs shown in Table 1.

"Treating" or "treatment" of a disease or a condition may refer to preventing the disease or condition, slowing the onset or rate of development of the disease or condition, reducing the risk of developing the disease or condition, preventing or delaying the development of symptoms associated with the disease or condition, reducing or ending symptoms associated with the disease or condition, generating a complete or partial regression of the disease or condition, or some combinations thereof.

As used herein, the term "subject" refers to mammalian subject, preferably a human. The phrases "subject" and "patient" are used interchangeably herein.

The method for treating a condition or a viral infection includes administering a therapeutically effective amount of a therapeutic agent or a pharmaceutical composition. An "effective amount," "therapeutically effective amount" or "effective dose" is an amount of a composition (e.g., a therapeutic agent or a pharmaceutical composition) that produces a desired therapeutic effect in a subject, such as preventing or treating a target disease or condition or alleviating symptoms associated with the disease or condition. The precise therapeutically effective amount is an amount of the composition that will yield the most effective results in terms of efficacy of treatment in a given subject. This amount will vary depending upon a variety of factors, including but not limited to the characteristics of the therapeutic agent (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The pharmaceutical composition may include, among other things, an EBV antibody disclosed herein or an immunogenic fragment thereof, one or more gp350 epitopes represented by SEQ ID NOs: 1-3, one or more immunogenic peptides disclosed herein, or an EBV antibody-small molecule conjugate disclosed herein.

The pharmaceutical composition may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the therapeutic compositions described herein are administered by intravenous injection or intraperitoneal injection.

The epitopes disclosed herein have various uses. For example, the epitopes can be used to produce immunogenic peptides. Such an immunogenic peptide comprises one or more gp350 epitopes having an amino acid sequence identical to or sharing at least 60% similarity to SEQ ID NO: 1, SEQ ID NO: 2, or SEQ ID NO: 3. In some embodiments, the immunogenic peptide comprises a first domain comprising an amino acid sequence having at least 60% similarity to SEQ ID NO:1, a second domain comprising an amino acid sequence having at least 60% similarity to SEQ ID NO: 2, and a third domain comprising an amino acid sequence having at least 60% similarity to SEQ ID NO: 3. In some embodiments, the immunogenic peptide comprises a first domain comprising an amino acid sequence having at least 60% similarity to SEQ ID NO: 1, SEQ ID NO: 2, or SEQ ID NO: 3, and a second domain comprising a known immunogenic peptide such as keyhole limpet hemocyanin (KLH) peptide.

Additionally, the epitopes or immunogenic peptides disclosed herein can be used for producing anti-gp350 antibodies using any existing technology.

In certain embodiments, disclosed herein is a method of treating or preventing EBV infection in a subject, comprising administering a therapeutically effective amount of an anti-gp350 antibody disclosed herein or an immunogenic fragment thereof, one or more epitopes represented by SEQ ID NOs: 1-3, an immunogenic peptide described herein, an EBV antibody-drug conjugate described herein, or a pharmaceutical composition comprising the anti-gp350 antibody or an immunogenic fragment thereof, one or more epitopes, one or more immunogenic peptides, or the EBV antibody-drug conjugate.

In certain embodiments, disclosed herein is a method of treating or preventing EBV infection in a subject, comprising administering a therapeutically effective amount of an anti-gp350 antibody disclosed herein or an immunogenic fragment thereof, one or more epitopes represented by SEQ ID NOs: 1-3, an immunogenic peptide described herein, an EBV antibody-drug conjugate described herein, or a pharmaceutical composition comprising the anti-gp350 antibody or an immunogenic fragment thereof, one or more epitopes, one or more immunogenic peptides, or the EBV antibody-drug conjugate.

In certain embodiments, disclosed herein is a method of treating or preventing EBV-associated PTLD in a subject, comprising administering a therapeutically effective amount of an anti-gp350 antibody disclosed herein or an immunogenic fragment thereof, one or more epitopes described herein, one or more immunogenic peptides described herein, an EBV antibody-drug conjugate described herein, or a pharmaceutical composition comprising the anti-gp350 antibody or an immunogenic fragment thereof, one or more epitopes, one or more immunogenic peptides, or the EBV antibody-drug conjugate, before or after the transplant in the subject.

As shown in the working examples, 15 novel EBV gp350-specific mAbs were generated, their binding to gp350 was characterized, their neutralization activity against EBV infection in vitro was determined, their cognate epitopes were mapped, and the exact aa residues they recognize on gp350 were defined. Six of the eight previously described epitopes responsible for generating neutralizing and non-nAbs were confirmed and the exact aa residues that they bind were defined. This study also confirmed that the binding epitopes on gp350 that elicit nAbs are between aa 4-443 (59). An additional neutralizing epitope and two new non-neutralizing epitopes, with one located downstream of the gp350 ectodomain (aa 1-841) were identified. Importantly, the newly developed mAbs have many uses in vaccine development, diagnosis of viral infection, and therapeutic/prophylactic management of post-transplant lymphoproliferative diseases, either individually, in combination with nAb-72A1, or with other mAbs such as anti-gH/gL (E1D1).

To overcome the existing challenges facing PTLD treatment, novel EBV antibodies and EBV antibody-drug conjugates (ADCs) are developed. The EBV neutralizing antibodies (nAbs) that specifically block new or reactivated EBV infection are conjugated with small molecules that specifically target latent viral protein, EBV nuclear antigen 1 expressed in all EBV+ malignancies. The recent identification and isolation of nAbs against the highly variable viruses HIV-1 (10, 11), influenza (12-14), and respiratory syncytial virus (15) has direct implications for successful EBV protection. Indeed, in 2012, an international, multidisciplinary expert panel recommended use of intravenous (IV) anti-viral nAbs for preventing or treating EBV+ PTLD (16). EBV uses multiple surface glycoproteins (gps), including the major gp350, to infect host cells (17, 18). These gps are expressed on EBV virions and in EBV+ cells (19, 20), and stimulate immune responses in humans and in animal models (21-23), making them attractive targets for an EBV vaccine (24). Multiple lines of evidence suggest that use of anti-gp350 nAbs to protect against EBV-PTLDs is feasible (16): (A) Maternal Abs protect against EBV infection in neonates (25, 26); (B) gp350-expressing EBV+ cells activate complement (27) and mediate Ab-dependent cellular cytotoxicity (28); (C) gp350 vaccines reduce EBV load and protect against EBV+ lymphomas in marmosets (29-32) and protect EBV-naïve adults from EBV-induced mononucleosis (32-34); (D) Compared to control mice, SCID mice injected with peripheral blood mononuclear cells from EBV-naïve donors and immunized with anti-gp350 (72A1) mouse nAb are completely protected against EBV and development of EBV+ tumors or PTLD-like lesions (35); and (E) 72A1 also conferred short-term protection against acquiring EBV after transplantation in 3 out of 4 pediatric patients in a small phase 1 clinical trial (35). However, there was a major drawback: all 4 patients who received 72A1 developed human anti-mouse Abs (HAMA), which can cause side effects and limit treatment efficacy, with one developing a hypersensitivity reaction. This suggests that 72A1 in its native form is not a safe treatment for humans (35). Thus, chimeric (human/mouse), humanized, or human nAbs, which are safe and effective in the treatment of various cancers, are needed (7, 36-38).

Pre-existing antibodies provide the primary defense against viral infection. Prophylactic prevention of EBV primary infection has mainly focused on blocking the first step of viral entry by generating neutralizing antibodies (nAbs) that target EBV envelope glycoproteins. Five glycoproteins, in particular, gp350/220 (gp350), gp42, gH, gL, and gB, are required for efficient infection of permissible host cells and have emerged as potential prophylactic targets (23, 24, 61, 64).

Several studies have indicated that the EBV gp350 as the major immunodominant glycoprotein is an ideal target for EBV nAbs production. Although the ectodomain of EBV gp350 (aa 1-841) has been shown to contains at least eight unique CD21 binding epitopes, only one of these epitopes (aa 142-161) is capable of eliciting nAbs (57-58). The aa residues that constitute the other epitopes and their role in generating nAb has not been elucidated, as this information would be valuable in the precise design of effective EBV peptide vaccine. To date, nAb-72A1 remains the only EBV antibody with proven clinical prophylactic efficacy, as its been shown to confer short-term protection by reducing and delaying EBV infection onset in immunized pediatric transplant patients (35).

EBV predominantly infects epithelial cells and B cells, reflecting the viral tropism and the cellular ontogeny for EBV-associated malignancies (17). There are two schools of thought on how the initial EBV transmission into the human host occurs. In the first infection model, the incoming virus engages with ephrin receptor A2 via heterodimeric gH/gL, which triggers gB fusion with the epithelial cell membrane and entry of the virus into the cytoplasm (17). This interaction is thought to occur in the oral mucosa, where the virus undergoes lytic replication to release virions that subsequently infect B cells. In the alternative model, the incoming virus binds to the host cell via complement receptor type 1 (CR1)/CD35 (45) and/or CR2/CD21 through its major immunodominant glycoprotein, gp350 (65). The interaction between gp350 and CD35 and/or CD21 triggers viral adsorption, capping, and endocytosis into the B cell (66), which subsequently leads to interaction between heterotrimeric viral glycoproteins complex, gp42/gH/gL, binding to HLA class II molecules to activate gB membrane fusion and entry. Because these two models are not necessarily mutually exclusive, and given that both gp350 and gH/gL complex are important in initiating the first viral contact with host cells, use of nAbs that target either gp350 or gH/gL complex or both may potently block incoming virus at the oral mucosa.

Nearly all EBV-infected individuals develop nAbs directed to the ectodomains of these glycoproteins (52, 67). These antibodies can prevent neonatal infection, and can protect against acute infectious mononucleosis in adolescents and several human lymphoid and epithelial malignancies associated with EBV infection (30, 32-34). Although numerous monoclonal antibodies (mAbs) have been generated against EBV gp350 (53, 68, 69), only two murine mAbs, the non-neutralizing 2L10 and the neutralizing 72A1, have been extensively characterized and made commercially available (68, 69). Importantly, nAb-72A1 conferred short-term clinical protection against EBV transmission after transplantation in pediatric patients in a small phase I clinical trial (35).

EBV gp350 is the most immunogenic envelope glycoproteins on the virions. It is a type 1 membrane protein that encodes for 907 amino acid (aa) residues. A single splice of the primary transcript deletes 197 codons and joins gp350 codons 501 and 699, in frame, to generate the gp220 messenger RNA. Both gp350 and gp220 are comprised of the same 18-aa residue at the C terminus that is located within the viral membrane, a 25-aa residue at the transmembrane-spanning domain, and a large highly glycosylated N-terminal ectodomain, aa 1-841 (57). The first 470 aa of gp350 are sufficient for binding CD21 in B cells, as demonstrated by a truncated gp350 (aa 1-470) blocking the binding of EBV to B cells and reducing viral infectivity (17). The gp350-binding domain on CD21 is mapped to N-terminal short consensus repeats (SCRs) 1 and 2, which also bind to a bioactive fragment of complement protein 3 (C3d) (34, 68). A soluble truncated EBV gp350 fragment (aa 1-470) and soluble CD21 SCR1 and SCR2 can block EBV infection and immortalization of primary B cells (57). However, gp350 binding to CD35 is not restricted to N-terminal SCRs; it binds long homologous repeat regions as well as SCRs 29-30 (57).

The gp350 ectodomain is heavily glycosylated, with both N- and O-linked sugars, which accounts for over half of the molecular mass of the protein. Currently there is only one crystal structure available for gp350, comprised of a truncated structure between 4-443 aa, with at least 14 glycosylated arginines coating the protein with sugars, with the exception of a single glycan-free patch (59). Mutational studies of several residues in the glycan-free patch resulted in the loss of CD21 binding (59), suggesting that binding of CD35 and CD21 by gp350 is mediated within this region.

There are at least eight unique CD21 binding epitopes located at the N-terminus of the gp350 ectodomain (58); at least one of these epitopes (aa 142-161) is capable of eliciting nAbs (57, 58). The aa residues 142-161 are also the binding site for nAb-72A1 (59, 68). Using gp350 synthetic peptides binding to CD21 on the surface of a B cell line, additional gp350 epitope was identified in the C-terminal region of gp350 (aa 822-841), suggesting it is involved in EBV invasion of B cells (58). The role of other epitopes in eliciting nAbs has not been fully investigated. Furthermore, the exact aa residues that comprise the core binding sites for epitope capable of eliciting neutralization and non-neutralization antibodies have not been determined. Mapping the EBV gp350 protein residues defining immunodominant epitopes, identifying the critical aa residues of the eight epitopes, and defining their roles in generating neutralizing and non-nAbs will guide rational design and construction of an efficacious EBV gp350-based vaccine that would focus the B-cell responses to the protective epitopes.

As demonstrated in the working examples, 23 hybridomas producing antibodies against EBV gp350 were generated. To assess their clinical potential and utility in informing future prophylactic and therapeutic vaccine design: (1) the ability of the antibodies produced by the new hybridomas to detect gp350 protein was tested by enzyme-linked immunosorbent assay (ELISA), flow cytometry, and immunoblot; (2) the unique CDRs of the heavy and light chains of all 23 hybridomas were sequenced to identify novel mAbs; (3) the efficacy of each mAb to neutralize EBV infection in vitro was measured; and (4) RepliTope peptide microarrays were used to identify gp350 core aa residues recognized by neutralizing and non-neutralizing mAbs. Using the newly generated antibodies, a new epitope bound preferentially by nAbs was identified, distinct from the canonical neutralizing epitope bound by nAb-72A1, as well as two immunodominant epitopes bound by both neutralizing and non-nAbs.

FIG. 1 demonstrates characterization of the 23 gp350-specific antibodies produced by hybridomas and their ability to bind gp350 protein. FIG. 2 demonstrates that out of 23 hybridomas, 15 hybridomas were determined to be monoclonal and novel based on the VH and VL CDR sequences compared to those of the reported nAb-72A1 (57).

Following confirmation that the new mAbs recognized EBV gp350 antigen and had unique VH-VL sequences, further characterization revealed that mAbs HB9, HB10, HB11, HB17, and HB20 inhibited EBV infection in a dose-dependent manner, with HB17 and HB20 being the best neutralizers (FIG. 3). Thus, provided herein are new nAbs and non-nAbs against EBV infection for therapeutic and prophylactic uses.

Various methods, including lectin/ricin immune-affinity assay (69), purified mAbs (53, 70), purified soluble gp350 mutants (57), synthetic peptides (51, 55, 54), cell binding assays (58), and crystal structure of partial gp350 protein (4-443) (59), have been used to identify the critical gp350 epitopes responsible for its interaction with the CD35 and CD21 cellular receptors (for a detailed summary review see Table 2).

The epitope mapping assay identified a total of nine epitopes including two new epitopes, one bound by all mAbs, including nAb-72A1 and 2L10, regardless of the mAb neutralizing capability suggesting it is an immunodominant epitope on the gp350 protein. Portions of six of the previously described epitopes, including the only currently recognized neutralizing epitope were also identified and their exact aa residues were defined. However, two previously reported epitopes located at aa 282-301 and aa 194-211, which have been reported to be involved in the binding of nAb-72A1 or CD21, respectively (51, 58, 59), were not identified.

As demonstrated in the working examples, the comparative epitope mapping analysis results identified a novel neutralizing epitope, $_{381}$GAFASNRTFDIT$_{392}$ (SEQ ID NO; 3), which was bound preferentially by the nAbs HB20 and nAb-72A1, but not the non-neutralizing mAb HB5. The new neutralizing epitope is distinct from the reported canonical nAb-72A1 binding epitope aa 142-161, on gp350, suggesting that epitope 381-392 is a novel epitope on gp350 capable of eliciting nAbs using existing technology and protocols.

TABLE 2

Summary of gp350 Epitope Mapping over Time Using Different Methodologies

| Method | mAbs/protein/peptides | Number of epitopes | Reference |
|---|---|---|---|
| Competitive binding assay Tagged mAb vs untagged mAbs | Newly generated mAbs from purified virus or whole cell perp after induction | 8 epitopes- Sequence not defined | Qualtiere et al., 1987 (53) |
| Binding studies- determine the effects of anti-gp350 mAbs on gp350 binding to CR2 | Newly generated mAbs (61) | 2 possible regions identified by sequence alignment to C3d sequence. 1. aa 21-28 2. aa 372-378 | Nemerow et al 1987 (54) |
| Binding studies | Peptide and protein | 1. aa 21-28 2. N-terminus of gp350 | Nemerow et al 1989 (55) |
| Dot Blot immunoasaay Purified truncated protein incubated with mAbs | Protein - 8 clones overlapping N and C terminus portions of protein mAbs from Qualtiere et al., 1987 | 3 sequences defined 1. aa 310-325 2. aa 326-439 3. aa 733-841 | Zhang et al., 1991 (56) |
| Peptide digest and immunoprecipitation | Truncated and mutant protein mAbs (72A1 and BOS-1) | Narrowed down to the first 470 residues | Tanner et al., 1998 (57) |
| Peptide cell binding assay- to 2 CR2 positive (Raji and Ramos) and 1 negative (P3HR-1) cell line | Synthesized peptides covering gp350 (907aa) | 7 regions 3 identified 1. aa 142-161 2. aa 282-301 3. aa 822-841 | Urquiza et al 2005 (58) |
| Crystal structure and binding studies | Mutant proteins, mAbs 72a1 | 3 epitopes (based on 72A1 binding and gp350 4-443) 1. aa 16-29 2. aa 142-161 3. aa 282-301 | Szakonyi et al., 2006 (59) |
| Structural docking studied and antigenicity mapping | Gp350 and CR2 crystal structure alignment/docking | Single epitope (based on gp350 (1-470)) 1. aa147-165 | Sitompul et al., 2012 (60) |
| Structural alignment (computer modeling of gp350 and 72A1)/ docking studies | Peptides (used in immunization) and mAb (72A1) | 3 epitopes 1. aa 14-20 2. aa 144-161 3. aa 194-211 | Tanner et al., 2015 (51) |

Virus-specific treatments are less likely to target basic metabolic mechanisms of healthy cells, making them more likely to efficiently kill virus-infected cells with fewer side effects. Until recently, few drug regimens have specifically targeted EBV+ lymphomas. However, in 2015, a few small molecules showed activity against EBV-transformed cells (39). Furthermore, in 2017, Jiang et al. described a novel small molecule ($L_2P_4$) that shows discriminating anti-proliferative activities against EBV-transformed B lymphoma cells (40).

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLES

Example 1: Materials and Methods

Cells and viruses. EBV-AGS, a human gastric carcinoma cell line infected with a recombinant Akata virus expressing enhanced fluorescent green protein (eGFP) was a kind gift of Dr. Lisa Selin (University of Massachusetts Medical School). Anti-EBV gH/gL (E1D1) hybridoma cell line was a kind gift of Dr. Lindsey Hutt-Fletcher (Louisiana State University Health Sciences Center). Chinese hamster ovary cells (CHO); human embryonic kidney cells expressing SV-40 T antigen (HEK-293T); HEK-293 6E suspension cells; EBV-positive Burkitt lymphoma cells (Raji); myeloma cells (P3×63Ag8.653); and anti-EBV gp350 nAb-72A1 hybridoma cells (HB168) were purchased from American Type Culture Collection (ATCC). EBV-AGS cells were maintained in Ham's F-12 media supplemented with 500 µg/ml neomycin (G418, Gibco). Raji, P3×63Ag8.653, and HB168 hybridoma cells were maintained in RPMI 1640. CHO and HEK-293T cells were maintained in DMEM. HEK-293 6E cells were maintained in FreeStyle F17 Expression Medium supplemented with 0.1% Pluronic F-68. All culture media were supplemented with 10% fetal bovine serum (FBS), 2% penicillin-streptomycin, and 1% l-glutamine, with the exception of Freestyle F17 expression medium.

Antibodies and plasmids. Primary antibodies: EBV anti-gp350 nAb (72A1) and anti-gH/gL (E1D1) were purified from the supernatant of HB168 and E1D1 hybridoma cell lines, respectively, using Capturem™ Protein A Maxiprep spin columns (Takara). Anti-gp350/220 mAb (2L10) was purchased from Millipore Sigma.

Secondary antibodies: Horseradish peroxidase (HRP)-conjugated goat anti-mouse IgG for immunoblot or ELISA were purchased from Bio-Rad. Alexa Fluor (AF) 488-conjugated goat anti-mouse IgG (H+L) for flow cytometry was purchased from Life Sciences Tech. Goat anti-mouse IgG (H+L) secondary antibody and DyLight 650 for epitope mapping were purchased from Thermo Fisher Scientific.

The construction of the pCI-puro vector and pCAGGS-gp350/220-F has been described (23, 45).

Virus production and purification. eGFP-tagged EBV was produced from the EBV-infected AGS cell line as described (46). Briefly, EBV-AGS cells were seeded to 90% confluency in T-75 flasks in Ham's F-12 medium containing G418 antibiotic. After the cells reached confluency, G418 media was replaced with Ham's F-12 medium containing 33 ng/ml 12-O-tetradecanoylphorbol-13-acetate (TPA) and 3 mM sodium butyrate (NaB) to induce lytic replication of the virus. Twenty-four h post-induction, the media was replaced with complete Ham's F-12 media without G418, TPA, or NaB and cells were incubated for 4 days at 37° C. The cell supernatant was collected, centrifuged, and filtered using 0.8 µm filter to remove cell debris. The filtered supernatant was ultra-centrifuged using a Beckman-Coulter type 19 rotor for 70 min at 10,000 rpm to pellet the virus. EBV-eGFP virus was titrated in both HEK-293T cells and Raji cells, and stocks were stored at −80° C. for subsequent experiments.

Generation and purification of gp350 virus-like particles. To generate gp350 VLPs, equal amounts (8 µg/plasmid) of the relevant plasmids (pCAGGS-Newcastle disease virus (NDV) M, —NP, and gp350 ectodomain fused to fusion protein cytoplasmic and transmembrane domains) were co-transfected into 80% confluent CHO cells seeded in T-175 cm2 flasks; supernatant from transfected cells was collected and VLPs were purified and composition characterized as previously described (47).

Production of hybridoma cell lines. Seven days prior to immunization, two eight-week-old BALB/c mice were bled for collection of pre-immune serum. The mice were immunized with purified UV-inactivated EBV three times (Day 0, 21, and 35), and boosted every 7 days three times (Day 42, 49, and 56) with VLPs incorporating gp350 on the surface after Day 35. The mice were sacrificed, and their splenocytes were isolated, purified, and used to fuse with $P_3\times63Ag8.653$ myeloma cells at a ratio of 3:1 in the presence of polyethylene glycol (PEG, Sigma). Hybridoma cells were seeded in flat-bottom 96-well plates and selected in specialized hybridoma growth media with HAT (Sigma) and 10% FBS.

Indirect ELISA. Hybridoma cell culture supernatant from wells that had colony-forming cells were tested for antibody production by indirect ELISA. Briefly, immunoplates (Costar 3590; Corning Incorporated) were coated with 50 µl of 0.5 µg/ml recombinant EBV gp350/220 (Millipore) protein diluted in phosphate buffered saline (PBS, pH 7.4) and incubated overnight at 4° C. After washing three times with PBS containing 0.05% (v/v) Tween 20 (washing buffer), plates were blocked with 100 µl washing buffer containing 2% (w/v) bovine serum albumin (BSA) then incubated for 1 h at room temperature and washed as above. 100 µl of hybridoma supernatant was added to each well (in triplicate) and incubated for 2 h at room temperature. PBS and nAb-72A1 were added as negative and positive controls, respectively. The plates were washed as described above, followed by incubation with goat anti-mouse IgG horseradish peroxidase-conjugated secondary antibody (1:2,000 diluted in PBS) at room temperature for 1 h. The plates were washed again and the chromogenic substrate 2,2'-azino-bis (3-ethylbenzothiazoline-6-sulphonic acid) (ABTS, Life Science Technologies) was added. The reaction was stopped using ABTS peroxidase stop solution containing 5% sodium dodecyl sulfate (SDS) in water. The absorbance was read at an optical density of 405 nm using an ELISA reader (Molecular Devices). Three independent were performed.

Antibody purification, quantification, and isotyping. Hybridoma cells from selected individual positive clones were expanded stepwise from 96-well plates to T-75 flasks. At confluence in T-75 flasks, supernatant from individual clones was collected, clarified by centrifugation (4,000 g, 10 min, 4° C.), and filtered through a 0.22-μm-membrane filter (Millipore). Antibodies were further purified by Capturem™ Protein A Maxiprep (Takara) and stored in PBS (pH 7.4) at 4° C. Antibodies were analyzed by SDS-PAGE to determine purity. Bicinchoninic acid assay (BCA assay; Thermo Fisher Scientific) was conducted to determine the concentration of purified antibodies. Isotype identification was performed with the Rapid ELISA mouse mAb isotyping kit (Thermo Fisher Scientific).

RNA extraction, cDNA synthesis, and sequencing of the variable region of the mAbs. Total RNA was extracted from $1\times10^6$ hybridoma cells using the RNeasy Mini Kit (Qiagen). Each hybridoma clone cDNA was synthesized in a total volume of 20 μl using Tetro Reverse Transcriptase (200 u), RiboSafe RNase Inhibitor, Oligo(dT)18 primer, dNTP mix (10 mM each nucleotide), and 100-200 ng RNA. Reverse transcription was performed at 45° C. for 30 min, and terminated at 85° C. for 5 min. The cDNA was stored at −20° C. Immunoglobulin (Ig) VH and VL were amplified using the mouse Ig specific primer set purchased from Novagen (48). The VH and VL genes were amplified in separate reactions and PCR products were visualized on 1% agarose gel.

The VH and VL amplicons were sequenced using an Illumina MiSeq platform: duplicate 50 μl PCR reactions were performed, each containing 50 ng of purified cDNA, 0.2 mM dNTPs, 1.5 mM MgCl2, 1.25 U Platinum Taq DNA polymerase, 2.5 μl of 10×PCR buffer, and 0.5 μM of each primer designed to amplify the VH and VL. The amplicons were purified using AxyPrep Mag PCR Clean-up kit (Thermo Fisher Scientific). The Illumina primer PCR PE1.0 and index primers were used to allow multiplexing of samples. The library was quantified using ViiA™ 7 Real-Time PCR System (Life Technologies) and visualized for size validation on an Agilent 2100 Bioanalyzer (Agilent Technologies) using a high-sensitivity cDNA assay. The sequencing library pool was diluted to 4 nM and run on a MiSeq desktop sequencer (Illumina). The 600-cycle MiSeq Reagent Kit (Illumina) was used to run the 6 μM library with 20% PhiX (Illumina), and FASTQ files were used for data analysis.

Chimeric mAb construct generation. To generate chimeric mAbs, the VH and VL sequences were cloned into the dual-vector system pFUSE CHIg/pFUSE CLIg (Invivo-Gen), which express the constant region of the heavy and light chains of human immunoglobulins, respectively (Genewiz). The constructs were transiently transfected into HEK-293 6E cells. The supernatants were collected at 72 h post-transfection and IgG was purified using protein NG affinity chromatography.

Immunoblot analysis. CHO cells were cultured and stably co-transfected with pCAGGS-gp350/220 F and pCI-puro vector containing a puromycin resistance gene. Forty-eight h post-transfection, DMEM media containing 10 μg/ml of puromycin was added to enrich for cells expressing gp350 protein. Puromycin-resistant clones were expanded, followed by flow cytometry sorting using nAb-72A1 to a purity >90%. EBV gp350-positive CHO cells were harvested and lysed in radioimmunoprecipitation assay buffer (RIPA) followed by centrifugation at 15,000 g for 15 min on a benchtop centrifuge. The supernatants were collected and heated at 95° C. for 10 min in SDS sample buffer containing β-mercaptoethanol, then separated using SDS-PAGE. Proteins were transferred onto a nitrocellulose membrane using an iBlot™ Transfer System (Thermo Fisher Scientific) followed by incubation in blocking buffer (1% BSA; 20 mM Tris-HCl, pH 7.5; 137 mM NaCl; and 0.1% Tween-20 [TBST]) for 1 h. The blots were incubated in TBST containing purified anti-gp350 antibodies (1:50) overnight at 4° C. After three washes with TBST, the blots were incubated with a goat anti-mouse conjugated to horseradish peroxidase (1:2000) in TBST for 1 h. After three washes, the antibody-protein complexes were detected using the Amersham ECL Prime Western Blotting Detection Reagent (GE Healthcare). All experiments were independently repeated three times.

Flow cytometry. To assess the ability of purified anti-gp350 mAb to detect surface expression of EBV gp350 protein by flow cytometry, CHO cells that stably express EBV gp350 were harvested and stained with purified anti-gp350 (10 μg/ml), followed by Alexa Fluor® 488 goat anti-mouse IgG secondary antibody. Flow cytometric analysis was performed on a C-6 FC (BD Biosciences) and data was analyzed using FlowJo Cytometry Analysis software (FlowJo, LLC) as described (47). All the experiments were independently repeated three times.

EBV neutralization assay. Purified individual anti-gp350 mAbs were incubated with purified AGS-EBV-eGFP (titer calculated to infect at least 20% of HEK293 cells seeded in 100 μl of serum-free DMEM) for 2 h at 37° C. To represent EBV infection of B cells, the pre-incubated anti-gp350 mAbs/AGS-EBV-eGFP were used to infect 5×105 Raji cells seeded in a 96-well plate. Anti-gp350 neutralizing 72A1 and non-neutralizing $2L_{10}$ mAbs served as positive and negative controls, respectively. Plates were incubated at 37° C. and the number of eGFP+ cells was determined using flow cytometry 48 h post-infection. All dilutions were performed in quintuplicate and the assays repeated three times for Raji cells. Antibody EBV neutralization activity was calculated as: % neutralization=(EBValone−EBVmAb)/(EBValone)×100.

Epitope mapping. Anti-gp350 mAbs were incubated with a multi-well EBV GP350/GP340 RepliTope (JPT) peptide microarray displaying 224 peptides (15mers with 11 aa overlap) in 3×7 subarrays. Briefly, anti-gp350 mAbs were diluted in blocking solution (TBS-T and 2% BSA) to a final concentration of 10 μg/ml and incubated with the microarray slide for 1 h at 30° C. with shaking. Slides was washed 5 times with wash buffer (TBS-T), followed by incubation with 1 μg/ml secondary antibody Dylight 650 (Thermo Fisher Scientific) for 1 h at 30° C. After washing 5 times with wash buffer and 2 times with distilled water, microarray slides were dried by centrifugation. Detection was performed using the Agilent DNA microarray scanner.

Example 2: Development and Characterization of Monoclonal Antibodies Against EBV Gp350

New EBV gp350-specific mAbs were generated and biochemically characterized, and their ability to neutralize EBV infection was evaluated. In addition, the antibodies were used to map immunodominant epitopes on the EBV gp350 protein. 23 novel monoclonal antibodies specific against EBV gp350 were developed. To generate hybridomas, BALB/c mice were immunized with purified UV-inactivated EBV and boosted with virus-like particles (VLPs) that incorporate EBV gp350 ectodomain on the surface to enrich for production of anti-gp350 antibodies, then splenocytes were isolated from the immunized mice and fused with myeloma cells. Specifically, five eight-week-old BALB/c mice were immunized with virus-like particles incorporating gp350/220 on the surface, four times (day 0, 14, 28, and 56) via intraperitoneal injection without adjuvants. At day 64, immunized mice were boosted once intravenously. Animals were sacrificed at Day 70 to harvest splenocytes for fusion with the mouse myeloma P3×63Ag8 cell line.

Indirect ELISA was used to screen supernatants from the hybridomas for specificity against purified EBV gp350 ectodomain protein (aa 4-863) and 23 hybridomas producing gp350 specific antibodies were identified. These novel antibodies were analyzed by flow cytometric analysis for surface expression of gp350 protein on $10^6$ CHO cells transfected with 1 µg of pCAGGS-gp350. gp350 expressing cells were resuspended in PBS, stained with anti-gp350 mAb, which detects the gp350 ED, followed by secondary Ab goat anti-mouse conjugated to AF488. Additionally, western blot analysis was conducted on untransfected and pCAGGS-gp350 transfected CHO lysate. Anti-gp350 mAb 72A1 was used as a positive control (1:100) and anti-gp350 hybridoma clone supernatants were used at 1:50, and anti-mouse secondary antibody was used at 1:2000.

The isotypes of the new antibodies were determined to be IgG1 (n=14), IgG2a (n=5), IgG2b (n=1), a mixture of IgG1 and IgG2b (n=1), and a mixture of IgG1 and IgM (n=2). It was found that all 23 hybridoma producing antibodies, designated HB1-23, recognized the gp350 antigen in an initial ELISA screening using unfractionated and unpurified hybridoma supernatants (data not shown). Affinity purification with protein A followed by SDS-PAGE was used to confirm the purity of the antibodies. When quantified amount of the purified antibodies (10 µg/ml) was re-evaluated using indirect ELISA, all of the 23 antibodies had ELISA signals two times greater than those of phosphate buffered saline (negative control), and were considered as positive or specific to gp350. Of these, five (HB4, HB5, HB7, HB13, and HB14) demonstrated binding affinity equal to or greater than that of the positive control, nAb-72A1 (FIG. 1A). This difference in binding of the 23 antibodies could be due to differential exposure of cognate epitopes on gp350 in the assay performed.

Figure 1B:
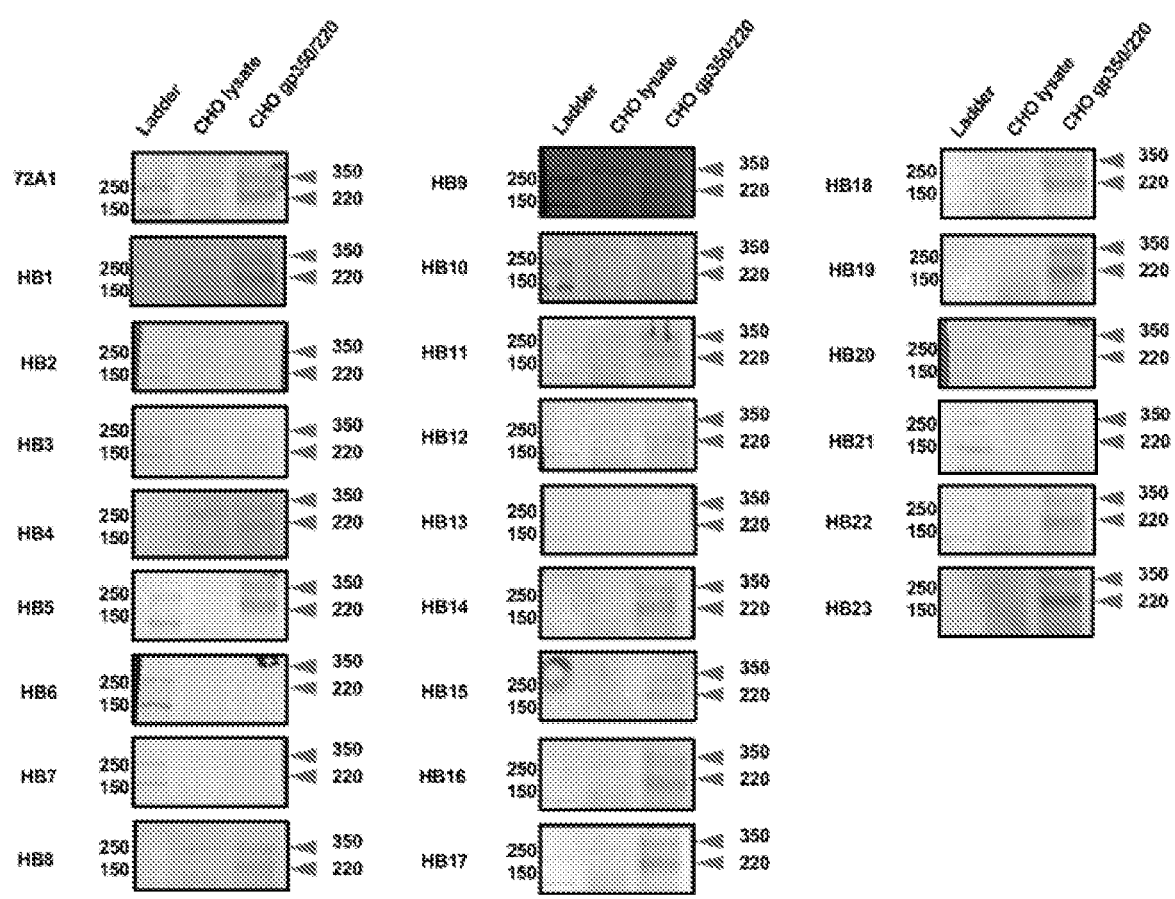
Figure 1C:
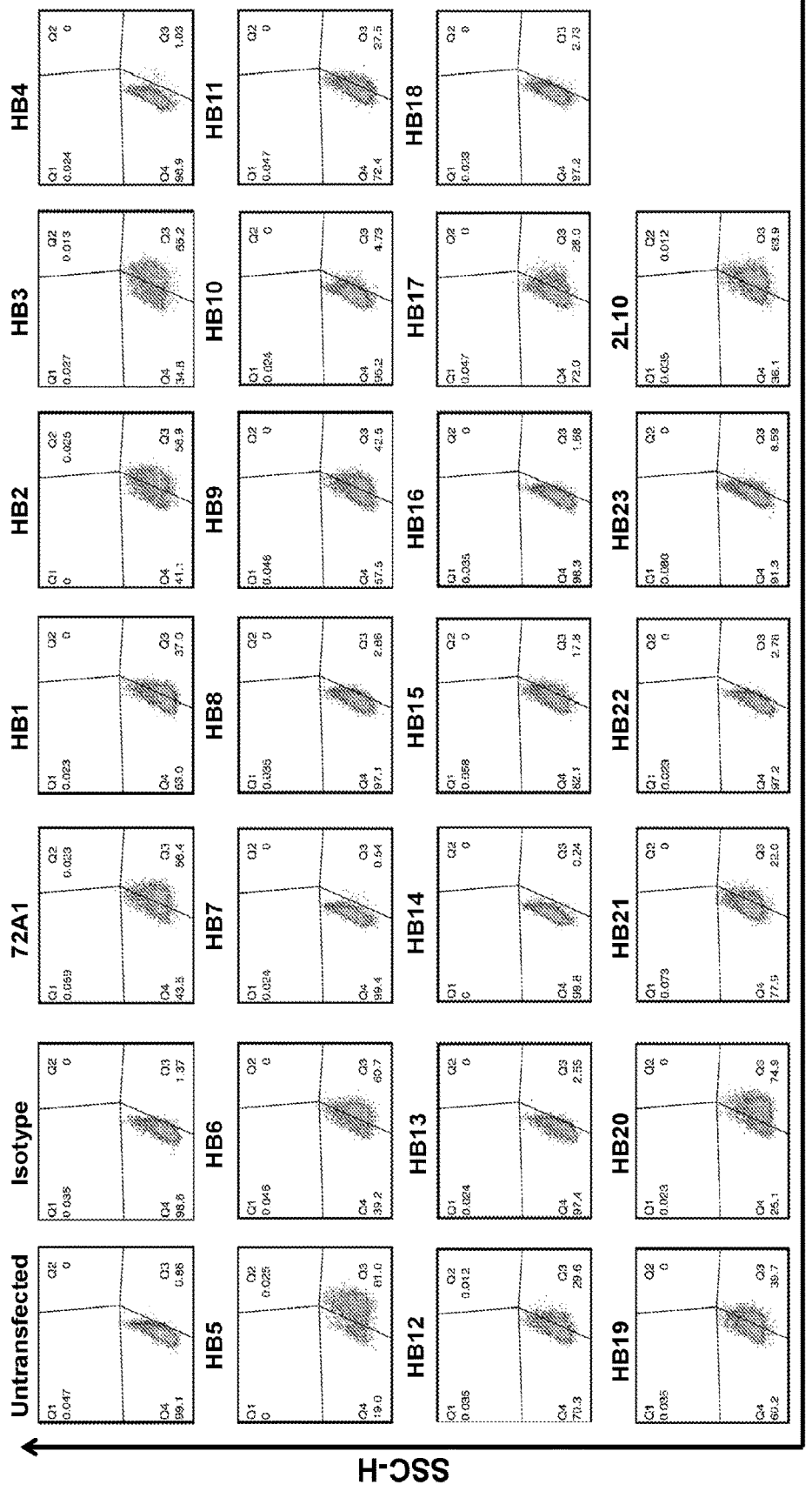
Figure 1D:
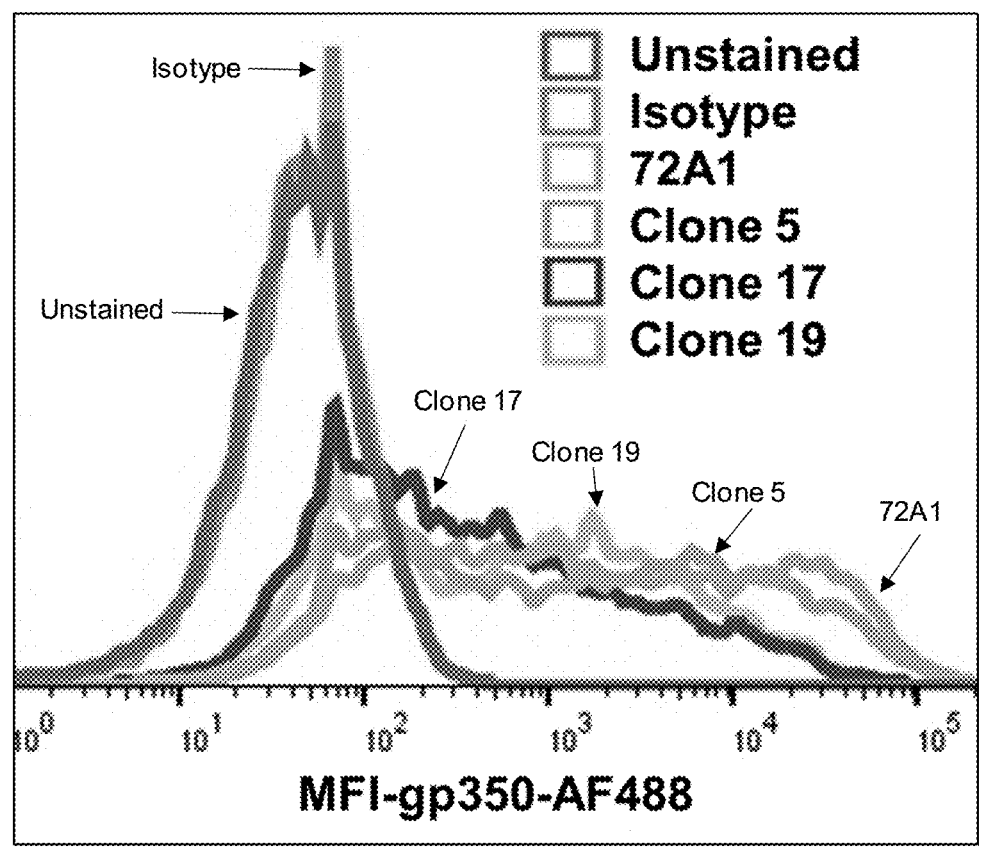

Determining the nature of the binding between an antibody and its target antigen is an important consideration for the performance and specificity of an antibody, as it can involve the recognition of a linear or conformational epitope (49). The antibodies were characterized using immunoblot analysis of denatured gp350 antigen expressed from Chinese hamster ovary (CHO) cells, and 16 of the antibodies reacted to both the 350 kDa and the 220 kDa splice variant. In contrast, HB2, HB3, HB6, HB7, HB13, HB20, and HB21 failed to recognize either of the denatured isoforms of gp350 (FIG. 1B). The antibodies were further characterized by flow cytometric analysis of CHO cells stably expressing gp350 on the cell surface, and HB1, HB2, HB3, HB5, HB6, HB9, HB11, HB12, HB15, HB17, HB19, HB20, and HB21 antibodies readily recognized gp350 (FIGS. 1C, 1D). Given that HB2, HB3, HB20, and HB21 detected gp350 by flow cytometry, but not by immunoblot, suggests that these four antibodies recognized conformational epitopes on gp350, whereas HB5, HB9, HB11, HB15, HB17, and HB19 recognized both linear and conformational epitopes (FIGS. 1B-1D). The observation that all 23 anti-gp350 antibodies recognized the gp350 antigen either by indirect ELISA, flow cytometry, or immunoblot assay suggests that antibodies that are specific to EBV gp350 protein were successfully produced.

Example 3: Analysis of the Variable Heavy and Variable Light Chain Sequences

Figure 2A:
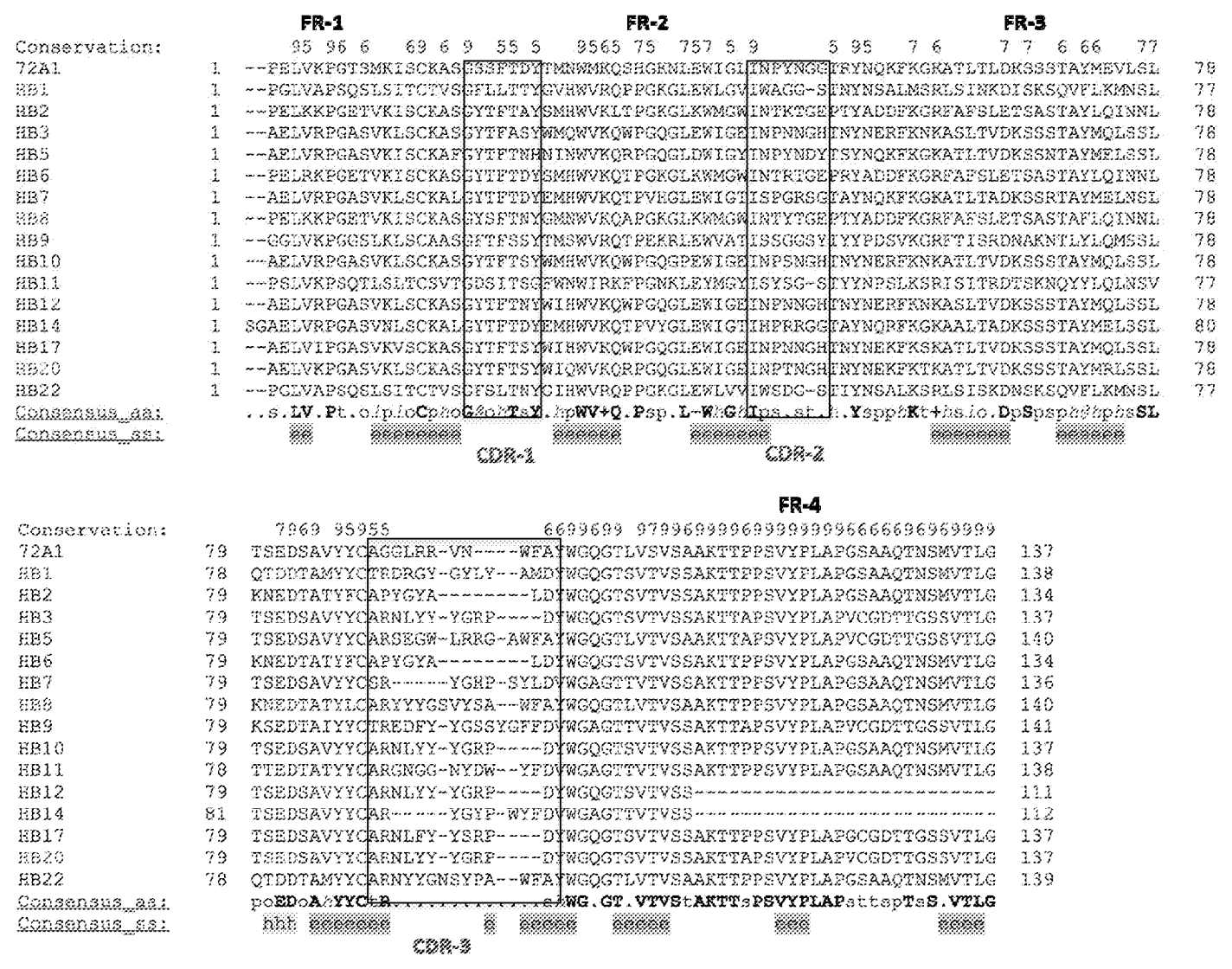
Figure 2B:
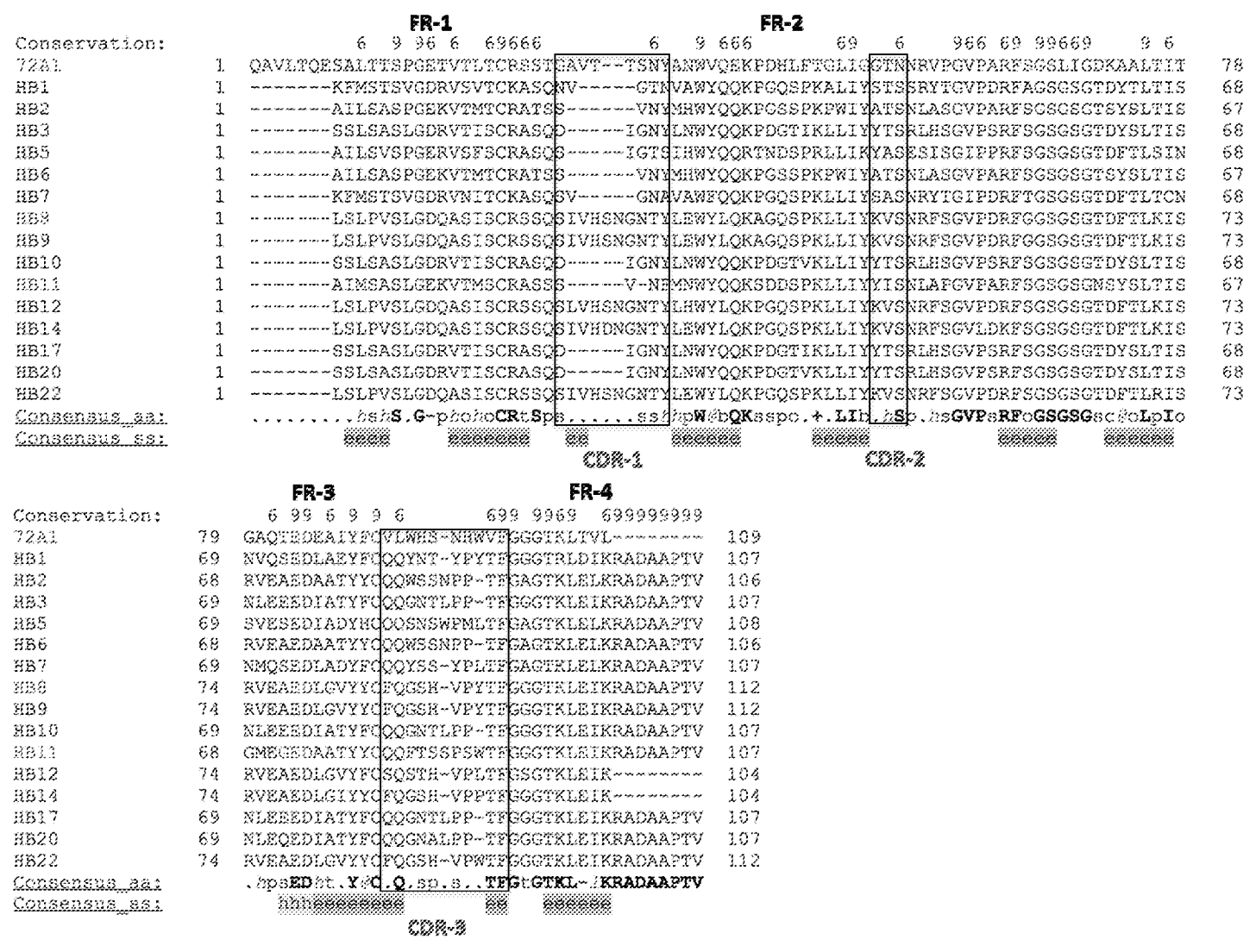

The complementarity determining regions (CDRs) of the anti-gp350 mAbs were sequenced by amplifying mRNA representing unique heavy/light variable chain sequences using RT-PCR. RT-PCR products were sequenced and analyzed. The sequences of the heavy and light chain variable region genes (VH and VL, respectively) of the 23 new anti-gp350 antibodies, as well as the nAb-72A1, were determined and compared the sequences to published nAb-72A1 sequences (50, 51). The sequence of the CDR of this antibody was recently determined and published, revealing two unique IgG1 heavy chains and two unique light chains, one kappa and one lambda (50, 51). PCR was used to amplify the genes encoding the VH and VL chain regions in cDNA generated from the 23 hybridoma cells as well as from HB168 (nAb-72A1). The PCR products presented distinct bands at approximately 350-400 bp and 450-500 bp for VH and VL, respectively (data not shown). The purified fragments were sequenced using Illumina MiSeq, followed by in silico analysis and CDRs for both VH and VL were identified (FIGS. 2A, 2B). Two VH and VL sequences of nAb-72A1 were identified as >94% identical to the previously published sequences (50), suggesting that nAb-72A1 exists as a mixed antibody, instead of the reported mAb (51). Similar to nAb-72A1, HB4, HB13, HB15, and HB23 hybridomas each produced a mixture of two antibodies, with unique sequences of the VH chain showing at >5% frequencies, suggesting that they are not mAbs (Table 3). Coding sequences for VL chains for HB7, HB9, and HB17 were unable to be identified, unless the frequencies were lowered to >1% (Table 3); in this case, the identified coding VL chain sequences were identical.

TABLE 3

Summary of Illumina Dual Demultiplex of $V_H$ and $V_L$ Regions

| Sample | Chain | Starting Pairs | PEAR Merged Reads | Length Filtered Reads | Primer Matched Reads | 3x Reads | >5% Unique Coding | >5% Unique Non-Coding |
|--------|-------|----------------|-------------------|----------------------|---------------------|----------|-------------------|----------------------|
| HB1 | HEAVY | 51,641 | 51,210 | 46,655 | 32,482 | 22,725 | 1 | 0 |
|  | LIGHT | 280,048 | 279,012 | 100,725 | 68,041 | 58,570 | 1 | 1 |
| HB2 | HEAVY | 22,793 | 22,621 | 16,475 | 11,415 | 7,429 | 1 | 0 |
|  | LIGHT | 167,230 | 166,496 | 161,764 | 132,752 | 115,886 | 1 | 1 |
| HB3 | HEAVY | 26,382 | 26,162 | 25,542 | 16,910 | 11,709 | 1 | 0 |
|  | LIGHT | 12,681 | 12,609 | 11,753 | 9,809 | 8,023 | 1 | 1 |
| HB4 | HEAVY | 38,811 | 38,238 | 17,151 | 11,957 | 7,217 | 2 | 0 § |
|  | LIGHT | 179,249 | 129,752 | 111,996 | 78,392 | 66,419 | 1 | 1 |
| HB.5 | HEAVY | 42,951 | 42,173 | 35,793 | 25,842 | 17,173 | 1 | 0 |
|  | LIGHT | 176,073 | 175,267 | 168,806 | 141,712 | 127,045 | 1 | 1 |
| HB6 | HEAVY | 26,142 | 25,981 | 22,245 | 15,658 | 10,453 | 1 | 0 |
|  | LIGHT | 171,996 | 171,370 | 167,730 | 138,348 | 122,397 | 1 | 1 |

TABLE 3-continued

Summary of Illumina Dual Demultiplex of $V_H$ and $V_L$ Regions

| Sample | Chain | Starting Pairs | PEAR Merged Reads | Length Filtered Reads | Primer Matched Reads | 3x Reads | >5% Unique Coding | >5% Unique Non-Coding | |
|---|---|---|---|---|---|---|---|---|---|
| HB7 | HEAVY | 32,443 | 32,094 | 25,449 | 17,615 | 11,836 | 1 | 0 | |
|  | LIGHT | 67,031 | 63,924 | 37,344 | 26,271 | 22,378 | 1 | 1 | * |
| HB8 | HEAVY | 140,091 | 103,349 | 92,744 | 58,292 | 31,583 | 1 | 0 | |
|  | LIGHT | 151,244 | 115,527 | 102,439 | 82,154 | 70,803 | 1 | 1 | |
| HB9 | HEAVY | 37,057 | 36,473 | 19,544 | 11,585 | 7,358 | 1 | 0 | |
|  | LIGHT | 409,432 | 310,529 | 136,074 | 106,820 | 90,063 | 1 | 2 | * |
| HB10 | HEAVY | 38,181 | 37,981 | 26,043 | 17,104 | 11,391 | 1 | 0 | |
|  | LIGHT | 114,255 | 112,498 | 106,914 | 84,368 | 75,370 | 1 | 1 | |
| HB11 | HEAVY | 22,225 | 21,841 | 6,956 | 4,408 | 2,465 | 1 | 0 | |
|  | LIGHT | 106,465 | 102,278 | 65,332 | 50,232 | 44,527 | 1 | 0 | |
| HB12 | HEAVY | 83,044 | 82,355 | 46,350 | 30,276 | 20,886 | 1 | 0 | |
|  | LIGHT | 53,098 | 47,336 | 15,823 | 7,560 | 5,845 | 1 | 1 | |
| HB13 | HEAVY | 81,451 | 80,372 | 47,995 | 32,216 | 20,139 | 2 | 0 | § |
|  | LIGHT | 27,314 | 24,774 | 8,987 | 5,457 | 4,104 | 2 | 1 | |
| HB14 | HEAVY | 76,299 | 75,357 | 28,309 | 19,104 | 12,939 | 1 | 0 | |
|  | LIGHT | 153,011 | 149,264 | 48,474 | 29,710 | 25,133 | 1 | 1 | |
| HB.15 | HEAVY | 26,551 | 26,410 | 16,387 | 11,434 | 7,002 | 2 | 0 | § |
|  | LIGHT | 78,525 | 77,778 | 43,509 | 29,504 | 24,731 | 1 | 1 | |
| HB16 | HEAVY | 54,249 | 53,943 | 9,517 | 7,128 | 4,179 | 1 | 0 | |
|  | LIGHT | 42,048 | 40,351 | 30,602 | 22,758 | 18,251 | 2 | 1 | § |
| HB17 | HEAVY | 111,614 | 110,882 | 81,428 | 50,844 | 35,949 | 1 | 0 | |
|  | LIGHT | 102,490 | 100,488 | 83,925 | 65,925 | 57,727 | 1 | 1 | * |
| HB18 | HEAVY | 211,215 | 155,410 | 146,256 | 91,009 | 50,308 | 1 | 0 | |
|  | LIGHT | 212,261 | 161,879 | 155,235 | 123,096 | 105,959 | 1 | 1 | |
| HB19 | HEAVY | 109,692 | 82,221 | 20,546 | 12,587 | 7,274 | 1 | 1 | |
|  | LIGHT | 70,828 | 69,744 | 62,572 | 48,354 | 42,051 | 1 | 1 | |
| HB20 | HEAVY | 15,781 | 15,632 | 12,789 | 7,757 | 4,852 | 1 | 0 | |
|  | LIGHT | 135,527 | 133,208 | 118,513 | 90,717 | 78,701 | 1 | 1 | |
| HB21 | HEAVY | 15,312 | 15,202 | 8,577 | 5,645 | 3,420 | 1 | 0 | |
|  | LIGHT | 102,450 | 100,171 | 89,059 | 68,552 | 60,500 | 1 | 1 | |
| HB22 | HEAVY | 217,959 | 156,488 | 154,008 | 95,755 | 50,245 | 1 | 0 | |
|  | LIGHT | 205,334 | 156,986 | 143,386 | 108,728 | 85,136 | 1 | 0 | |
| HB23 | HEAVY | 196,390 | 143,929 | 123,028 | 71,076 | 39,358 | 2 | 0 | § |
|  | LIGHT | 158,594 | 120,140 | 115,476 | 90,004 | 78,787 | 2 | 0 | |
| 72A1 | HEAVY | 213,480 | 158,199 | 156,215 | 107,395 | 68,486 | 2 | 0 | § |
|  | LIGHT | 187,216 | 140,964 | 132,945 | 105,783 | 91,208 | 1 | 1 | |

* Hybridoma with $V_L$ chain sequences identified with >1% frequency,
§ Hybridoma with more than one unique, plausible-coding $V_H$ chain sequence with >5% frequency.
The term "unique" refers to unique sequence counts (so, identical sequences found in a substantial frequency of merged reads, not necessarily unique compared to other samples).

The analysis and comparison of the VH and VL chain gene sequences of the 23 hybridomas compared to HB168 (nAb-72A1) showed unique sequences within the CDR 1-3 region. Only HB8 and HB18 had identical VH and VL chain gene sequences, suggesting that the two are the same clone isolated separately; therefore, HB18 was excluded from subsequent experiments. One of the two HB15 antibodies had identical VH and VL gene sequences to that of HB10, however based on the previous characterization, the presence of the additional antibody in HB15 was sufficient to confer subtle differences in biochemical characterizations for gp350 between the two antibodies. Thus, based on the sequence analysis (FIG. 2), 15 unique anti-gp350 mAbs were generated, with distinct biochemical and sequence identity from commercially available nAb-72A1.

Example 4: Neutralization Assay

Figure 3A:
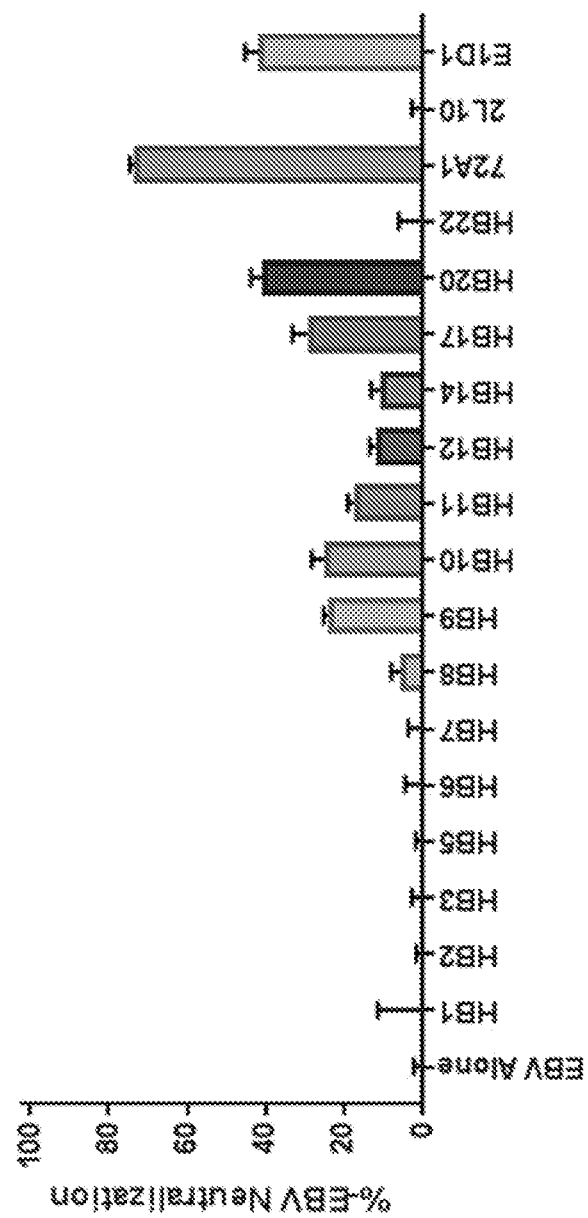
FIGS. 3A and 3B show neutralization activity of novel anti-gp350 mAbs against EBV-eGFP in Raji cells. EBV-eGFP was pre-incubated with 15 anti-gp350 mAbs at 10 µg/ml (FIG. 3A) and 50 µg/ml (FIG. 3B), followed by incubation with Raji cells for 48 h. EBV-eGFP+ cells were enumerated using flow cytometry. Anti-gp350 (nAb-72A1) and anti-gH/gL (E1D1) mAbs served as positive controls and non-neutralizing anti-gp350 (2L10) mAb served as negative control.
Figure 3B:
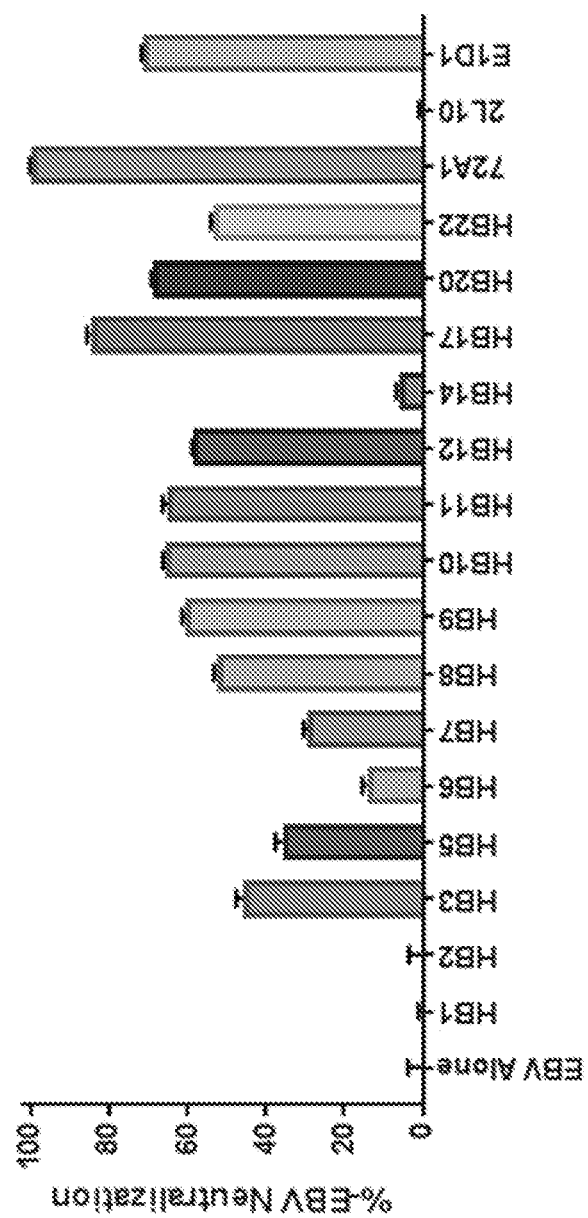

The ability of the 15 mAbs (10 µg/ml or 50 µg/ml) to neutralize purified eGFP-tagged AGS-EBV infection of the Raji B cell line in vitro was evaluated following standardized procedures (52) and determined the percentage of eGFP+ cells using flow cytometry as described (45, 47). The nAbs 72A1 and E1D1 were used as positive controls, whereas the non-neutralizing mAb 2L10 was used as a negative control. Because HB4, HB7, HB13, HB15, HB16, HB19, HB21, and HB23 were confirmed to be mixtures based on isotyping or sequence data, they were eliminated from further consideration in the neutralization assay. An antibody was considered a neutralizer if it inhibited EBV infection >20% at 10 µg/ml and >60% at 50 µg/ml. Several mAbs inhibited EBV infection in a dose-dependent manner. HB20 and HB17 were the most effective at preventing EBV infection of Raji cells in vitro, whereby they reduced infection by 40% and >60%, and >30% and 80% at 10 µg/ml and 50 µg/ml, respectively (FIGS. 3A and 3B). The HB9 and HB10 antibodies prevented EBV infection of Raji cells by ~25% at 10 µg/ml and ~60% at 50 µg/ml. The HB11 antibody neutralized <20% at 10 µg/ml, but showed a dose-dependent increase at 50 µg/ml by neutralizing EBV infection by 60%. By the set neutralization parameters, HB1-3, HB5-8, HB12, HB14, and HB22 did not neutralize EBV infection of Raji cells. In comparison, both nAb-72A1 and nAb-E1D1 neutralized EBV infection by >70% and 40%, respectively, at 10 µg/ml. The nAb-72A1 neutralized EBV infection by >95% at 50 µg/ml, whereas nAb-E1D1 neutralized infection by >60% at 50 µg/ml. As expected, the negative control, mAb-2L10, did not neutralize viral infection at either concentration. Based on the neutralization assay results, the remaining 15 mAbs were organized into two distinct groups, neutralizers (+) and non-neutralizers (−) as summarized in Table 4.

TABLE 4

Summarized Biochemical and Functional Characterizations of Anti-gp350 Antibodies

| Antibody | IgG sub-class | Light chain | ELISA binding to purified EBV gp350/220 | FACS (CHO Cells) | Western blot | Neutralization activity |
|---|---|---|---|---|---|---|
| HB1 | IgG1 | κ | + | + | + | − |
| HB2 | IgG2a | κ | + | + | − | − |
| HB3 | IgG2a | κ | − | + | − | − |
| HB4 | IgG1 | κ | + | − | + | ND |
| HB5 | IgG2a | κ | + | + | + | − |
| HB6 | IgG1 | κ | − | + | − | − |
| HB7 | IgG1 | κ | + | − | − | − |
| HB8 | IgG1 | κ | + | − | + | − |
| HB9 | IgG2a | κ | − | + | + | + |
| HB10 | IgG1 | κ | − | − | + | + |
| HB11 | IgG1 | κ | + | + | + | + |
| HB12 | IgG1 | κ | − | + | + | − |
| HB13 | IgG1 | κ | + | − | − | ND |
| HB14 | IgG1 | κ | + | − | + | − |
| HB15 | IgG1 | κ | + | + | + | ND |
| HB16 | IgG1/IgM | κ | + | − | + | ND |
| HB17 | IgG2b | κ | + | + | + | + |
| HB19 | IgG1/IgM | κ | + | + | + | ND |
| HB20 | IgG2a | κ | − | + | − | + |
| HB21 | IgG1/IgG2b | κ | − | + | − | ND |
| HB22 | IgG1 | κ | − | − | + | − |
| HB23 | IgG1 | κ | − | + | + | ND |
| 72A1 | IgG1 | κ | + | + | + | + |
| E1D1 (anti gH/gL) | IgG1 | κ | − | − | − | + |

ND = Not determined,
+ = positive,
− = negative,
ELISA = enzyme-linked immunosorbent assay,
κ = Kappa.

Example 5: Epitope Mapping

The 15 new anti-gp350 mAbs (neutralizers vs. non-neutralizers) were used to identify most, if not all, of the relevant immunodominant aa residues targeted by both the nAbs and non-nAbs. RepliTope approach was used, in which overlapping peptides [15-mer with 11 aa overlap] that cover the complete sequence of gp350 (aa 1-907) were immobilized on microarray slides and probed with the purified anti-gp350 antibodies in an ELISA format. nAb-72A1 was used as positive control, because the cognate epitopes bound by the antibody have previously been reported.

Two epitopes, $_{253}$TPIPGTGYAYSLRLTPRPVSRFL$_{275}$ and $_{393}$VSGLGTAPKTLIITRTATNATTT$_{415}$, were both bound by all 15 mAbs, as well as nAb-72A1 and 2L10, regardless of their neutralizing or non-neutralizing capabilities. This consensus suggests that these epitopes are immunodominant. Several of the 15 mAbs (HB2, HB3, HB8, HB11, HB12, HB14, HB17, and HB22), as well as nAb-72A1, bound to $_{341}$ANSPNVTVTAFWAWPNNTE$_{359}$. Two epitopes, aa 341-359 and aa 393-415, were found within the previously identified single epitope II, which is encoded by nucleotides between 3,186 bp and 3,528 bp, corresponding to aa 326-439 of gp350 (56). Two mAbs, HB1 and HB10, bound $_{605}$TTPTPNATGPTVGETSPQA$_{623}$, an epitope located within the gp350 (501-699) splice region that is involved in generation of the 220 kDa splice variant. A total of eight mAbs (HB1-3, HB8, HB10-12, and HB22) also bound to the region between $_1$MEAALLVCQYTIQSLIHLT-GEDPG$_{24}$, which includes a region homologous to C3d, another molecule known to interact with CD21 (51, 55). Two epitopes common between most nAbs and non-nAbs, $_{821}$PPSTSSKLRPRWTFTSPPV$_{839}$ and $_{875}$LLLLVMADCAFRRNLSTSHTYTTPPY$_{899}$, were located upstream and downstream, respectively, of the transmembrane domain on the C-terminus of gp350. Epitope aa 821-839 is located within the previously identified epitope I, which is located between aa 733-841 (56). Furthermore, epitope aa 821-839 is potentially involved in EBV infection of B cells (58). However, the study could not identify two epitopes located at aa 282-301 and aa 194-211, which were previously shown to be involved in the binding of nAb-72A1 and CD21, respectively (51, 58, 59). It was shown that nAb-72A1 bound $_{145}$EMQNPVYLIPETVPYIKWDN$_{164}$, one of the neutralizing epitopes on gp350 (51, 58, 59). Nine gp350 epitopes identified by 15 neutralizing and non-neutralizing mAbs are shown in the sequence below and summarized in Table 5). Residues in bold represent the gp220 splice variant region. Residues in boxes represent RepliTope-identified epitopes and exact residues. Italic residues represent canonical neutralizing epitope, underlined residues represent epitope bound by all assayed mAb.

```
  1 MEAALLVCQY TIQSLIHLTG EDPGFFNVEI PEFPFYPTCN VCTADVNVTI NFDVGGKKHQ

61 LDLDFGQLTP HTKAVYQPRG AFGGSENATN LFLLELLGAG ELALTMRSKK LPINVTTGEE

121 QQVSLESVDV YFQDVFGTMW CHHAEMQNPV YLIPETVPYI KWDNCNSTNI TAVVRAQGLD
```

-continued

```
181 VTLPLSLPTS AQDSNFSVKT EMLGNEIDIE CIMEDGEISQ VLPGDNKFNI TCSGYESHVP

241 SGGILTSTSP VATPIPGTGY AYSLRLTPRP VSRFLGNNSI LYVFYSGNGP KASGGDYCIQ

301 SNIVFSDEIP ASQDMPTNTT DITYVGDNAT YSVPMVTSED ANSPNVTVTA FWAWPNNTET

361 DFKCKWTLTS GTPSGCENIS GAFASNRTFD IT/VSGLGTAP KTLIITRTAT NATTTTHKVI

421 FSKAPESTTT SPTLNTTGFA DPNTTTGLPS STHVPTNLTA PASTGPTVST ADVTSPTPAG

481 TTSGASPVTP SPSPWDNGTE SKAPDMTSST SPVTTPTPNA TSPTPAVTTP TPNATSPTPA

541 VTTPTPNATS PTLGKTSPTS AVTTPTPNAT SPTLGKTSPT SAVTTPTPNA TSPTLGKTSP

601 TSAVTTPTPN ATGPTVGETS PQANATNHTL GGTSPTPVVT SQPKNATSAV TTGQHNITSS

661 STSSMSLRPS SNPETLSPST SDNSTSHMPL LTSAHPTGGE NITQVTPASI STHHVSTSSP

721 APRPGTTSQA SGPGNSSTST KPGEVNVTKG TPPQNATSPQ APSGQKTAVP TVTSTGGKAN

781 STTGGKHTTG HGARTSTEPT TDYGGDSTTP RPRYNATTYL PPSTSSKLRP RWTFTSPPVT

841 TAQATVPVPP TSQPRFSNLS MLVLQWASLA VLTLLLLLVM ADCAFRRNLS TSHTYTTPPY

901 DDAETYV
```

TABLE 5

Antibody Binding gp350 Epitopes

| Epitope | Amino acid sequence | Epitope Properties |
|---|---|---|
| 1 | $_1$MEAALLVCQYTIQSLIHLTGEDPG$_{24}$ | |
| 2 | $_{145}$EMQNPVYLIPETVPYIKWDN$_{164}$ | Neutralizing |
| 3 | $_{253}$TPIPGTGYAYSLRLTPRPVSRFL$_{275}$ | Immunodominant/novel |
| 4 | $_{341}$ANSPNVTVTAFWAWPNNTE$_{359}$ | |
| 5 | $_{381}$GAFASNRTFDIT$_{392}$ | Neutralizing/novel |
| 6 | $_{393}$VSGLGTAPKTLIITRTATNATTT$_{415}$ | Immunodominant |
| 7 | $_{605}$TTPTPNATGPTVGETSPQA$_{623}$ | |
| 8 | $_{821}$PPSTSSKLRPRWTFTSPPV$_{839}$ | |
| 9 | $_{875}$LLLLVMADCAFRRNLSTSHTYTTPPY$_{899}$ | novel |

Example 6: Construction of Chimeric Gp350 nAbs

Figure 4:
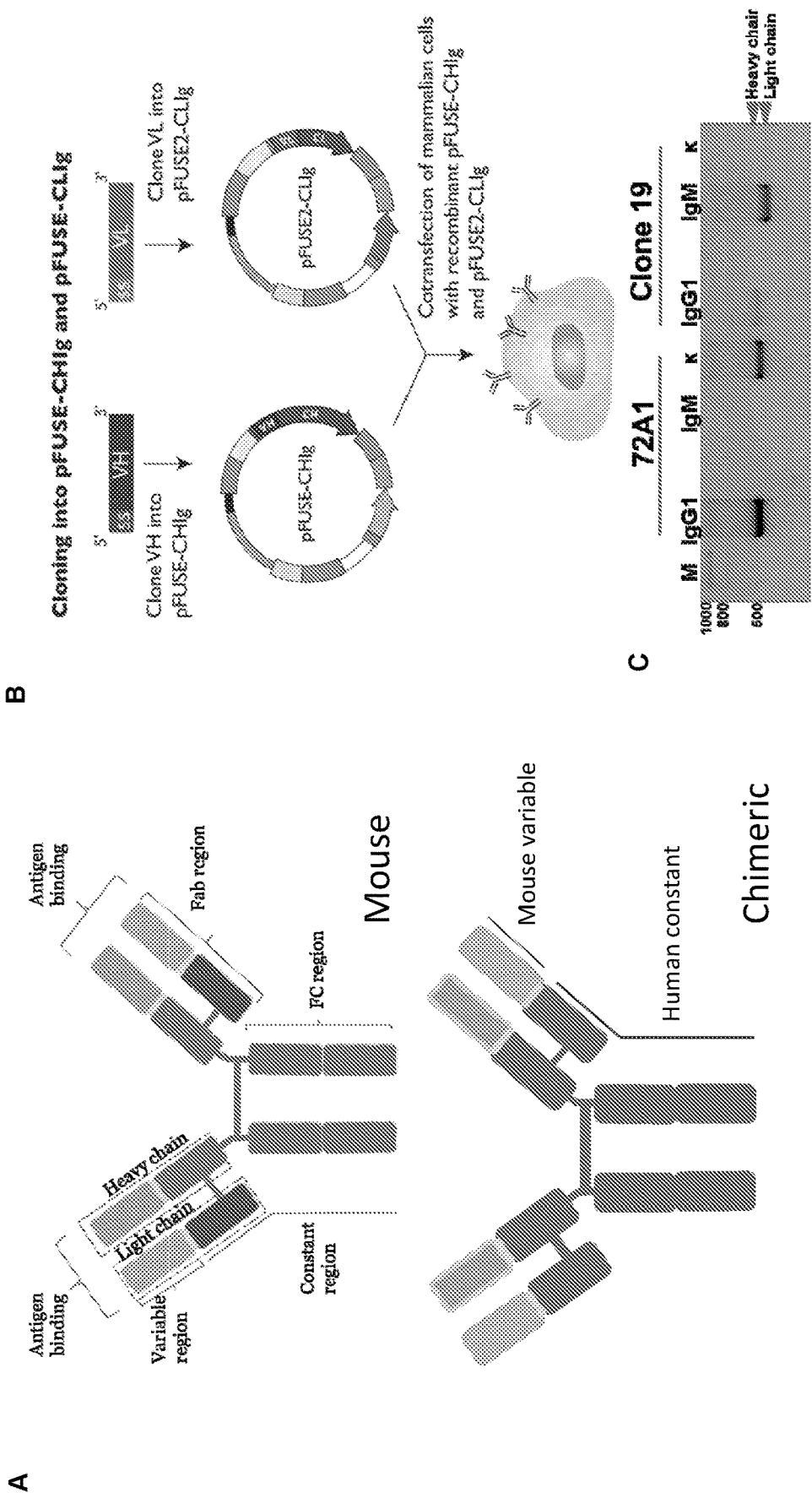
FIGS. 4A-4C show construction of chimeric gp350 nAbs.

Chimeric gp350 nAbs were constructed according to the diagrams of FIG. 4. First, mouse antibodies against human gp350 were developed, and then the mouse antibody variable region is fused to human constant region, for example, to human IgM. The heavy chain and light chain variable regions of the mouse antibody were cloned into pFUSE-CHIg and pFUSE2-CLIg vectors, respectively, followed by co-transfection of mammalian cells with recombinant pFUSE-CHIg and pFUSE2-CLIg vectors. The expression vectors were obtained from InvivoGen, and the expression was conducted in CHO cells or HEK293 cells, available from ATCC. The construction schemes and expression of heavy and light chains of clone 19 are shown in FIG. 4.

Analysis of VH-VL sequence from the HB168 (nAb-72A1) hybridoma revealed that the hybridoma produced two antibodies: one that is gp350-specific and another that recognizes mineral oil-induced plasmacytoma (MOPC) (57). To further investigate gp350 for additional neutralizing epitopes, the gp350-specific nAb-72A1 VH-VL sequence was used to generate chimeric (mouse/human) recombinant antibodies. Similarly, the VH-VL sequence for the HB20 antibody, which the neutralization analysis above showed to be one of the best nAb, was used to generate chimeric antibody. A negative control chimeric recombinant antibody was generated using VH-VL sequences from the gp350-specific but non-neutralizing HB5 antibody mentioned above (FIG. 3).

Comparative analysis of the epitope binding pattern was performed using the chimeric recombinant antibodies and a novel epitope was revealed, $_{381}$GAFASNRTFDIT$_{392}$, which was bound by HB20 and nAb-72A1, but not by HB5, and is distinct from the $_{145}$EMQNPVYLIPETVPYIKWDN$_{164}$ epitope, which is bound only by the nAb-72A1. The sequence below shows the novel gp350-neutralizing epitope identified by epitope mapping of neutralizing (nAb-72A1 and HB20) vs non-neutralizing (HB5) anti-gp350 mAbs. Epitopes bound by nAb-72A1 (double underlined), HB20 (wavy underlined), and HB5 (boxed) are indicated. Residues 501-700 represent splice variant region (bold), single underlined residues represent epitopes bound by nAb-72A1, HB20 and HB5, and italic residues represent epitopes bound by nAbs.

```
  1 MEAALLVCQY TIQSLIHLTG EDPGFFNVEI PEFPFYPTCN VCTADVNVTI NFDVGGKKHQ

61 LDLDFGQLTP HTKAVYQPRG AFGGSENATN LFLLELLGAG ELALTMRSKK LPINVTTGEE

121 QQVSLESVDV YFQDVFGTMW CHHAEMQNPV YLIPETVPYI KWDNCNSTNI TAVVRAQGLD
```

```
181 VTLPLSLPTS AQDSNFSVKT EMLGNEIDIE CIMEDGEISQ VLPGDNKFNI TCSGYESHVP

241 SGGILTSTSP VATPIPGTGY AYSLRLTPRP VSRFLGNNSI LYVFYSGNGP KASGGDYCIQ

301 SNIVFSDEIP ASQDMPTNTT DITYVGDNAT YSVPMVTSED ANSPNVTVTA FWAWPNNTET

361 DFKCKWTLTS GTPSGCENIS GAFASNETED ITVSGLGTAP KTLIITRTAT NATTTHKVI

421 FSKAPESTTT SPTLNTTGFA DPNTTTGLPS STHVPTNLTA PASTGPTVST ADVTSPTPAG

481 TTSGASPVTP SPSPWDNGTE SKAPDMTSST SPVTTPTPNA TSPTPAVTTP TPNATSPTPA

541 VTTPTPNATS PTLGKTSPTS AVTTPTPNAT SPTLGKTSPT SAVTTPTPNA TSPTLGKTSP

601 TSAVTTPTPN ATGPTVGETS PQANATNHTL GGTSPTPVVT SQPKNATSAV TTGQHNITSS

661 STSSMSLRPS SNPETLSPST SDNSTSHMPL LTSAHPTGGE NITQVTPASI STHHVSTSSP

721 APRPGTTSQA SGPGNSSTST KPGEVNVTKG TPPQNATSPQ APSGQKTAVP TVTSTGGKAN

781 STTGGKHTTG HGARTSTEPT TDYGGDSTTP RPRYNATTYL PPSTSSKLRP RWTFTSPPVT

841 TAQATVPVPP TSQPRFSNLS MLVLQWASLA VLTLLLLLVM ADCAFRRNLS TSHTYTTPPY

901 DDAETYV
```

Example 7: Development of Antibody-Small Molecule Conjugates (ADCs)

Figure 5:
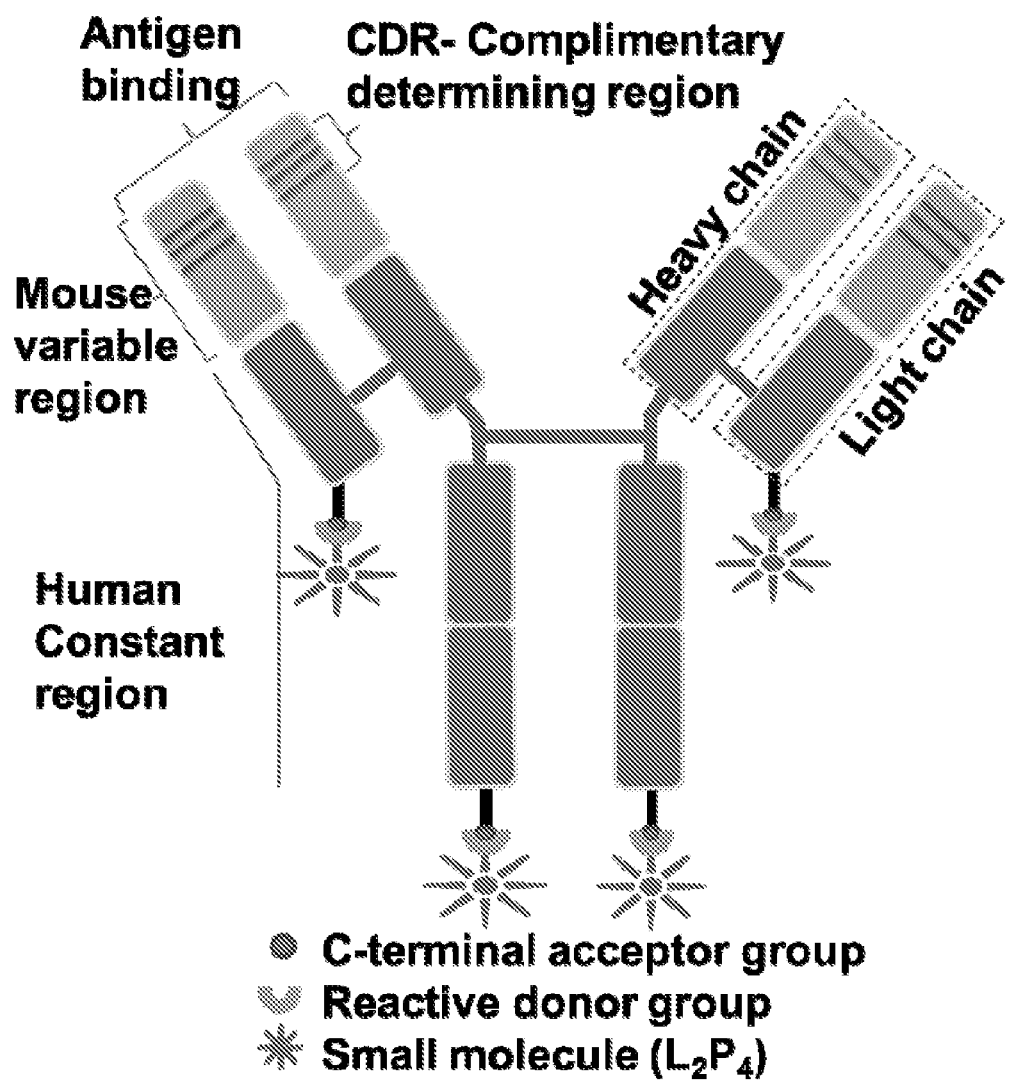
FIG. 5 illustrates an antibody-L2P4 conjugate.

Using small molecule $L_2P_4$ as an example, antibody-small molecule conjugates can be developed as illustrated in FIG. 5. One or more small molecules can be conjugated to the antibody heavy chain or light chain via a reactive donor group and a C-terminal acceptor group. Small molecule $L_2P_4$ was disclosed in the publication by Jiang et al.[40] After validating the function of the purified chimeric gp350 nAbs using ELISA, flow cytometry (FC), and surface plasmon resonance, the nAbs can be conjugated to $L_2P_4$ in a site-specific manner via a Val-Cit dipeptide linker, which releases the active agent upon internalization of the ADC.[41,42]

Example 8: Efficacy Test of ADCs

To screen for optimal dose and identify the best nAb clone for pre-clinical studies, the ability of the ADC to neutralize EBV in vitro and to protect against PTLD in vivo is tested using a humanized mouse, as described[43,44]. In brief, purified chimeric ADC (or controls: PBS, or isotype-matched non-nAbs) is injected by I.V. into humanized mice, followed by EBV-B95-8-eGFP challenge. Mice are monitored regularly and euthanized upon signs of illness or after a preset limit of 100 days. Routine histology and necropsy are conducted to assess the efficacy of the ADC to protect against EBV infection and PTLD development.

REFERENCES

The references listed below, and all references cited in the specification are hereby incorporated by reference in their entireties, as if fully set forth herein.

1. Rickinson A B, Kieff E. Epstein-Barr Virus. In: Knipe D M, Howley P M, eds. Fields Virology. Philadelphia: Lippiincott, Williams & Wilkins; 2007:2680-2700.
2. Goedert J J, Cote T R, Virgo P, et al. Spectrum of AIDS-associated malignant disorders. Lancet 1998; 351:1833-9.
3. Coté T R, Biggar R J, Rosenberg P S, et al. Non-Hodgkin's lymphoma among people with AIDS: Incidence, presentation and public health burden. International Journal of Cancer 1998; 73:645-50.
4. Benkerrou M, Jais J P, Leblond V, et al. Anti-B-cell monoclonal antibody treatment of severe posttransplant B-lymphoproliferative disorder: prognostic factors and long-term outcome. Blood 1998; 92:3137-47.
5. Cruz R J, Jr., Ramachandra S, Sasatomi E, et al. Surgical management of gastrointestinal posttransplant lymphoproliferative disorders in liver transplant recipients. Transplantation 2012; 94:417-23.
6. Faro A, Kurland G, Michaels M G, et al. Interferon-alpha affects the immune response in post-transplant lymphoproliferative disorder. Am J Respir Crit Care Med 1996; 153:1442-7.
7. Milpied N, Vasseur B, Parquet N, et al. Humanized anti-CD20 monoclonal antibody (Rituximab) in post transplant B-lymphoproliferative disorder: a retrospective analysis on 32 patients. Ann Oncol 2000; 11 Suppl 1:113-6.
8. Papadopoulos E B, Ladanyi M, Emanuel D, et al. Infusions of donor leukocytes to treat Epstein-Barr virus-associated lymphoproliferative disorders after allogeneic bone marrow transplantation. N Engl J Med 1994; 330: 1185-91.
9. Starzl T E, Holmes J H. Experience in renal transplantation. 1964.
10. Stamatatos L, Morris L, Burton D R, Mascola J R. Neutralizing antibodies generated during natural HIV-1 infection: good news for an HIV-1 vaccine? Nature medicine 2009; 15:866-70.
11. Walker L M, Phogat S K, Chan-Hui P-Y, et al. Broad and potent neutralizing antibodies from an African donor reveal a new HIV-1 vaccine target. Science 2009; 326: 285-9.
12. Sui J, Hwang W C, Perez S, et al. Structural and functional bases for broad-spectrum neutralization of avian and human influenza A viruses. Nature structural & molecular biology 2009; 16:265-73.
13. Han T, Marasco W A. Structural basis of influenza virus neutralization. Annals of the New York Academy of Sciences 2011; 1217:178-90.
14. Wrammert J, Smith K, Miller J, et al. Rapid cloning of high-affinity human monoclonal antibodies against influenza virus. Nature 2008; 453:667-71.

15. Piedimonte G, King K A, Holmgren N L, Bertrand P J, Rodriguez M M, Hirsch R L. A humanized monoclonal antibody against respiratory syncytial virus (palivizumab) inhibits RSV-induced neurogenic-mediated inflammation in rat airways. Pediatr Res 2000; 47:351-6.
16. Glotz D, Chapman J R, Dharnidharka V R, et al. The seville expert workshop for progress in posttransplant lymphoproliferative disorders. Transplantation 2012; 94: 784-93.
17. Connolly S A, Jackson J O, Jardetzky T S, Longnecker R. Fusing structure and function: a structural view of the herpesvirus entry machinery: A structural view of herpesvirus entry machinery. Nat Rev Microbiol 2011; 9:369-81.
18. Eisenberg R J, Atanasiu D, Cairns T M, Gallagher J R, Krummenacher C, Cohen G H. Herpes virus fusion and entry: a story with many characters. Viruses 2012; 4:800-32.
19. Henle G, Henle W, Diehl V. Relation of Burkitt's tumor-associated herpes-type virus to infectious mononucleosis. Proceedings of the National Academy of Sciences of the United States of America 1968; 59:94.
20. Cohen J I, Fauci A S, Varmus H, Nabel G J. Epstein-Barr Virus: An Important Vaccine Target for Cancer Prevention. Science Translational Medicine 2011; 3:107fs7-fs7.
21. Khanna R, Sherritt M, Burrows S R. EBV structural antigens, gp350 and gp85, as targets for ex vivo virus-specific CTL during acute infectious mononucleosis: potential use of gp350/gp85 CTL epitopes for vaccine design. The Journal of Immunology 1999; 162:3063-9.
22. Thorley-Lawson D A, Geilinger K. Monoclonal antibodies against the major glycoprotein (gp350/220) of Epstein-Barr virus neutralize infectivity. Proceedings of the National Academy of Sciences of the United States of America 1980; 77:5307-11.
23. Perez E M, Foley J, Tison T, Silva R, Ogembo J G. Novel Epstein-Barr virus-like particles incorporating gH/gL-EBNA1 or gB-LMP2 induce high neutralizing antibody titers and EBV-specific T-cell responses in immunized mice. Oncotarget 2016.
24. Cohen J I. Epstein-barr virus vaccines. Clin Transl Immunology 2015; 4:e32.
25. Biggar R J, Henle W, Fleisher G, Böcker J, Lennette E T, Henle G. Primary Epstein-Barr virus infections in african infants. I. Decline of maternal antibodies and time of infection. International Journal of Cancer 1978; 22:239-43.
26. Biggar R J, Henle G, Böcker J, Lennette E T, Fleisher G, Henle W. Primary Epstein-Barr virus infections in African infants. II. Clinical and serological observations during seroconversion. International Journal of Cancer 1978; 22:244-50.
27. Mold C, Bradt B, Nemerow G, Cooper N. Activation of the alternative complement pathway by EBV and the viral envelope glycoprotein, gp350. The Journal of Immunology 1988; 140:3867-74.
28. Khyatti M, Patel P C, Stefanescu I, Menezes J. Epstein-Barr virus (EBV) glycoprotein gp350 expressed on transfected cells resistant to natural killer cell activity serves as a target antigen for EBV-specific antibody-dependent cellular cytotoxicity. Journal of virology 1991; 65:996-1001.
29. Finerty S, Mackett M, Arrand J R, Watkins P E, Tarlton J, Morgan A J. Immunization of cottontop tamarins and rabbits with a candidate vaccine against the Epstein-Barr virus based on the major viral envelope glycoprotein gp340 and alum. Vaccine 1994; 12:1180-4.
30. Gu S Y, Huang T M, Ruan L, et al. First EBV vaccine trial in humans using recombinant vaccinia virus expressing the major membrane antigen. Dev Biol Stand 1995; 84:171-7.
31. Mok H, Cheng X, Xu Q, et al. Evaluation of Measles Vaccine Virus as a Vector to Deliver Respiratory Syncytial Virus Fusion Protein or Epstein-Barr Virus Glycoprotein gp350. Open Virol J 2012; 6:12-22.
32. Moutschen M, Leonard P, Sokal E M, et al. Phase I/II studies to evaluate safety and immunogenicity of a recombinant gp350 Epstein-Barr virus vaccine in healthy adults. Vaccine 2007; 25:4697-705.
33. Sokal E M, Hoppenbrouwers K, Vandermeulen C, et al. Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults. Journal of Infectious Diseases 2007; 196:1749-53.
34. Rees L, Tizard E J, Morgan A J, et al. A phase I trial of epstein-barr virus gp350 vaccine for children with chronic kidney disease awaiting transplantation. Transplantation 2009; 88:1025-9.
35. Hague T, Johannessen I, Dombagoda D, et al. A mouse monoclonal antibody against Epstein-Barr virus envelope glycoprotein 350 prevents infection both in vitro and in vivo. J Infect Dis 2006; 194:584-7.
36. Ferrara N, Hillan K J, Gerber H-P, Novotny W. Discovery and development of bevacizumab, an anti-VEGF antibody for treating cancer. Nat Rev Drug Discov 2004; 3:391-400.
37. Hudis C A. Trastuzumab—Mechanism of Action and Use in Clinical Practice. New England Journal of Medicine 2007; 357:39-51.
38. Jonker D J, O'Callaghan C J, Karapetis C S, et al. Cetuximab for the Treatment of Colorectal Cancer. New England Journal of Medicine 2007; 357:2040-8.
39. Dzeng R K, Jha H C, Lu J, Saha A, Banerjee S, Robertson E S. Small molecule growth inhibitors of human oncogenic gammaherpesvirus infected B-cells. Mol Oncol 2015; 9:365-76.
40. Jiang L, Lan R, Huang T, et al. EBNA1-targeted probe for the imaging and growth inhibition of tumours associated with the Epstein-Barr virus. Nature Biomedical Engineering 2017; 1:0042.
41. Dubowchik G M, Firestone R A. Cathepsin B-sensitive dipeptide prodrugs. A model study of structural requirements for efficient release of doxorubicin. Bioorganic & medicinal chemistry letters 1998; 8:3341-6.
42. Senter P D, Sievers E L. The discovery and development of brentuximab vedotin for use in relapsed Hodgkin lymphoma and systemic anaplastic large cell lymphoma. Nature biotechnology 2012; 30:631-7.
43. Hague T, Johannessen I, Dombagoda D, et al. A mouse monoclonal antibody against Epstein-Barr virus envelope glycoprotein 350 prevents infection both in vitro and in vivo. J Infect Dis 2006; 194:584-7.
44. Jangalwe S, Shultz L D, Mathew A, Brehm M A. Improved B cell development in humanized NOD-scid IL2Rgammanull mice transgenically expressing human stem cell factor, granulocyte-macrophage colony-stimulating factor and interleukin-3. Immun Inflamm Dis 2016; 4:427-40.
45. Ogembo J G, Kannan L, Ghiran I, Nicholson-Weller A, Finberg R W, Tsokos G C, Fingeroth J D. 2013. Human complement receptor type 1/CD35 is an Epstein-Barr Virus receptor. Cell Rep 3:371-385.

46. Speck P, Longnecker R. 1999. Epstein-Barr virus (EBV) infection visualized by EGFP expression demonstrates dependence on known mediators of EBV entry. Arch Virol 144:1123-1137.
47. Ogembo J G, Muraswki M R, McGinnes L W, Parcharidou A, Sutiwisesak R, Tison T, Avendano J, Agnani D, Finberg R W, Morrison T G. 2015. A chimeric EBV gp350/220-based VLP replicates the virion B-cell attachment mechanism and elicits long-lasting neutralizing antibodies in mice. Journal of Translational Medicine 13:50.
48. Jones S T, Bendig M M. 1991. Rapid PCR-cloning of full-length mouse immunoglobulin variable regions. Biotechnology (N Y) 9:579.
49. Sela M, Schechter B, Schechter I, Borek F. 1967. Antibodies to Sequential and Conformational Determinants. Cold Spring Harbor Symposia on Quantitative Biology 32:537-545.
50. Herrman M, Muhe J, Quink C, Wang F. 2015. Epstein-Barr Virus gp350 Can Functionally Replace the Rhesus Lymphocryptovirus Major Membrane Glycoprotein and Does Not Restrict Infection of Rhesus Macaques. J Virol 90:1222-1230.
51. Tanner J E, Coincon M, Leblond V, Hu J, Fang J M, Sygusch J, Alfieri C. 2015. Peptides designed to spatially depict the Epstein-Barr virus major virion glycoprotein gp350 neutralization epitope elicit antibodies that block virus-neutralizing antibody 72A1 interaction with the native gp350 molecule. J Virol 89:4932-4941.
52. Sashihara J, Burbelo P D, Savoldo B, Pierson T C, Cohen J I. 2009. Human antibody titers to Epstein-Barr Virus (EBV) gp350 correlate with neutralization of infectivity better than antibody titers to EBV gp42 using a rapid flow cytometry-based EBV neutralization assay. Virology 391: 249-256.
53. Qualtiere L F, Decoteau J F, Hassan Nasr-el-Din M. 1987. Epitope mapping of the major Epstein-Barr virus outer envelope glycoprotein gp350/220. J Gen Virol 68 (Pt 2):535-543.
54. Nemerow G R, Mold C, Schwend V K, Tollefson V, Cooper N R. 1987. Identification of Gp350 as the Viral Glycoprotein Mediating Attachment of Epstein-Barr-Virus (Ebv) to the Ebv/C3d Receptor of B-Cells—Sequence Homology of Gp350 and C3-Complement Fragment C3d. Journal of Virology 61:1416-1420.
55. Nemerow G R, Houghten R A, Moore M D, Cooper N R. 1989. Identification of an epitope in the major envelope protein of Epstein-Barr virus that mediates viral binding to the B lymphocyte EBV receptor (CR2). Cell 56:369-377.
56. Zhang P F, Klutch M, Armstrong G, Qualtiere L, Pearson G, Marcus-Sekura C J. 1991. Mapping of the epitopes of Epstein-Barr virus gp350 using monoclonal antibodies and recombinant proteins expressed in *Escherichia coli* defines three antigenic determinants. J Gen Virol 72 (Pt 11):2747-2755.
57. Tanner J, Whang Y, Sample J, Sears A, Kieff E. 1988. Soluble gp350/220 and deletion mutant glycoproteins block Epstein-Barr virus adsorption to lymphocytes. J Virol 62:4452-4464.
58. Urquiza M, Lopez R, Patino H, Rosas J E, Patarroyo M E. 2005. Identification of three gp350/220 regions involved in Epstein-Barr virus invasion of host cells. J Biol Chem 280:35598-35605.
59. Szakonyi G, Klein M G, Hannan J P, Young K A, Ma R Z, Asokan R, Holers V M, Chen X S. 2006. Structure of the Epstein-Barr virus major envelope glycoprotein. Nat Struct Mol Biol 13:996-1001.
60. Sitompul L S, Widodo N, Djati M S, Utomo D H. 2012. Epitope mapping of gp350/220 conserved domain of epstein barr virus to develop nasopharyngeal carcinoma (npc) vaccine. Bioinformation 8:479-482.
61. Balfour H H, Jr. 2014. Progress, prospects, and problems in Epstein-Barr virus vaccine development. Curr Opin Virol 6C:1-5.
62. Henle G, Henle W. 1979. The virus as the etiologic agent of infectious mononucleosis, p 297-320, The Epstein-Barr Virus. Springer.
63. Luzuriaga K, Sullivan J L. 2010. Infectious mononucleosis. N Engl J Med 362:1993-2000.
64. Cui X, Cao Z, Chen Q, Arjunaraja S, Snow A L, Snapper C M. 2016. Rabbits immunized with Epstein-Barr virus gH/gL or gB recombinant proteins elicit higher serum virus neutralizing activity than gp350. Vaccine.
65. Fingeroth J D, Weis J J, Tedder T F, Strom inger J L, Biro P A, Fearon D T. 1984. Epstein-Barr virus receptor of human B lymphocytes is the C3d receptor CR2. Proc Natl Acad Sci USA 81:4510-4514.
66. Tanner J, Weis J, Fearon D, Whang Y, Kieff E. 1987. Epstein-Barr virus gp350/220 binding to the B lymphocyte C3d receptor mediates adsorption, capping, and endocytosis. Cell 50:203-213.
67. Weiss E R, Alter G, Ogembo J G, Henderson J L, Tabak B, Bakis Y, Somasundaran M, Garber M, Selin L, Luzuriaga K. 2017. High Epstein-Barr Virus Load and Genomic Diversity Are Associated with Generation of gp350-Specific Neutralizing Antibodies following Acute Infectious Mononucleosis. J Virol 91.
68. Hoffman G J, Lazarowitz S G, Hayward S D. 1980. Monoclonal antibody against a 250,000-dalton glycoprotein of Epstein-Barr virus identifies a membrane antigen and a neutralizing antigen. Proc Natl Acad Sci USA 77:2979-2983.
69. Thorley-Lawson D A, Geilinger K. 1980. Monoclonal antibodies against the major glycoprotein (gp350/220) of Epstein-Barr virus neutralize infectivity. Proc Natl Acad Sci USA 77:5307-5311.
70. Alfarano C, Andrade C E, Anthony K, Bahroos N, Bajec M, Bantoft K, Betel D, Bobechko B, Boutilier K, Burgess E, Buzadzija K, Cavero R, D'Abreo C, Donaldson I, Dorairajoo D, Dumontier M J, Dumontier M R, Earles V, Farrall R, Feldman H, Garderman E, Gong Y, Gonzaga R, Grytsan V, Gryz E, Gu V, Haldorsen E, Halupa A, Haw R, Hrvojic A, Hurrell L, Isserlin R, Jack F, Juma F, Khan A, Kon T, Konopinsky S, Le V, Lee E, Ling S, Magidin M, Moniakis J, Montojo J, Moore S, Muskat B, Ng I, Paraiso J P, Parker B, Pintilie G, Pirone R, et al. 2005. The Biomolecular Interaction Network Database and related tools 2005 update. Nucleic Acids Res 33:D418-424.

The invention claimed is:

1. An antibody or an immunogenic fragment thereof comprising a VH region comprising CDR1 having an amino acid sequence selected from the group consisting of SEQ ID NOs: 4-19, CDR2 having an amino acid sequence selected from the group consisting of SEQ ID NOs: 20-35, and CDR3 having an amino acid sequence selected from the group consisting of SEQ ID NOs: 36-51.

2. The antibody or the immunogenic fragment thereof of claim 1, further comprising a VL region comprising CDR1 having an amino acid sequence selected from the group consisting of SEQ ID NOs: 52-67, CDR2 having an amino acid sequence selected from the group consisting of SEQ ID NOs: 68-83, and CDR3 having an amino acid sequence selected from the group consisting of SEQ ID NOs: 84-99.

3. The antibody of claim 1, wherein the antibody is a monoclonal antibody.

4. The antibody of claim 1, wherein the antibody is a chimeric antibody, a humanized antibody or a human antibody.

5. An antibody-small molecule conjugate comprising:
   the antibody or an immunogenic fragment thereof of claim 1; and
   a small molecule having an anti-proliferative activity against EBV-transformed cells,
   wherein the small molecule is conjugated to the antibody.

6. The conjugate of claim 5, wherein the antibody is a monoclonal antibody, a chimeric antibody, a humanized antibody, or a human antibody.

7. The conjugate of claim 5, wherein the small molecule is a growth inhibitor of EBV infected B cells, L2P4, 2-butynediamide, or a derivative thereof.

8. The conjugate of claim 5, wherein the small molecule is conjugated to the antibody via a linker or an adaptor.

9. The conjugate of claim 5, wherein the small molecule is conjugated to the constant region of the heavy chain or the light chain of the antibody.

10. A method comprising administering to a subject in need a therapeutically effective amount of:
   (i) an antibody or an immunogenic fragment thereof comprising a VH region comprising CDR1 having an amino acid sequence selected from the group consisting of SEQ ID NOs: 4-19, CDR2 having an amino acid sequence selected from the group consisting of SEQ ID NOs: 20-35, and CDR3 having an amino acid sequence selected from the group consisting of SEQ ID NOs: 36-51; or
   (ii) an antibody-small molecule conjugate comprising the antibody of (i) or an immunogenic fragment thereof, and a small molecule having an anti-proliferative activity against EBV-transformed cells, wherein the small molecule is conjugated to the antibody.

11. The method of claim 10, wherein the subject is a pediatric transplant recipient who is EBV naïve or an adult transplant recipient.

12. The method of claim 10, wherein the administration is before, during, and/or after the transplant.

13. The method of claim 10, wherein the EBV-associated cancer is selected from the group consisting of Hodgkin lymphoma, Burkitt lymphoma, gastric cancer, and nasopharyngeal carcinoma.

14. The method of claim 10, wherein the subject is human.

15. The method of claim 10, wherein the antibody or the immunogenic fragment thereof further comprises a VL region comprising CDR1 having an amino acid sequence selected from the group consisting of SEQ ID NOs: 52-67, CDR2 having an amino acid sequence selected from the group consisting of SEQ ID NOs: 68-83, and CDR3 having an amino acid sequence selected from the group consisting of SEQ ID NOs: 84-99.

16. The conjugate of claim 5, wherein the antibody or the immunogenic fragment thereof further comprises a VL region comprising CDR1 having an amino acid sequence selected from the group consisting of SEQ ID NOs: 52-67, CDR2 having an amino acid sequence selected from the group consisting of SEQ ID NOs: 68-83, and CDR3 having an amino acid sequence selected from the group consisting of SEQ ID NOs: 84-99.

17. The antibody or the immunogenic fragment thereof of claim 1, wherein the antibody is a recombinant antibody.

18. The conjugate of claim 5, wherein the antibody is a recombinant antibody.

19. The method of claim 10, wherein the antibody is a recombinant antibody.

* * * * *

UNITED STATES PATENT AND TRADEMARK OFFICE
CERTIFICATE OF CORRECTION

PATENT NO. : 11,401,323 B2
APPLICATION NO. : 16/609078
DATED : August 2, 2022
INVENTOR(S) : Javier Gordon Ogembo et al.

It is certified that error appears in the above-identified patent and that said Letters Patent is hereby corrected as shown below:

In the Specification

In the Government Interest section, Column 1, Lines 14-17, please delete:
"The present invention was made with government support under Grant No. R21CA205106, awarded by U.S. Public Health Service. The Government has certain rights in the invention."
And replace with:
--This invention was made with government support under R21 CA205106 awarded by the National Institutes of Health. The government has certain rights in the invention.--

Signed and Sealed this
Twenty-ninth Day of August, 2023

Katherine Kelly Vidal
*Director of the United States Patent and Trademark Office*